(12) United States Patent
Di Fiore et al.

(10) Patent No.: US 7,901,876 B2
(45) Date of Patent: Mar. 8, 2011

(54) CANCER MARKERS

(75) Inventors: Pier Paolo Di Fiore, Milan (IT); Salvatore Pece, Milan (IT)

(73) Assignee: IFOM Fondazione Instituto FIRC di Oncologia Molecolare, Milan (IT)

(*) Notice: Subject to any disclaimer, the term of this patent is extended or adjusted under 35 U.S.C. 154(b) by 628 days.

(21) Appl. No.: 11/664,137

(22) PCT Filed: Sep. 20, 2005

(86) PCT No.: PCT/EP2005/010153
§ 371 (c)(1),
(2), (4) Date: Mar. 29, 2007

(87) PCT Pub. No.: WO2006/037462
PCT Pub. Date: Apr. 13, 2006

(65) Prior Publication Data
US 2008/0188405 A1 Aug. 7, 2008

(30) Foreign Application Priority Data
Sep. 30, 2004 (GB) .................................. 0421838.4

(51) Int. Cl.
 *C12Q 1/00* (2006.01)
 *G01N 33/53* (2006.01)
 *G01N 33/574* (2006.01)
(52) U.S. Cl. ............................. 435/4; 436/7.23; 436/7.1
(58) Field of Classification Search ........................ None
See application file for complete search history.

(56) References Cited

U.S. PATENT DOCUMENTS

| 7,171,311 B2 | 1/2007 | Dai et al. ....................... 702/19 |
| 2002/0119365 A1* | 8/2002 | Clarke et al. ................ 435/36 |
| 2004/0175773 A1 | 9/2004 | Amson et al. ............... 435/7.23 |
| 2005/0025751 A1* | 2/2005 | Bodmer et al. ............ 424/93.21 |
| 2005/0208027 A1* | 9/2005 | Conboy et al. ............. 424/93.7 |
| 2005/0272061 A1 | 12/2005 | Petroziello et al. ............. 435/6 |

FOREIGN PATENT DOCUMENTS

| WO | WO 02/103320 | 12/2002 |
| WO | WO 03/011317 | 2/2003 |
| WO | WO 03/088910 | 10/2003 |
| WO | WO 2006/138275 | 12/2006 |

OTHER PUBLICATIONS

Pece et al. JCB vol. 167, p. 215-221, 2004.*
Wu et al MCB, vol. 21, p. 7403-7415, 2001.*
Borgne et al, figure 1, Devolvement vol. 132, p. 1751-1762, 2005.*
Artavanis-Tsakonas et al., Notch signaling: cell fate control and signal integration in development, Science., 284(5415): 770-776 (1999).
Attwooll et al., The E2F family; specific functions and overlapping interests, The EMBO Journal, 23(24): 4709-4716 (2004).
Beer et al., Gene-expression profiles predict survival of patients with lung adenocarcinoma, Nat. Med., 8(8): 816-824 (2002).
Berezovska et al., Aspartate mutations in presenilin and gamma-secretase inhibitors both impair notch1 proteolysis and nuclear translocation with relative preservation of notch1 signaling, J. Neurochem., 75(2): 583-593 (2000).
Bhattacharjee et al., Classification of human lung carcinomas by mRNA expression profiling reveals distinct adenocarcinomas subclasses, Proc. Natl. Acad. Sci. USA., 98(24): 13790-13795 (2001).
Blow et al., Preventing re-replication of chromosomal DNA, Nat. Rev. Mol. Cell Biol., 6(6): 476-486 (2005).
Caldas et al., The molecular outlook, Nature, 415(6871): 484-485 (2002).
Capobianco et al., Neoplastic transformation by truncated alleles of human NOTCH1/TAN1 and NOTCH2, Mol. Cell Biol., 17(11): 6265-6273 (1997).
Chang et al., Gene expression signature of fibroblast serum response predicts human cancer progression: similarities between tumors and wounds, PLoS Biol., 2(2): 0206-0214 (2004).
Chien et al., Numb-associated kinase interacts with phosphotyrosine binding domain of Numb and antagonizes the function of Numb in vivo, Mol. Cell Biol., 18(1): 598-607 (1998).
Colaluca et al., NUMB controls p53 tumour suppressor activity, Nature, 451(7174): 76-80 (2008).
Davidson et al., An increase in the expression of ribonucleotide reductase large subunit 1 is associated with gemcitabine resistance in non-small cell lung cancer cell lines, Cancer Res., 64(11): 3761-3766 (2004).
Ellisen et al., TAN-1, the human homolog of the Drosophila notch gene, is broken by chromosomal translocations in T lymphoblastic neoplasms, Cell, 66(4): 649-661 (1991).
Endoh et al., Prognostic model of pulmonary adenocarcinoma by expression profiling of eight genes as determined by quantitative real-time reverse transcriptase polymerase chain reaction, J. Clin. Oncol., 22(5): 811-819 (2004).
Frise et al., The Drosophila Numb protein inhibits signaling of the Notch receptor during cell-cell interaction in sensory organ lineage, Proc. Natl. Acad. Sci.USA., 93(21): 11925-11932 (1996).
Fukuse et al., Expression of proliferating cell nuclear antigen and CD44 variant isoforms in the primary and metastatic sites of nonsmall cell lung carcinoma with intrapulmonary metastases, Cancer., 86(7): 1174-1181 (1999).
Gallahan et al., Expression of a truncated Int3 gene in developing secretory mammary epithelium specifically retards lobular differentiation resulting in tumorigenesis, Cancer Res., 56(8): 1775-1785 (1996).
Guo et al., Control of daugher cell fates during asymmetric division: interaction of Numb and Notch, Neuron., 17(1): 27-41 (1996).

(Continued)

Primary Examiner—Misook Yu
Assistant Examiner—Lei Yao
(74) Attorney, Agent, or Firm—Morgan, Lewis & Bockius LLP

(57) ABSTRACT

The invention related to methods of diagnosis and prognosis of cancer, the methods comprising determining the level of one or more gene products. In addition, the invention relates to modulators of the gene products for use in treatment of cancer. The genes include EIA-induced genes and Numb.

6 Claims, 22 Drawing Sheets

OTHER PUBLICATIONS

Jeffries et al., Characterization of a high-molecular-weight Notch complex in the nucleus of Notch(ic)-transformed RKE cells and in a human T-cell leukemia cell line, Mol. Cell Biol., 22(11): 3927-3941 (2002).

Jeffries et al., Neoplastic transformation by Notch requires nuclear localization, Mol. Cell Biol., 20(11): 3928-3941 (2000).

Jhappan et al., Expression of an activated Notch-related int-3 transgene interferes with cell differentiation and induces neoplastic transformation in mammary and salivary glands, Genes Dev., 6(3): 345-355 (1992).

Juven-Gershon et al., The Mdm2 oncoprotein interacts with the cell fate regulator Numb, Mol. Cell. Biol., 18(7): 3974-3982 (1998).

Kawai et al., Estrogen receptor alpha and beta are prognostic factors in non-small cell lung cancer, Clin. Cancer Res., 11(14): 5084-5089 (2005).

Lei M, The MCM complex: its role in DNA replication and implications for cancer therapy, Curr. Cancer Drug Targets, 5(5): 365-380 (2005).

Marchetti et al, Down regulation of high in normal-1 (HIN-1) is a frequent event in stage I non-small cell lung cancer and correlates with poor clinical outcome, Clin Cancer Res., 10(4): 1338-1343 (2004).

Nicassio et al., A cancer-specific transcriptional signature in human neoplasia, J. Clin. Invest., 115(11): 3015-3025 (2005).

Pece et al., Loss of negative regulation by Numb over Notch is relevant to human breast carcinogenesis, J. Cell Biol., 167(2): 215-221 (2004).

Robbins et al., Mouse mammary tumor gene int-3: a member of the notch gene family transforms mammary epithelial cells, J. Virol., 66(4): 2594-2599 (1992).

Rosell et al., Gene expression as a predictive marker of outcome in stage IIB-IIIA-IIIB non-small cell lung cancer after induction gemcitabine-based chemotherapy followed by resectional surgery, Clin. Cancer Res., 10(12 Pt 2): 4215s-4219s (2004).

Santolini et al., Numb is an endocytic protein, J. Cell Biol., 151(6): 1345-1352 (2000).

Schroeter et al., Notch-1 signalling requires ligand-induced proteolytic release of intracellular domain, Nature, 393(6683): 382-386 (1998).

Seville et al., Modulation of pRb/E2F Functions in the Regulation of Cell Cycle and in Cancer, Current Cancer Drug Targets, 5(3): 159-170 (2005).

Soriano et al., Expression of an activated Notch4(int-3) oncoprotein disrupts morphogenesis and induces an invasive phenotype in mammary epithelial cells in vitro, Int. J. Cancer, 86(5): 652-659 (2000).

Susini et al., Siah-1 binds and regulates the function of Numb, Proc. Natl. Acad. Sci.USA., 98(26):15067-15072 (2001).

Van't Veer et al., Gene expression profiling predicts clinical outcome of breast cancer, Nature, 415(6871): 530-536 (2002).

Volm et al., Prognostic value of ERBB-1, VEGF, clycin A, FOS, JUN and MYC in patients with squamous cell lung carcinomas, Br. J. Cancer, 77(4): 663-669 (1998).

Weijzen et al., Activation of Notch-1 signaling maintains the neoplastic phenotype in human Ras-transformed cells, Nat Med., 8(9): 979-986 (2002).

Weng et al., Growth suppression of pre-T acute lymphoblastic leukemia cells by inhibition of notch signaling, Mol. Cell Biol., 23(2): 655-664 (2003).

Yang et al., CML66, a broadly immunogenic tumor antigen, elicits a humoral immune response associated with remission of chronic myelogenous leukemia, Proc. Natl. Acad. Sci. USA, 98(13): 7492-7497 (2001).

Chapman et al. (2006) High levels of Notch signaling down-regulate Numb and Numblike, J. Cell Biol. 175(4):535-540.

Colaluca et al. (2008) NUMB controls p53 tumour suppressor activity, Nature 451:76-81, Supplemental Discussion pp. 1-10, Supple. Figs. 1 to 6.

Conboy et al. (2003) Notch-mediated restoration of regenerative potential to aged muscle, Science 302:1575-1577.

* cited by examiner

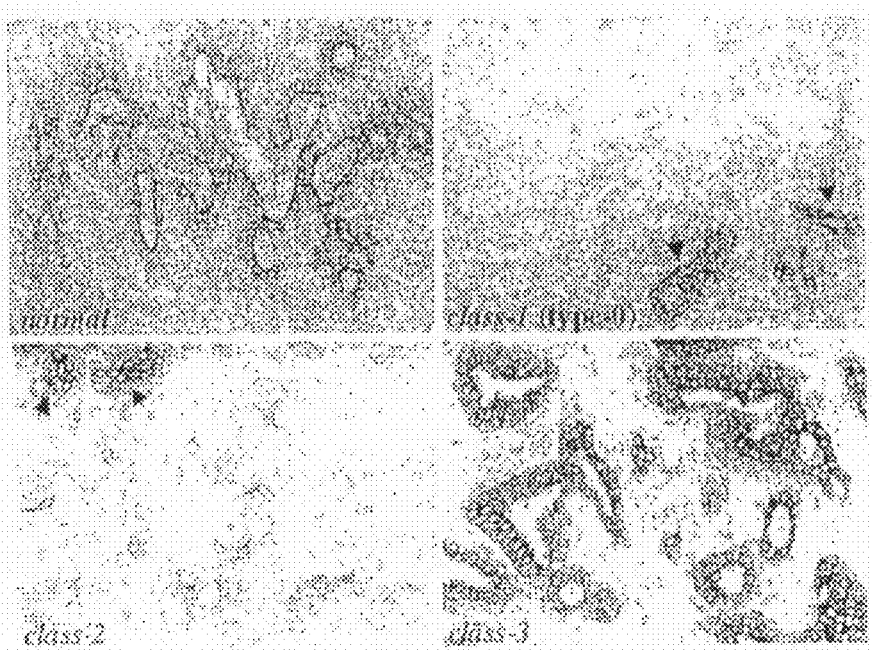
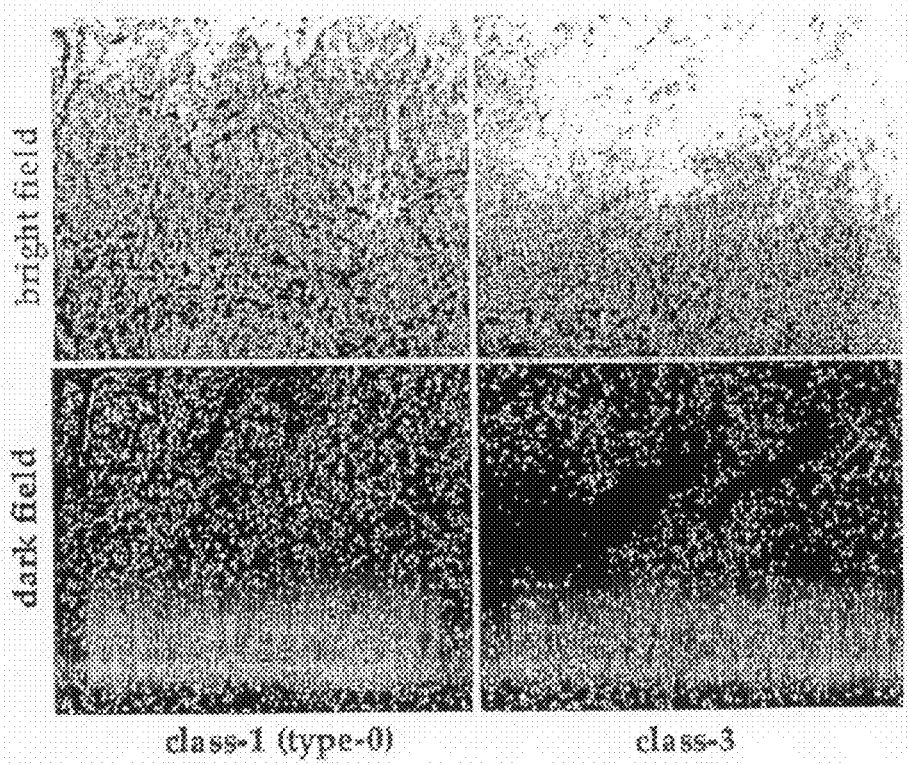
FIG. 1 overall suvival according to NUMB classes (S.Pece)

| ACC. N° (mouse) | NAME AND DESCRIPTION (mouse) | HUMAN HOMOLOG | ACC. N° (human) | SHORT NAME | E1A C2C12 | SD | MYB C2C12 | SD | E1A MSC | SD | MYB MSC | SD |
|---|---|---|---|---|---|---|---|---|---|---|---|---|
| NM_009830 | CCNE2: cyclin E2 | CCNE2 | NM_004702 | CCNE2 | 24.4 | 1.79 | 7.4 | 0.07 | 84.5 | 4.45 | 11.3 | 1.21 |
| NM_008567 | MIS5/MCM6 minichromosome maintenance deficient 6 | MCM6 | NM_005915 | MCM6 | 16.9 | 2.05 | 11.3 | 0.65 | 70.3 | 1.03 | 46.7 | 0.91 |
| NM_019931 | Np95: nuclear protein 95 | UHRF1 | NM_013282 | NP95 | 19.1 | 0.79 | 22.3 | 1.21 | 54.2 | 3.45 | 47.2 | 2.54 |
| NM_007633 | CCNE1: cyclin E1 | CCNE1 | NM_001238 | CCNE1 | 11.1 | 0.23 | 3.2 | 0.02 | 29.6 | 2.60 | 18.6 | 1.00 |
| NM_008568 | cdc47/MCM7: minichromosome maintenance deficient 7 | MCM7 | NM_005916 | MCM7 | 10.8 | 0.04 | 4.4 | 0.02 | 33.2 | 3.57 | 16.0 | 0.52 |
| NM_008565 | cdc21/MCM4: minichromosome maintenance deficient 4 | MCM4 | NM_005914 | MCM4 | 6.6 | 0.39 | 8.7 | 0.00 | 21.7 | 1.90 | 20.9 | 1.02 |
| NM_178693 | XTP1: HBxAg transactiv. Prot.1 | XTP1 | NM_019369 | XTP1 | 7.9 | 1.21 | 14.3 | 1.71 | 12.7 | 0.24 | 10.5 | 1.74 |
| NM_016777 | Nasp (somatic): nuclear autoantigenic sperm prot. | NASP(somatic) | NM_152298 | NASPs | 7.3 | 0.63 | 8.9 | 0.18 | 16.9 | 0.66 | 11.0 | 0.21 |
| NM_026115 | Hat1: histidine aminotransferase 1 | HAT1 | NM_003642 | HAT1 | 6.8 | 0.12 | 3.1 | 0.01 | 15.3 | 0.52 | 7.5 | 0.40 |
| NM_133815 | Lbr: lamin B receptor | LBR | NM_002296 | LBR | 9.1 | 1.50 | 3.6 | 0.58 | 15.8 | 1.01 | 10.5 | 0.77 |
| NM_007891 | E2f1: E2F transcription factor 1 | E2F1 | NM_005225 | E2F1 | 6.7 | 0.50 | 2.2 | 0.05 | 57.1 | 2.79 | 28.5 | 0.86 |
| NM_177294 | RIKEN cDNA C130068N17 | MGC22679 | NM_144711 | MGC22679 | 10.4 | 1.03 | 1.7 | 0.25 | 4.6 | 0.09 | 2.1 | 0.08 |
| NM_009104 | Rrm2: ribonucleotide reductase M2 | RRM2 | NM_001034 | RRM2 | 3.0 | 0.18 | 2.5 | 0.02 | 19.8 | 0.59 | 16.5 | 0.80 |
| NM_176972 | C330008N13Rik: ubiquitin spec. protease 37 | KIAA1594 | NM_020935 | K1594 | 6.0 | 0.72 | 6.6 | 0.12 | 7.2 | 0.62 | 5.2 | 0.22 |
| NM_130287 | 4930432B04Rik/mKIAA0097 | KIAA0097/ch-TOG | NM_014756 | Ch-TOG | 5.7 | 0.34 | 2.3 | 0.02 | 4.9 | 0.21 | 5.7 | 0.08 |
| XM_358357 | 9030416H16Rik/mouse KIAA0648 | KIAA0648 | NM_015200 | K0648 | 5.3 | 0.38 | 2.4 | 0.17 | 3.4 | 0.36 | 3.7 | 0.45 |
| NM_031172 | SAP150: splicing factor 3b, subunit 1 | SF3B1 | NM_012433 | SF3B1 | 3.5 | 0.41 | 1.0 | 0.02 | 7.4 | 0.58 | 3.7 | 0.22 |
| NM_026149 | 4921531K09Rik/mouse Chl_66 | CHL66 | NM_032869 | CHL66 | 3.6 | 0.13 | 1.8 | 0.04 | 4.2 | 0.41 | 4.2 | 0.26 |
| NM_171826 | 1110019C08Rik/mouse C3orf_4 | C3orf4 | NM_019895 | C3orf4 | 2.1 | 0.19 | 1.6 | 0.07 | 4.5 | 0.22 | 4.1 | 0.99 |
| NM_145959 | BC033609 unknown/mouse SKIN | FLJ23790: SKIN | NM_144963 | SKIN | 2.0 | 0.23 | 2.8 | 0.41 | 3.7 | 0.02 | 7.9 | 2.03 |
| NM_011816 | G3BP2: Ras-GTPase-activating protein | G3BP2 | AB014580 | G3BP2 | 3.3 | 0.29 | 1.5 | 0.08 | 3.3 | 0.39 | 2.2 | 0.09 |
| XM_129997 | Taf3: TAF3 RNA polymerase II | TAF3 | XM_291729 | TAF3 | 2.5 | 0.60 | 1.1 | 0.09 | 3.8 | 0.11 | 11.6 | 4.65 |
| NM_019550 | Ptbp2: polypyrimidine tract binding protein 2 | PTBP2 | XM_021190 | PTB2 | 3.3 | 0.40 | 2.3 | 0.18 | 2.9 | 0.22 | 2.7 | 0.32 |
| NM_181278 | RIKEN cDNA B230219D22 | FLJ37562 | NM_152409 | FLJ37562 | 2.7 | 0.15 | 0.8 | 0.42 | 3.6 | 0.26 | 3.0 | 0.52 |
| NM_019693 | Batu: HLA-B-associated transcript 1A | BAT1 | NM_004640 | BAT1 | 2.6 | 0.25 | 2.7 | 0.05 | 3.8 | 0.06 | 5.4 | 0.11 |
| NM_019666 | Synclp: synaptogamin binding | NSAP1 | NM_006372 | NSAP1 | 3.7 | 0.18 | 2.4 | 0.05 | 2.2 | 0.05 | 3.1 | 0.13 |
| NM_019553 | DDX21: DEAD box polypeptide 21 | DDX21 | BC094182 | DDX21 | 2.0 | 0.05 | 2.1 | 0.03 | 2.3 | 0.02 | 2.4 | 0.21 |
| NM_019828 | Trpc4ap: transient receptor pot. Cat. channel 4 ass. Prot | TRPC4AP | BC013144 | TRPC4AP | 2.0 | 0.02 | 0.9 | 0.29 | 3.0 | 0.09 | 1.9 | 0.29 |
| NM_021535 | RIKEN cDNA 2610203K23 | SHU-1 | BC092076 | SHU-1 | 2.0 | 0.03 | 1.4 | 0.01 | 2.3 | 0.05 | 2.7 | 0.10 |

| ACC. N° | NAME | HUMAN HOMOLOG | ACC. N° | SHORT NAME | E1A C2C12 | SD | MYB C2C12 | SD | E1A MSC | SD | MYB MSC | SD |
|---|---|---|---|---|---|---|---|---|---|---|---|---|
| NM_023854 | Zfp289: zinc finger protein 289 | ZNF289 | NM_032389 | ZNF289 | 2.4 | 1.04 | 0.4 | 0.19 | 3.2 | 1.37 | 1.1 | 0.46 |
| NM_020285 | Tssc4: tumor-suppressing subchrom. Transf. Frag. 4 | TSSC4 | NM_005706 | TSSC4 | 1.9 | 0.40 | 2.5 | 0.95 | 3.3 | 1.62 | 4.3 | 1.37 |
| NM_019939 | Mpp6: membrane protein, palmitoylated 6 | MPP6 | NM_019939 | MPP6 | 1.6 | 0.08 | 0.6 | 0.10 | 1.4 | 0.08 | 0.8 | 0.03 |
| NM_011489 | StatSb: signal transducer and activator of transcr. 5B | STAT5B | NM_012448 | STAT5B | 1.8 | 0.12 | 0.8 | 0.19 | 1.2 | 0.11 | 0.4 | 0.13 |
| NM_002568 | PABPC1: poly(A) binding protein, cytoplasmic 1 | PABPC1 | NM_002568 | PABPC1 | 1.9 | 0.57 | 2.5 | 0.71 | 3.1 | 2.15 | 7.0 | 4.62 |
| NM_011370 | Cyfip1: cytoplasmic FMR1 interacting protein 1 | CYFIP1 | NM_014608 | CYFIP1 | 1.7 | 0.69 | 1.3 | 0.24 | 3.1 | 1.79 | 1.1 | 0.36 |
| NM_008229 | Hdac2: histone deacetylase 2 | HDAC2 | NM_001527 | HDAC2 | 1.9 | 0.44 | 1.7 | 0.45 | 2.6 | 0.46 | 2.2 | 0.35 |
| NM_008465 | Kpna1: karyopherin (importin) alpha 1 | KPNA1 | NM_002264 | KPNA1 | 1.7 | 0.28 | 0.9 | 0.09 | 1.5 | 0.09 | 0.7 | 0.09 |
| NM_025287 | SPOP: speckle-type POZ protein | SPOP | NM_003563 | SPOP | 1.5 | 0.10 | 2.1 | 0.03 | 2.4 | 0.34 | 0.9 | 0.09 |
| NM_024325 | Snx5: sorting nexin 5 | SNX5 | NM_014426 | SNX5 | 1.9 | 0.28 | 1.5 | 0.30 | 3.9 | 1.32 | 3.4 | 0.43 |
| NM_007475 | Atpp: acidic ribosomal phosphoprotein P0 | RPLP0 | NM_001002 | ARPPO | 1.4 | 0.07 | 3.0 | 0.07 | 3.4 | 1.22 | 3.2 | 1.34 |
| NM_031165 | Hspa8: heat shock protein 8 | HSPA8 | NM_006597 | HSPA8 | 1.5 | 0.18 | 2.8 | 0.40 | 1.7 | 0.07 | 1.5 | 0.06 |
| XM_130275 | Ppig: peptidyl-prolyl isomerase G (cyclophilin G) | PPIG | NM_004792 | PPIG | 1.6 | 0.13 | 1.4 | 0.46 | 2.2 | 0.34 | 2.0 | 0.00 |
| NM_016921 | Tcirg1: T-cell, immune regulator 1 | TCIRG1 | NM_006019 | TCIRG1 | 1.8 | 6.20 | 2.1 | 0.00 | 3.4 | 0.88 | 1.4 | 0.75 |
| NM_178614 | RIKEN cDNA 1110030I07 | CGI-51 | NM_015380 | CGI-51 | 1.3 | 0.18 | 1.0 | 0.51 | 1.7 | 0.40 | 1.1 | 0.23 |
| NM_018794 | Atp6ap1: ATPase, H+ transp., lysosomal access. Prot. 1 | ATP6AP1 | NM_001183 | ATP6AP1 | 1.3 | 0.03 | 0.9 | 0.00 | 2.5 | 0.21 | 2.2 | 0.03 |
| NM_016701 | Nes: nestin | NES | NM_006617 | nestin | 1.2 | 0.05 | 1.9 | 0.01 | 1.2 | 0.02 | 1.6 | 0.09 |
| NM_011290 | Rpl6: ribosomal protein L6 | RPL6 | NM_000970 | RPL6 | 1.7 | 0.06 | 1.5 | 0.47 | 3.0 | 0.06 | 1.7 | 0.04 |
| NM_145573 | Mrps35: mitochondrial ribosomal protein S35 | MPRS35 | NM_021821 | MPRS35 | 1.9 | 0.10 | 3.7 | 0.29 | 4.0 | 0.47 | 2.8 | 0.51 |
| NM_177301 | Hnrnpl: heterogeneous nuclear ribonucleoprotein L | HNRPL | NM_001533 | hRNPL | 1.6 | 0.05 | 1.3 | 0.02 | 1.3 | 0.19 | 6.3 | 0.15 |
| NM_013765 | Rps26: ribosomal protein S26 | RPS26 | NM_001029 | RPS26 | 1.9 | 0.22 | 3.7 | 0.29 | 3.9 | 0.47 | 2.4 | 0.65 |
| NM_024219 | Hsbp1: heat shock factor binding protein 1 | HSBP1 | NM_001537 | HSBP1 | 1.9 | 0.10 | 1.8 | 0.40 | 1.8 | 0.50 | 1.9 | 0.43 |
| NC_001569 | mt-Nd1: NADH dehydrogenase 1, mitochondrial | mt-Nd1 | NC_001569 | ND1 | 1.8 | 0.09 | 0.8 | 0.03 | 1.4 | 0.03 | 1.1 | 0.07 |
| NM_009290 | Ss18: synovial sarcoma translocation, Chromosome 18 | SS18 | NM_005637 | SS18 | 1.9 | 0.39 | 1.5 | 0.26 | 4.4 | 0.47 | 3.9 | 0.09 |
| NM_007714 | Clk4: CDC like kinase 4 | CLK4 | NM_020666 | CLK4 | 1.9 | 0.20 | 1.5 | 0.01 | 3.0 | 0.07 | 1.9 | 0.08 |

FIG. 10

| CLASS A | | | | | | |
|---|---|---|---|---|---|---|
| ACC. N° | Short Name | YH47 | E2F | Rb rem. | Ratio 24h/36h | TIMING |
| NM_026115 | HAT1 | 0.07 ± 0.0 | 0.24 ± 0.0 | 0.91 ± 0.2 | 0.54 ± 0.3 | EARLY |
| NM_133815 | LBR | 0.20 ± 0.1 | 0.34 ± 0.1 | 2.06 ± 0.2 | 0.48 ± 0.0 | EARLY |
| NM_178683 | XTP1 | 0.07 ± 0.1 | 0.53 ± 0.1 | 0.43 ± 0.1 | 0.41 ± 0.0 | EARLY |
| NM_007633 | CCNE1 | 0.04 ± 0.0 | 0.69 ± 0.2 | 2.99 ± 0.3 | 1.02 ± 0.6 | EARLY |
| NM_009104 | RRM2 | -0.05 ± 0.0 | 0.82 ± 0.1 | 1.53 ± 0.2 | 0.49 ± 0.0 | EARLY |
| NM_009830 | CCNE2 | 0.03 ± 0.0 | 0.73 ± 0.2 | 1.49 ± 0.2 | 0.56 ± 0.2 | EARLY |
| NM_007891 | E2F1 | 0.03 ± 0.0 | 19.17 ± 8.4 | 1.09 ± 0.1 | 0.67 ± 0.3 | EARLY |

| CLASS B | | | | | | |
|---|---|---|---|---|---|---|
| ACC. N° | Short Name | YH47 | E2F | Rb rem. | Ratio 24h/36h | TIMING |
| NM_010931 | NP95 | 0.01 ± 0.0 | 0.17 ± 0.1 | 1.34 ± 0.2 | 0.75 ± 0.3 | EARLY |
| NM_177784 | MGC22679 | 0.18 ± 0.1 | -0.03 ± 0.1 | 2.39 ± 0.2 | 0.68 ± 0.0 | EARLY |
| NM_176972 | K1594 | 0.12 ± 0.7 | 0.02 ± 0.0 | 0.82 ± 0.1 | 0.47 ± 0.1 | EARLY |
| NM_016777 | NASPs | 0.07 ± 0.1 | 0.10 ± 0.1 | 0.90 ± 0.1 | 0.46 ± 0.1 | EARLY |
| NM_008568 | MCM7* | 0.02 ± 0.0 | 0.07 ± 0.1 | 1.16 ± 0.1 | 0.84 ± 0.2 | EARLY |
| NM_008565 | MCM4* | 0.03 ± 0.0 | 0.11 ± 0.0 | 0.73 ± 0.1 | 0.60 ± 0.3 | EARLY |
| NM_008567 | MCM6* | 0.04 ± 0.0 | 0.14 ± 0.0 | 0.64 ± 0.1 | 0.77 ± 0.0 | EARLY |

| CLASS C | | | | | | |
|---|---|---|---|---|---|---|
| ACC. N° | Short Name | YH47 | E2F | Rb rem. | Ratio 24h/36h | TIMING |
| NM_171826 | C3orf4 | 0.30 ± 0.1 | 0.09 ± 0.0 | 1.27 ± 0.1 | 0.21 ± 0.1 | LATE |
| NM_011816 | G3BP2 | 0.40 ± 0.1 | 0.05 ± 0.1 | 0.71 ± 0.1 | 0.26 ± 0.0 | LATE |
| XM_129997 | TAF3 | 0.44 ± 0.2 | 0.07 ± 0.0 | 0.98 ± 0.1 | 0.36 ± 0.1 | LATE |
| NM_026149 | CML66 | 0.53 ± 0.1 | 0.06 ± 0.0 | 0.60 ± 0.1 | 0.35 ± 0.0 | LATE |
| XM_358357 | K0648 | 0.60 ± 0.0 | 0.48 ± 0.1 | 2.97 ± 0.5 | 0.27 ± 0.2 | LATE |
| NM_019666 | NSAP1 | 0.60 ± 0.2 | 0.19 ± 0.2 | 2.13 ± 0.2 | 0.02 ± 0.1 | LATE |
| NM_181278 | FLJ37562 | 0.61 ± 0.1 | 0.04 ± 0.3 | 0.75 ± 0.1 | 0.19 ± 0.2 | LATE |
| NM_019693 | BAT1 | 0.62 ± 0.3 | 0.06 ± 0.3 | 0.80 ± 0.2 | 0.33 ± 0.0 | LATE |
| NM_019550 | PTB2 | 0.70 ± 0.1 | 0.15 ± 0.1 | 1.65 ± 0.1 | 0.10 ± 0.2 | LATE |

| CLASS D | | | | | | |
|---|---|---|---|---|---|---|
| ACC. N° | Short Name | YH47 | E2F | Rb rem. | Ratio 24h/36h | TIMING |
| NM_021535 | SMU-1 | 0.44 ± 0.2 | 0.20 ± 0.2 | 0.29 ± 0.1 | 0.38 ± 0.1 | LATE |
| NM_031179 | SF3B1 | 0.47 ± 0.1 | 0.19 ± 0.3 | 0.55 ± 0.1 | 0.07 ± 0.0 | LATE |
| XM_130287 | Ch-TOG | 0.51 ± 0.2 | 0.32 ± 0.1 | 0.30 ± 0.2 | 0.19 ± 0.1 | LATE |
| NM_145959 | SKIN | 0.68 ± 0.4 | 0.15 ± 0.3 | 0.01 ± 0.1 | 0.27 ± 0.2 | LATE |
| NM_019828 | TRPC4AP | 0.81 ± 0.6 | 0.02 ± 0.2 | 0.18 ± 0.1 | 0.36 ± 0.2 | LATE |
| NM_019553 | DDX21 | 1.11 ± 0.3 | 0.20 ± 0.2 | 0.26 ± 0.1 | 0.28 ± 0.2 | LATE |

FIG. 11 a
| | | Breast | Colon | Kidney | Larynx | Lung | Prost. | Stom. | Uterus | Melan. | Brain |
|---|---|---|---|---|---|---|---|---|---|---|---|
| SF3B1 | %(n) | 23%(13) | 77%(13) | 0%(13) | 6%(18) | 35%(31) | 0%(20) | 12%(26) | 21%(19) | 0%(12) | 7%(15) |
| Ch-TOG | %(n) | 21%(19) | 71%(24) | 0%(7) | 44%(9) | 18%(22) | 0%(6) | 50%(12) | 19%(21) | 13%(13) | 32%(19) |
| SKIN | %(n) | 21%(67) | 87%(33) | 0%(8) | 71%(17) | 29%(41) | 0%(20) | 29%(23) | 36%(25) | 88%(17) | 13%(16) |
| TRCP4AP | %(n) | 56%(16) | 54%(13) | 4%(25) | 4%(23) | 28%(36) | 5%(19) | 37%(30) | 11%(18) | 63%(8) | 0%(13) |
| SMU-1 | %(n) | 27%(15) | 31%(13) | 0%(21) | 7%(27) | 13%(31) | 0%(21) | 10%(30) | 12%(17) | 0%(8) | 0%(15) |
| DDX21 | %(n) | 88%(9) | 77%(13) | 0%(25) | 52%(21) | 56%(34) | 0%(13) | 55%(29) | 33%(18) | 33%(9) | 0%(15) |
b
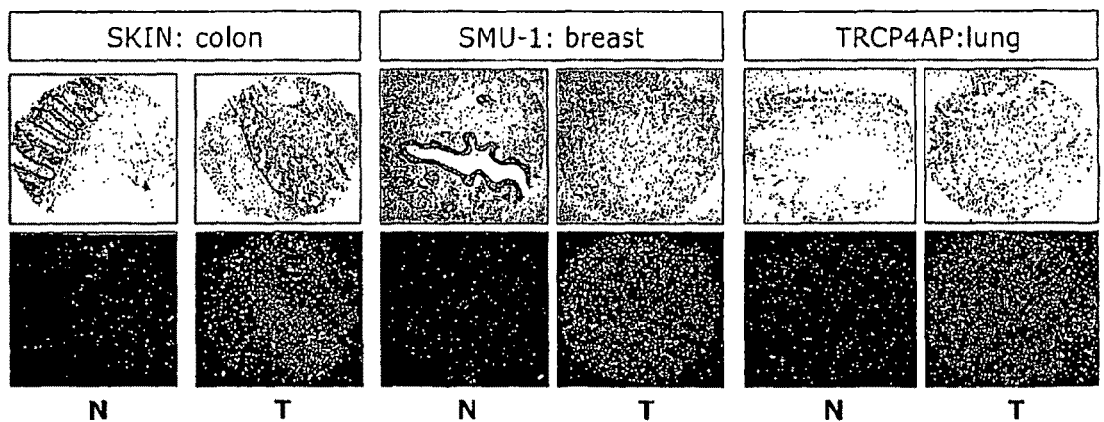
c
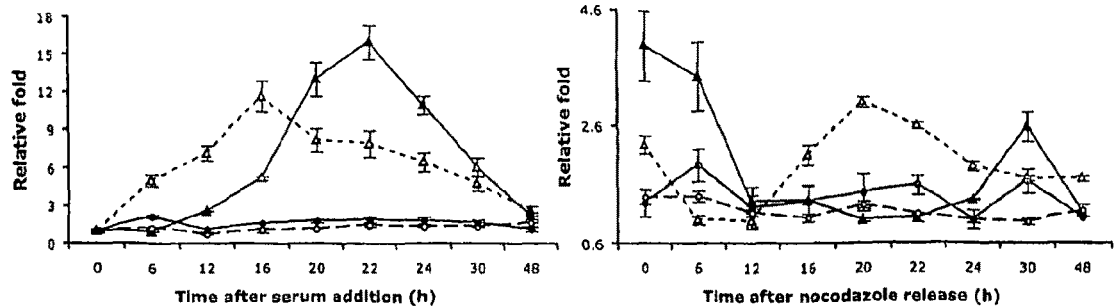
FIG. 12

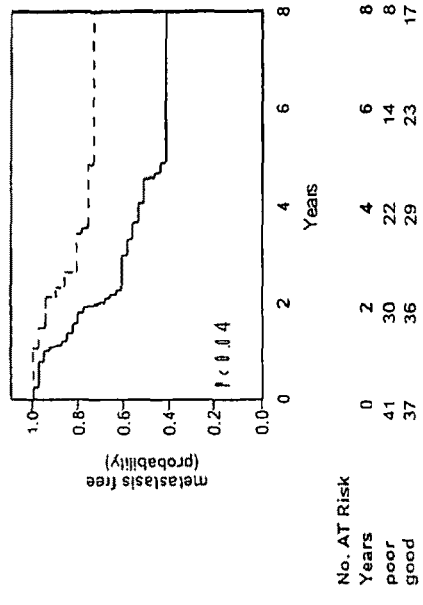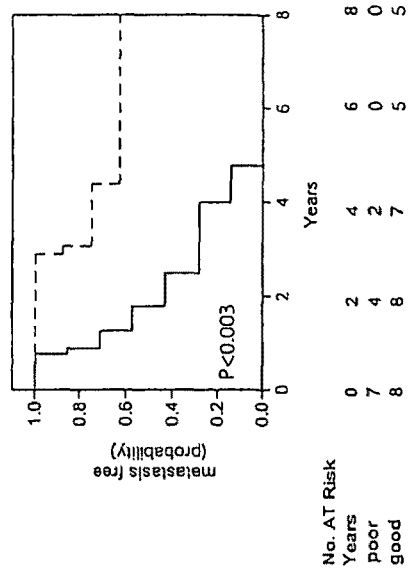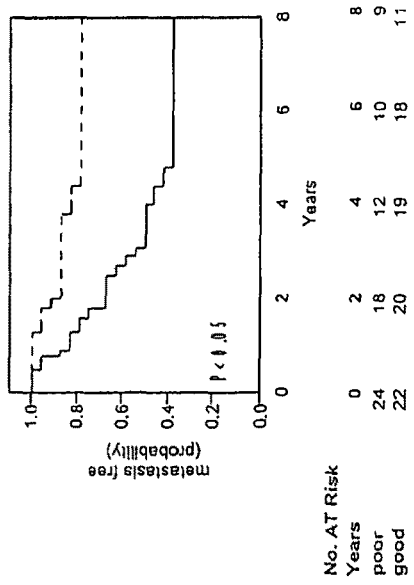
FIG. 14

| Symbol | PUBMED ID | N (log2 median) | T (log2 median) | p-value | site | N total | T total |
|---|---|---|---|---|---|---|---|
| SMU-1 | 11742071 | -0.989 | -0.614 | 0.024 | multi-cancer | 90 | 218 |
| SF3B1 | 11742071 | -0.371 | 1.163 | 0.041 | pancreas | 21 | 11 |
| ch-TOG | 11707567 | -0.638 | 0.083 | 0.005 | lung | 17 | 139 |
| ch-TOG | 12058060 | -1.156 | -0.825 | <0.001 | liver | 76 | 104 |
| ch-TOG | 12368205 | -0.678 | 0.277 | <0.001 | salivary gland | 6 | 16 |
| DDX21 | 11158614 | -0.207 | 0.289 | 0.027 | ovary | 4 | 28 |
| DDX21 | 11742071 | -1.023 | 0.33 | 0.032 | brain | 20 | 10 |

| Symbol | PUBMED ID | T (log2 median) | M (log2 median) | p-value | site | T total | M total |
|---|---|---|---|---|---|---|---|
| SF3B1 | 12154061 | -0.066 | 0.138 | 0.001 | prostate | 23 | 9 |
| SF3B1 | 11707567 | -0.52 | -0.213 | 0.021 | lung | 123 | 16 |
| ch-TOG | 11707567 | 0.056 | 0.288 | 0.011 | lung | 123 | 16 |

FIG. 16

Kaplan-Meier Plots
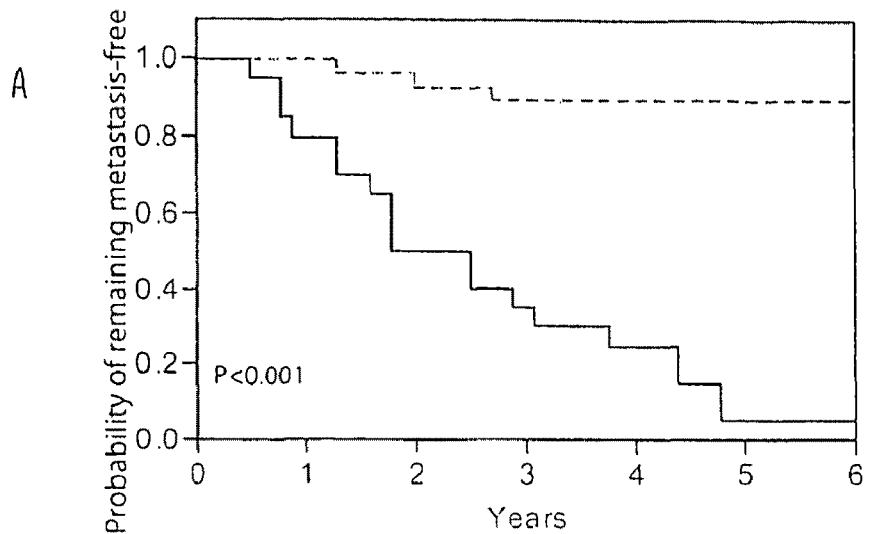
A
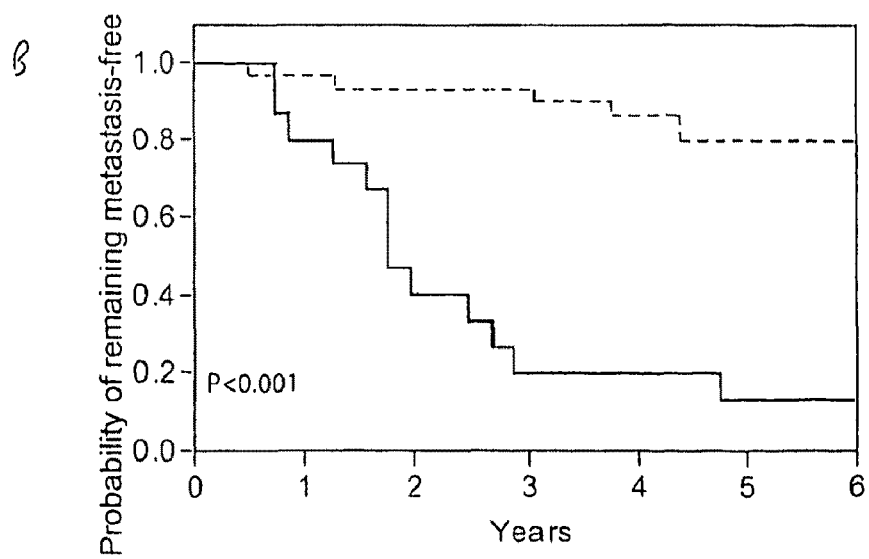
B
FIG. 18

Kaplan-Meier Plots
A
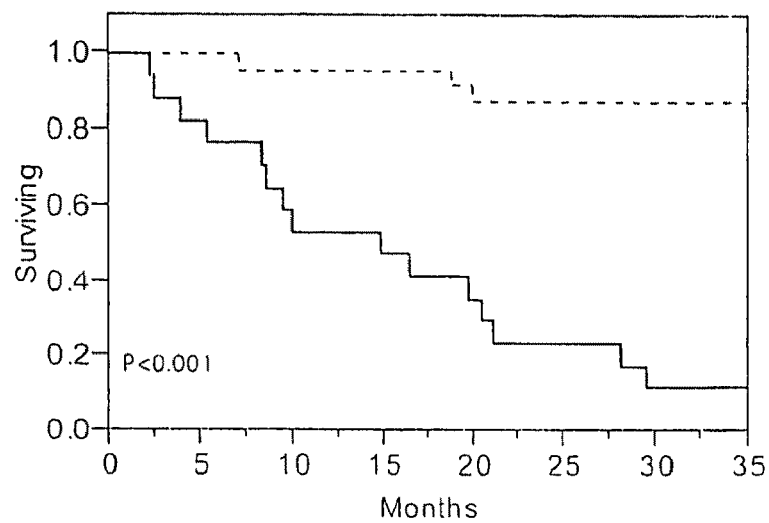
B
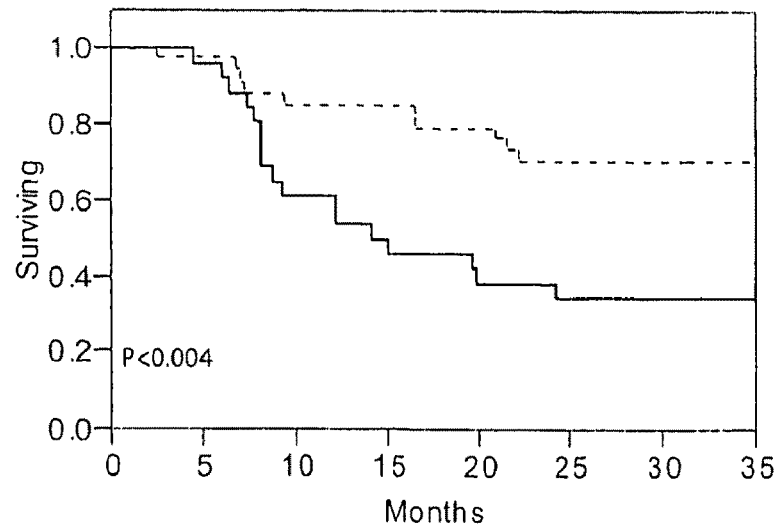
FIG. 19

```
                             SEQUENCE LISTING

<160> NUMBER OF SEQ ID NOS: 22

<210> SEQ ID NO 1
<211> LENGTH: 22
<212> TYPE: DNA
<213> ORGANISM: Artificial sequence
<220> FEATURE:
<223> OTHER INFORMATION: Synthetic antisense nucleic acid

<400> SEQUENCE: 1
aacagcccac tgaacaagca ga                                              22

<210> SEQ ID NO 2
<211> LENGTH: 21
<212> TYPE: DNA
<213> ORGANISM: Artificial sequence
<220> FEATURE:
<223> OTHER INFORMATION: Synthetic sequence targeted by Numb siRNA

<400> SEQUENCE: 2
aacagccact gaacaagcag a                                               21

<210> SEQ ID NO 3
<211> LENGTH: 21
<212> TYPE: DNA
<213> ORGANISM: Artificial sequence
<220> FEATURE:
<223> OTHER INFORMATION: Sequence targeted by scrambled siRNA

<400> SEQUENCE: 3
agacgaacaa gtcaccgact t                                               21

<210> SEQ ID NO 4
<211> LENGTH: 271
<212> TYPE: DNA
<213> ORGANISM: Artificial sequence
<220> FEATURE:
<223> OTHER INFORMATION: Synthetic sense probe

<400> SEQUENCE: 4
ccatcctctc ccacctctcc tacttctgat gccacgacct ctctggagat gaacaatcct       60
catgccatcc cacgccggca tgctccaatt gaacagcttg ctcgccaagg ctctttccga      120
ggttttcctg ctcttagcca gaagatgtca ccctttaaac gccaactatc cctacgcatc      180
aatgagttgc cttccactat gcagaggaag actgatttcc ccattaaaaa tgcagtgcca      240
gaagtagaag gggaggcaga gagcatcagc t                                    271

<210> SEQ ID NO 5
<211> LENGTH: 21
<212> TYPE: DNA
<213> ORGANISM: Artificial sequence
<220> FEATURE:
<223> OTHER INFORMATION: Synthetic primer Hes1_Fw
```

<400> SEQUENCE: 5
cagcttggct gtggtagaag c                                              21

<210> SEQ ID NO 6
<211> LENGTH: 23
<212> TYPE: DNA
<213> ORGANISM: Artificial sequence
<220> FEATURE:
<223> OTHER INFORMATION: Synthetic primer Hes1_Rev

<400> SEQUENCE: 6
ccactgaccc ctaccttcta tcc                                            23

<210> SEQ ID NO 7
<211> LENGTH: 22
<212> TYPE: DNA
<213> ORGANISM: Artificial sequence
<220> FEATURE:
<223> OTHER INFORMATION: Synthetic primer GAPDH_Fw

<400> SEQUENCE: 7
gcctcaagat catcagcaat gc                                             22

<210> SEQ ID NO 8
<211> LENGTH: 23
<212> TYPE: DNA
<213> ORGANISM: Artificial sequence
<220> FEATURE:
<223> OTHER INFORMATION: Synthetic primer GAPDH_Rev

<400> SEQUENCE: 8
ccacgatacc aaagttgtca tgg                                            23

<210> SEQ ID NO 9
<211> LENGTH: 18
<212> TYPE: DNA
<213> ORGANISM: Artificial sequence
<220> FEATURE:
<223> OTHER INFORMATION: Synthetic D14S277 primer

<400> SEQUENCE: 9
ctccccattg ctttcact                                                  18

<210> SEQ ID NO 10
<211> LENGTH: 19
<212> TYPE: DNA
<213> ORGANISM: Artificial sequence
<220> FEATURE:
<223> OTHER INFORMATION: Synthetic D14S277 primer

<400> SEQUENCE: 10
ttgaagattc agataaggt                                                 19

<210> SEQ ID NO 11
<211> LENGTH: 18
<212> TYPE: DNA
<213> ORGANISM: Artificial sequence
<220> FEATURE:
<223> OTHER INFORMATION: Synthetic D14S43 primer

<400> SEQUENCE: 11
ctggaacact caggcgag                                                  18

<210> SEQ ID NO 12

```
<211> LENGTH: 18
<212> TYPE: DNA
<213> ORGANISM: Artificial sequence
<220> FEATURE:
<223> OTHER INFORMATION: Synthetic D14S43 primer

<400> SEQUENCE: 12
gccactttct actttggg                                                 18

<210> SEQ ID NO 13
<211> LENGTH: 18
<212> TYPE: DNA
<213> ORGANISM: Artificial sequence
<220> FEATURE:
<223> OTHER INFORMATION: Synthetic D14S71 primer

<400> SEQUENCE: 13
tgtgcaccaa tgcctcct                                                 18

<210> SEQ ID NO 14
<211> LENGTH: 18
<212> TYPE: DNA
<213> ORGANISM: Artificial sequence
<220> FEATURE:
<223> OTHER INFORMATION: Synthetic D14S71 primer

<400> SEQUENCE: 14
gcccggccag aaatgctt                                                 18

<210> SEQ ID NO 15
<211> LENGTH: 17
<212> TYPE: DNA
<213> ORGANISM: Artificial sequence
<220> FEATURE:
<223> OTHER INFORMATION: Synthetic D14S77 primer

<400> SEQUENCE: 15
gcctgagtca ctgtgcc                                                  17

<210> SEQ ID NO 16
<211> LENGTH: 20
<212> TYPE: DNA
<213> ORGANISM: Artificial sequence
<220> FEATURE:
<223> OTHER INFORMATION: Synthetic D14S77 primer

<400> SEQUENCE: 16
cagacagaaa ttaaccagag                                               20

<210> SEQ ID NO 17
<211> LENGTH: 22
<212> TYPE: DNA
<213> ORGANISM: Artificial sequence
<220> FEATURE:
<223> OTHER INFORMATION: Synthetic D14S268 primer

<400> SEQUENCE: 17
agcttcctac tgtgtaaaac ga                                            22

<210> SEQ ID NO 18
<211> LENGTH: 20
<212> TYPE: DNA
<213> ORGANISM: Artificial sequence
<220> FEATURE:
<223> OTHER INFORMATION: Synthetic D14S268 primer

<400> SEQUENCE: 18
```

-continued

```
ggctggggct gcaccttgta                                          20

<210> SEQ ID NO 19
<211> LENGTH: 24
<212> TYPE: DNA
<213> ORGANISM: Artificial sequence
<220> FEATURE:
<223> OTHER INFORMATION: Synthetic D14S70 primer

<400> SEQUENCE: 19
agctaatgac ttagacacgt tgta                                     24

<210> SEQ ID NO 20
<211> LENGTH: 20
<212> TYPE: DNA
<213> ORGANISM: Artificial sequence
<220> FEATURE:
<223> OTHER INFORMATION: Synthetic D14S70 primer

<400> SEQUENCE: 20
atcaatttgc tagtttggca                                          20

<210> SEQ ID NO 21
<211> LENGTH: 12
<212> TYPE: DNA
<213> ORGANISM: Artificial sequence
<220> FEATURE:
<223> OTHER INFORMATION: Synthetic D14S785 primer

<400> SEQUENCE: 21
gctctgtctc ac                                                  12

<210> SEQ ID NO 22
<211> LENGTH: 21
<212> TYPE: DNA
<213> ORGANISM: Artificial sequence
<220> FEATURE:
<223> OTHER INFORMATION: Synthetic D14S785 primer

<400> SEQUENCE: 22
gatcattgac ataggaaaca c                                        21
```

US 7,901,876 B2

CANCER MARKERS

CROSS-REFERENCE TO RELATED APPLICATION

The present application is a U.S. National Phase Application of International Application PCT/EP2005/010153 (filed Sep. 20, 2005), which claims the benefit of GB Patent Application 0421838.4 (filed Sep. 30, 2004) all of which are hereby incorporated by reference in their entirety.

FIELD OF THE INVENTION

The present invention relates to novel markers for cancer, and the use of these markers in assessment of disease conditions and in therapy.

BACKGROUND TO THE INVENTION

Many genes have been proposed as putative oncogenes, e.g., due to their effects in experimental systems. However, a significant challenge of molecular oncology is to establish whether and how these putative oncogenes play a role in naturally occurring malignancies.

Notch genes encode heterodimeric transmembrane receptors that regulate differentiation, proliferation and apoptosis. Mammals have four known Notch genes, Notch 1-4.

Notch genes have been implicated as oncogenes in several experimental models of carcinogenesis [4-7,9]. For example, it has been reported that Notch is upregulated in Ras transformed cells[8]. It has also been shown that aberrant Notch proteins resulting from MMTV insertional mutation or from transgenic overexpression can profoundly impair the normal mammary gland morphogenesis in mice and promote the rapid development of poorly differentiated adenocarcinomas[4,11].

However, although deregulated expression of the wild type Notch protein has been described in certain cancers[8], no genetic lesion of the Notch locus has been described, with the exception of a rare translocation in T cell malignancies[10].

In view of the importance of finding new markers and therapeutic targets for the assessment and treatment of cancer, there is a continuing need to characterise whether and how signalling pathways are altered in spontaneously occurring tumours.

In additional, a significant amount of work has been carried out in the art to identify "cancer signatures", which can be used in patient management or which can identify the targets subverted in neoplasia. These efforts are mainly concentrated on unbiased screening of cancer transcriptomes. For example, one approach is to identify genes whose expression is significantly modified in tumours as compared to normal cells, or in tumours of different grades (e.g., Beer et al, Nature Medicine Vol. 8, No. 8, 816-824, 2002) and to select from these a subset which are associated with survival. A difficulty of this approach is that the resultant signatures often represent the end point of complex upstream interactions, and cannot readily be allocated to particular molecular pathways.

Another approach has been used in Brown PO et al (PloS Biol. Feb. 2, 2004(2)). Here, gene expression profiles were obtained from fibroblasts, in response to serum exposure. Genes which formed part of this fibroblast common serum response were found to be regulated in many human tumours. It was proposed that this is due to similarity in the molecular mechanism of cancer progression and wound healing.

Signatures produced in the prior art are often not highly robust, and often fail to provide good results from datasets that have been obtained in different clinical environments and from different patients. Additionally, prior art signatures often include a large number of genes, which increases the cost and difficulty of clinical screening in patients.

Therefore, there is also a continuing need to develop new approaches to identifying cancer signatures, so as to identify new diagnostic, prognostic or therapeutic markers.

SUMMARY OF THE INVENTION

The present invention is based, in part, on the finding that Numb-Notch antagonism is relevant to the homeostatis of normal tissue, and that its subversion contributes to cellular transformation in tumours.

Numb is a protein which, in *Drosophila*, determines cell fate as a result of its asymmetric partitioning at mitosis[12], especially in the nervous system. The function of Numb in embryogenesis has been linked to its ability to bind and counteract Notch [1-3]. Numb is also expressed in adult mammalian cell types, though its function here is unknown[13]. The present inventors have now shown not only that the Numb-Notch antagonism is significant in the homeostasis of adult, normal tissue, but that Numb status is a cause of subverted Notch signalling in human tumours.

Accordingly, in a first aspect, the invention provides a method of providing an indicator for the assessment of cancer in a patient, the method comprising:
  providing an assay sample of tissue obtained from said patient; and
  determining the Numb status of said sample.

In a preferred embodiment, the method further comprises determining the status of one or more additional proteins which are prognostic or diagnostic indicators for the cancer, e.g., one or more oncogenes, mitogens, oncosuppressors, cell cycle effectors, or transcriptional regulators. For example, ErbB2 may be a suitable further protein for breast cancer.

The protein may be a protein which, in normal cells, serves as a protective factor against cancer.

In a preferred embodiment the method comprises determining the status of p53 in addition to Numb, e.g., in a prognostic method.

In some embodiments, it may be preferred that the method comprises determining the status in the assay sample of ER (the estrogen or oestrogen receptor) in addition to Numb, particularly in a prognostic method, and particularly when the cancer is breast cancer. Preferably the method comprises determining the status of p53 and ER, e.g., in prognosis of a cancer, and preferably breast cancer.

The invention also provides a kit for the assessment of cancer in a patient, the kit comprising a specific binding partner for a Numb gene expression product (preferably a Numb protein), and a specific binding partner for at least one other gene expression product, wherein said gene expression product is associated with prognosis or diagnosis of the cancer (e.g., as described above).

Preferably, the kit comprises a specific binding partner for p53 and/or ER transcript or protein, particularly where the kit is for the prognosis of cancer (e.g., breast cancer).

The inventors have found that Numb status is a particularly effective indicator of disease progression in p53+ and/or ER– backgrounds, and even more so in a ER–p53+ background. By a p53+ background, is meant a background in which p53 is expressed in a mutated version. In a p53– background, p53 is not expressed. The non-expression of p53 is the normal basal state, as P53 is activated by stress conditions and drives normal cells to growth arrest and/or apoptosis. ER negative breast tumours are general correlated with poorer prognosis than ER+ tumours (Baselga and Norton, Cancer Cell 1, 319-322, 2002). P53 mutation (i.e., the p53 positive state referred to herein) has also been linked with poor prognosis in certain cancers, including breast cancer (Pharoah P D, Day N E, Caldas C: Somatic mutations in the p53 gene and prognosis in breast cancer. Br J Cancer 80(12): 1968-1973, 1999).

Surprisingly, the inventors have found that in a p53+/ER− background, the prognosis is dramatically affected by Numb status. The prognosis for patients having approximately normal levels of Numb appears good (e.g., as good if not better than in ER+ patients) and the prognosis for patients having very little Numb appears poor. Therefore, the value of determining ER and/or P53 status in prognosis is greatly improved by also determining Numb status.

The present inventors have further found that inhibiting Notch signalling, either by re-instatement of Numb activity or using another inhibitor of Notch signalling, is capable of causing a substantial reduction in cell proliferation in tumours which are Numb deficient but not in tumours with normal levels of Numb.

Accordingly, in another aspect the invention provides a method of determining susceptibility of a tumour in a patient to treatment with an inhibitor of Notch signalling, the method comprising:

providing a sample of tumour tissue obtained from said patient; and determining the Numb status of said sample.

The method may further include the step of administering an inhibitor of Notch signalling to said patient.

It may be desired to measure Notch activity in a sample obtained from the patient prior to and subsequent to administration of such an inhibitor, e.g., to monitor the effectiveness of the treatment in the patient. Obtaining the sample and treating the patient are not necessary parts of this method, although either or both of these may optionally be present as additional steps.

In a still further aspect, the invention provides the use of an inhibitor of Notch signalling in the manufacture of a medicament for the treatment of cancer in a patient, wherein said patient has reduced Numb activity in a tumour relative to a control sample, e.g., a normal tissue. For instance, the inhibitor of Notch signalling may be an agent which restores the level of Numb protein, as described in more detail below. Numb activity can be measured in any of the ways described for assessing Numb status, below.

The patient preferably has reduced levels of Numb protein in the tumour relative to a control sample, e.g., relative to a sample of healthy tissue from the same patient. The cancer is preferably breast cancer.

In some embodiments the patient has been subject to a method of determining susceptibility of a tumour in a patient to treatment with an inhibitor of Notch signalling, as described above.

In a still further aspect, the invention provides a kit for the assessment of cancer in a patient (e.g., for the provision of a diagnostic or prognostic indicator of cancer, for the determination of an appropriate treatment regime or for the assessment of the susceptibility of a tumour in a patient to treatment with an inhibitor of Notch signalling) comprising a specific binding partner of a Numb gene expression product (preferably of Numb protein), wherein said binding partner is immobilised on a solid support. The invention also provides for the use of a specific binding partner of a Numb gene expression product (e.g., of Numb protein) in the manufacture of a kit for the assessment of cancer in a patient.

The inventors have also found that enhanced ubiquitination of Numb is a mechanism by which the Numb-Notch signalling is subverted in human tumours. Accordingly, inhibitors of Numb ubiquitination are proposed for use as therapeutics for the treatment of cancer.

Therefore, in a still further aspect there is provided a method of screening for a candidate agent for the treatment of cancer in a patient, comprising:

providing a test system comprising a Numb polypeptide and an enzyme capable of targeting Numb for degradation;

contacting said test system with a test agent; and assessing the ability of the test agent to inhibit the targeting of Numb for degradation.

It is preferred that in aspects of the invention above which comprise determining the Numb status of said sample, this determination is made by determining the level of Numb protein in said sample. The method may further comprise comparing said level to a reference level obtained from a control sample.

In each of the above aspects, it may be preferred that the cancer is breast cancer.

In other aspects, the invention is based on a novel approach to identifying cancer-specific transcription signatures. The inventors have developed an approach which uses well defined molecular tools capable of forcing terminally differentiated cells in culture to re-enter the cell cycle.

The method therefore relates to a biased method of identifying cancer signatures, in which the examination of the cancer transcriptome is biased towards (or indeed, focused primarily or entirely on) genes which have been shown to be modulated in response to agents which force re-entry of terminally differentiated cells into the cell cycle. The method is based on the hypothesis that the molecular tools mimic pathways subverted in naturally occurring tumours and that a limited number of altered signalling pathways lead to the malignant state.

The inventors have found that the signatures obtained by the method can provide good indicators for the assessment of cancer and cancer progression.

In additional, the genes identified in such a screen can be more readily reverse engineered into signalling pathways, and thus, pathways of particular interest in human cancers can be identified.

Therefore, the invention broadly relates to such biased methods of identifying markers for detection in a method of assessment of cancer, and to markers identified in such a method.

In one aspect, the invention provides a method of selecting a specific binding partner of a gene expression product for use in providing an indicator for the assessment of cancer in a patient, the method comprising identifying a gene:

whose expression is modulated by contacting a terminally differentiated mammalian cell in culture with an agent which causes the cell to re-enter the cell cycle; and selecting a specific binding partner for an expression product of said gene.

In one embodiment, the gene has modulated expression in a mammalian tumour.

Agents which are capable of overcoming withdrawal from the cell cycle in terminally differentiated cells overcome very stringent regulation of the cell cycle. The inventors reasoned that this may arise from the mimicry of important cancer pathways. Suitable agents for use in causing re-entry of terminally differentiated (TD) cells into the cell cycle may include E1A from adenovirus (particularly the 12S mRNA product), E7 from papilloma virus and T-large antigen from SV40, or any fragments, splice variants or variants of these which retain the biological activity.

Preferably, the method comprises selecting a set of genes/specific binding partner for assessment using this biased approach, i.e., identifying two or more said genes and selecting specific binding partners for an expression product of said two or more genes.

Preferably, in the above aspects, the cell and/or tumour is primate or rodent (e.g., mouse), and more preferably human.

Modulated expression in the cultured cell or in the mammalian tumour may be induced or inhibited expression.

The method preferably comprises identifying at least two said genes, and selecting a specific binding partner for the at least two genes.

The method may comprise identifying at least two genes
a) whose expression is modulated by contacting a terminally differentiated mammalian cell in culture with an agent which causes re-entry of the cell into the cell cycle;
b) which belong to the same signalling pathway.

In one embodiment, said genes have modulated expression in a mammalian tumour.

The signalling pathway to which the genes belong may be assessed by determining the dependence or independence of modulation of expression on a factor known to be required for certain responses to the agent and not to others.

For example, the genes which are identified may belong to the same E1A induced pathway. Preferably, the gene or genes are not strongly modulated, e.g., induced, by inactivation of a pocket protein such as Rb (the retinoblastoma tumour suppressor), and are significantly modulated, e.g., induced, by an E1A pocket binding mutant.

In one embodiment, the invention may provide a method of selecting a specific binding partner of a gene expression product for use in providing an indicator for the assessment of cancer in a patient, the method comprising identifying a gene whose expression is modulated by contacting a terminally differentiated mammalian cell in culture with E1A so as to cause re-entry of the cell into the cell cycle; and selecting a specific binding partner for an expression product of said gene. The gene may have modulated expression in a mammalian tumour and/or during tumor progression.

The method may comprise identifying at least one gene (optionally, at least two genes):
a) whose expression is modulated by contacting a terminally differentiated mammalian cell in culture with E1A so as to cause re-entry of the cell into the cell cycle;
b) whose expression is not strongly modulated, e.g., induced, by inactivation of a pocket protein (e.g., the retinoblastoma tumour suppressor), and is significantly modulated, e.g., induced, by an E1A pocket binding mutant; and
c) which has modulated expression in a mammalian tumour; and selecting a specific binding partner for an expression product of said gene.

Having selected the specific binding partner or partners, they can be used for the detection of the gene expression product in a sample taken from a patient, e.g., in the assessment of cancer. Hence, having selected the specific binding partner(s), the invention further provides producing a kit for use in providing an indicator for the assessment of cancer, the kit comprising the specific binding partner(s).

The invention also provides a method of providing an indicator for the assessment of cancer, the method comprising, having selected the binding partners, providing an assay sample of tissue obtained from a patient, and determining the level of at least one gene expression product by determining binding to the selected binding partner or partners.

The inventors have used the methods of the present invention to identify markers which are of use in the assessment of cancer.

In one embodiment, the inventors have identified a class of genes which are strongly associated with human cancers. Thus, one aspect of the invention concerns methods of assessment of cancer which comprise assessing the status of members of this class of genes.

Overall, the class of genes are genes whose expression is not strongly modulated, e.g., induced, by inactivation of a pocket protein, preferably Rb, and which are significantly modulated (e.g., induced) by an E1A pocket binding mutant, particularly the E1A pocket binding mutant YH47. The mutant is described in Wang HG et al, "Identification of specific adenovirus E1A N-terminal residues critical to the binding of cellular proteins and to the control of cell growth", J Virol. January 1993; 67(1): 476-88.

The inventors have shown that genes in this class, DDX21, SF3B1, ch-TOG, SKIN, TRPC4AP and SMU-1, are upregulated in a significant proportion of human cancers (relative to normal tissue), and can also be used as predictors of cancer progression. Moreover, this E1A induced pathway appears to represent a useful therapeutic target. The inhibition of expression of an example of this class of genes, SKIN, is able to dramatically reduce proliferation in cancer cell lines overexpressing SKIN while having no effect on normal cells.

In another embodiment, the inventors have identified other classes of genes which are induced by E1A and which can be used as predictors of cancer progression.

The classes of genes are genes whose expression is
(a) strongly modulated, e.g., induced, by inactivation of a pocket protein, preferably Rb, not modulated (e.g., induced) by an E1A pocket binding mutant, particularly the E1A pocket binding mutant YH47 and strongly induced by E2F1 overexpression
(b) strongly modulated, e.g., induced, by inactivation of a pocket protein, preferably Rb, not modulated (e.g., induced) by an E1A pocket binding mutant, particularly the E1A pocket binding mutant YH47 and not (or scarcely) induced by E2F1 overexpression
(c) strongly modulated, e.g., induced, by inactivation of a pocket protein, preferably Rb, modulated (e.g., induced) by an E1A pocket binding mutant, particularly the E1A pocket binding mutant YH47 and not (or scarcely) induced by E2F1 overexpression.

Examples of genes included in these classes are represented in FIG. 11.

In one embodiment, the present invention provides a method of providing an indicator for assessment of cancer in a patient, the method comprising:
providing an assay sample of tissue obtained from said patient;
determining the level in the sample of an expression product of at least one gene selected from DDX21, SF3B1, ch-TOG, SKIN, TRPC4AP and SMU-1, or other gene listed in FIG. 11. The method may further comprise comparing the level so determined with the level of said expression product in a control sample of cells.

Preferably, the method may comprise determining the level of an expression product of at least two of said genes, preferably at least 3, 4, or 5, and optionally all of said genes.

In a preferred embodiment, the cancer is breast cancer and the method comprises determining the level of expression product in the sample of at least one (preferably at least two or three) of the ch-TOG, SKIN, and TRPC4AP genes.

In another preferred embodiment, the cancer is colon cancer, and the method comprises determining the level of expression product in the sample at least one (preferably at least two or three) of SKIN, SMU-1 and ch-TOG.

In another embodiment, the invention provides a method of providing an indicator for assessment of breast cancer in a patient comprising:
providing an assay sample of tissue obtained from said patient;
determining the level in said sample of an expression product of at least one gene from table 2.

In a still further embodiment, the invention provides a method of providing an indicator for assessment of NSCLC (non small cell lung cancer) in a patient comprising:
providing an assay sample of tissue obtained from said patient;
determining the level in said sample of an expression product of at least one gene from table 3 or table 4.

It may be preferred that the above methods comprise determining the level of an expression product of at least 2, 5, 8, 10, 11, 12 or all of the genes in table 2 or table 3 or table 4, respectively.

The level so determined may be compared with the level of the expression products in a control sample of cells.

In a still further aspect, the invention provides a kit for use in the assessment of cancer, wherein the kit comprises a specific binding partner for the expression product of:
at least one gene selected from DDX21, SF3B1, ch-TOG, SKIN, TRPC4AP and SMU-1, or other gene listed in FIG. 11; or
at least one of ch-TOG, SKIN, and TRPC4AP; or
at least one of SKIN, SMU-1 and ch-TOG; or
at least one gene from table 2; or
at least one gene from table 3 or table 4,
wherein said specific binding partner is immobilised on a solid surface.

The invention also provides a kit for use in the assessment of cancer, wherein the kit comprises a specific binding partner for the expression product of:
at least two genes selected from DDX21, SF3B1, ch-TOG, SKIN, TRPC4AP and SMU-1, or other gene listed in FIG. 11; or
at least two of ch-TOG, SKIN, and TRPC4AP; or
at least two of SKIN, SMU-1 and ch-TOG; or
at least two genes from table 2; or
at least two genes from table 3 or table 4.

Preferred features of the corresponding methods apply equally to the kits, particularly regarding the number of genes whose expression products are detected (e.g., at least 2, 5, 8, 10, 11, 12 or all of the genes in table 2 or table 3 or table 4, or at least two, three, four, five or all of DDX21, SF3B1, ch-TOG, SKIN, TRPC4AP and SMU-1, or other gene listed in FIG. 11).

In a still further aspect, the invention provides use of a specific binding partner of:
a gene selected from DDX21, SF3B1, ch-TOG, SKIN, TRPC4AP and SMU-1, or other gene listed in FIG. 11; or
a gene selected from table 2; or
a gene selected from table 3 or table 4,
in the manufacture of a kit for use in providing an indicator for the assessment of cancer.

In each of the above methods or kits, or in the above use, the gene expression product may be a protein or a transcript. Where the gene expression product is a transcript, the specific binding partner may be a nucleic acid which hybridises to the transcript. In aspects relating to kits, the kit may optionally be a gene chip array, or may be a kit suitable for any other high or low density transcript or protein assay.

The present invention also provides for the use of a protein selected from DDX21, SF3B1, ch-TOG, SKIN, TRPC4AP and SMU-1 or other gene listed in FIG. 11, a protein of table 2, a protein of table 3 and a protein of table 4 for screening for a candidate agent for the treatment of cancer in a patient.

In a still further embodiment, the invention provides a method of screening for a candidate agent for the treatment of cancer in a patient, comprising:
a) providing a protein selected from DDX21, SF3B1, ch-TOG, SKIN, TRPC4AP and SMU-1 or other gene listed in FIG. 11, or a protein of table 2, table 3 or table 4;
b) bringing the protein into contact with a test agent;
c) determining whether said test agent is capable of binding and/or modulating the activity of the protein.

In another aspect, the invention provides a method of screening for a candidate agent for the treatment of cancer in a patient, comprising:
identifying a gene whose expression is modulated in a terminally differentiated mammalian cell in culture by contacting the cell with E1A so as to cause its re-entry into the cell cycle;
providing a protein expressed by the gene;
bringing the protein into contact with a test agent; and
determining whether said test agent is capable of binding and/or modulating the activity of the protein.

Since the class of proteins which are not strongly induced by inactivation of Rb and which are significantly induced by an E1A pocket binding mutant have been identified as one class of protein which are particularly important to naturally occurring tumours, the invention further relates to modulators, and preferably inhibitors, of this class of proteins as candidate therapeutics for the treatment of cancer, and to method of screening for said candidate therapeutics.

Therefore, one embodiment of the above described invention is a method of screening for a candidate agent for the treatment of cancer in a patient, comprising:
identifying a gene whose expression is modulated in a terminally differentiated mammalian cell in culture by contacting the cell with E1A so as to cause its re-entry into the cell cycle, whose expression is not strongly modulated by inactivation of a pocket protein, and whose expression is significantly modulated by an E1A pocket binding mutant;
providing a protein expressed by the gene;
bringing the protein into contact with a test agent; and
determining whether said test agent is capable of binding and/or modulating the activity of the protein.

However, other classes of E1A-induced genes may also be important. In other embodiments, therefore, the gene may be one of the following:
(a) genes whose expression is: strongly modulated, preferably induced, by inactivation of a pocket protein, preferably Rb; not modulated by an E1A pocket binding mutant, particularly the E1A pocket binding mutant YH47; strongly induced by E2F1 overexpression;
(b) genes whose expression is: strongly modulated, preferably induced, by inactivation of a pocket protein, preferably Rb, not modulated by an E1A pocket binding mutant, particularly the E1A pocket binding mutant YH47; not induced by E2F1 overexpression;
(c) genes whose expression is strongly modulated, preferably induced, by inactivation of a pocket protein, preferably Rb; modulated by an E1A pocket binding mutant, particularly the E1A pocket binding mutant YH47; preferably not induced by E2F1 overexpression.

Optionally, the gene may be a gene whose expression is modulated in mammalian (e.g., human) tumours.

The invention also provides a method of screening for a candidate agent for the treatment of cancer in a patient, wherein said method comprises
 a) providing a transformed cell in culture;
 b) bringing said cell into contact with a test agent; and
 c) determining whether said test agent is capable of modulating the level of a transcript selected from DDX21, SF3B1, ch-TOG, SKIN, TRPC4AP and SMU-1 or other transcript listed in FIG. 11, or a transcript of table 2, table 3 or table 4.

In a still further aspect, the invention provides a method of screening for a candidate agent for the treatment of cancer in a patient, comprising:
 identifying a gene whose expression is modulated in a terminally differentiated mammalian cell in culture by contacting the cell E1A so as to cause its re-entry into the cell cycle;
 providing a transformed cell in culture:
 bringing said cell into contact with a test agent; and
 determining whether said test agent is capable of modulating the level of the transcript of said gene.

In a preferred embodiment, the invention provides a method of screening for a candidate agent for the treatment of cancer in a patient, comprising:
 identifying a gene whose expression is modulated in a terminally differentiated mammalian cell in culture by contacting the cell E1A so as to cause its re-entry into the cell cycle, whose expression is not strongly modulated by inactivation of a pocket protein, and whose expression is significantly modulated by an E1A pocket binding mutant;
 providing a transformed cell in culture:
 bringing said cell into contact with a test agent; and
 determining whether said test agent is capable of modulating the level of the transcript of said gene.

Optionally, the gene may be a gene whose expression is modulated in mammalian (e.g., human) tumours.

In another aspect, the invention provides the use of an agent obtainable in one of the above screening methods for the manufacture of a medicament for the treatment of cancer.

In all of the above aspects relating to genes or proteins of table 2, table 3 or table 4 (kits, screening methods and uses), where the gene/protein is a gene/protein of table 2 then the cancer is preferably breast cancer. Where the gene/protein is a gene/protein of table 3 or table 4 then the cancer is preferably NSCLC.

In a still further aspect the invention provides the use of an inhibitor of SKIN activity or expression for the treatment of cancer in a patient.

Prognosis or treatment of cancer may be applied to, for example, melanoma, or cancer of the breast, colon, kidney, larynx, lung, prostate, stomach, uterus or brain.

The invention will now be described in detail, and with reference to the following drawings:

FIG. 1.
FIG. 1 shows Numb expression in human mammary tumours.
1a) The typical immunoreactivity for Numb in normal breast (normal) showed intense staining in the vast majority of ductal (luminal) and lobular epithelial cells, with a prominent membranous staining pattern. Examples are shown of typical class-1 (type-0), class-2 and class-3 tumours. Arrowheads point to normal glands that are intensely stained within the context of the tumours. Original magnification, ×100.
1b) In situ hybridisation with an anti-sense probe for Numb mRNA was performed on paraffin sections. Control hybridizations with a corresponding sense probe gave no signal (not shown). Examples of matching bright fields (top) and dark fields (bottom) of typical class-1 (left) and class-3 (right) tumours are shown. Numb transcripts appear as bright pots in the dark fields (bottom). Original magnification, ×200.

FIG. 2.
a) Primary matched normal (top) and tumour (bottom) mammary cells, from class-1 (right) and class-3 (left) patients were treated with MG132 (+) for 12 h, or mock-treated (−), and stained with anti-Numb. Original magnification, ×63.
b) Total cellular lysates from the same cells as in (a) were immunoblotted with anti-Numb (top). Molecular mass markers are indicated in KDa, on the right. Typically, two Numb-specific bands (each probably corresponding to a tightly-spaced doublet) are detected in human mammary cells. Equal loading was checked by reprobing with anti-actin (bottom).
c) Primary tumour mammary cells were either mock-treated (−) or exposed to MG132 (+) for 12 hours, as indicated. Lysates were immunoblotted (WB) with the indicated antibodies.
d) Tumour mammary cells from class-1 and class-3 patients were either mock-treated (−) or exposed to MG132 (+) for 6 h, as indicated. Lysates were immunoprecipitated (IP) with a monoclonal anti-Numb antibody and immunoblotted (WB) with the indicated antibodies. Molecular mass markers are indicated in KDa, on the right.

Results in all panels are representative of three independent experiments. In addition, similar results were obtained with primary cultures from three class-1 (type-0) and three class-3 patients (not shown).

FIG. 3.
a) Primary mammary tumour cells from class-1 (type-0) (left) and class-3 (right) patients were transduced with retroviruses encoding GFP or a Numb-GFP fusion protein, as described in Methods. After three weeks, plates were fixed and stained (bottom) to count colonies. The bar graph on the top shows the average colonies (colony forming units±SD) in triplicate plates. Results are representative of three independent experiments. In addition, similar results were obtained with primary cultures from three class-1 (type-0) and three class-3 patients (not shown).
b,c) The expression of GFP and Numb-GFP proteins, as detected by epifluorescence (b) or immunoblot (c), upon transient retroviral delivery of the transgenes is shown, to demonstrate equal efficiency of infection/expression.

FIG. 4.
a) Primary tumour mammary cells from class-1 (type-0) (top) and class-3 (bottom) patients were treated with MG132 (+), or mock-treated (−) for 1h, and stained with anti-Notch. Original magnification, ×40. Note the lower basal levels of Notch expression in class-1, in MG132-untreated cells, and the presence of nuclear Notch in the same class, upon MG132 treatment.
b) CBF1-responsive reporter gene activity was evaluated in normal and tumour mammary cells from class-1 (type-0) and class-3 patients, as described in Materials and Methods.
c) HES-1 mRNA expression in total RNAs from normal and tumour mammary cells from class-1 (type-0) and class-3 patients.

In (b) and (c) the mean fold induction (± SD) from two independent experiments performed in triplicate is shown. In all panels, results are representative of those obtained with primary cultures from three class-1 (type-0) and three class-3 patients (not shown).

FIG. 5.
a) Primary normal (left) or tumour (right) mammary cells were transfected with siRNA oligos for Numb or control (ctr) oligos for 72 h, and assayed for HES-1 mRNA expression levels (bar graphs) or immunoblotting with the indicated Ab (WB).
b) Primary tumour mammary cells from class-1 (type-0) and class-3 patients were transduced with GFP or Numb-GFP and assayed for HES-1 mRNA expression levels 72 h post-infection (protein expression controls are as from FIG. 3b, not shown here). Normal primary cells from the same patients behaved as class-3 tumours, as expected (not shown). In (a) and (b) the mean fold induction (±SD) from two independent experiments performed in triplicate is shown.
c) Primary mammary tumour cells from class-1 (type-0) (left) and class-3 (right) patients were treated with the γ-secretase inhibitor DFP-AA for 10 days, or mock-treated (ctr), followed by staining (bottom) to count colonies. The bar graph on the top shows the average colonies (colony forming units±SD) in triplicate plates. Results are representative of three independent experiments.
d) HES-1 mRNA expression from cells treated as in (a), the mean fold induction (±SD) from two independent experiments performed in triplicate is shown.
In all panels, results are representative of those obtained with primary cultures from three class-1 (type-0) and three class-3 patients (not shown).

FIG. 10 shows genes induced by E1A, and the results of RTQ-PCR in E1A (dl520) infected TD C2C12 myotubes, proliferating (MYB) C2C12 myoblasts, E1A (dl520) infected TD MSC (mouse satellite cells) and proliferating (MYB) MSC myoblasts. The first column gives the mouse accession number. The second column gives the name and description in mouse. The fourth column gives the accession number of the human sequence.

FIG. 11 shows E1A induced genes allocated to classes A, B, C or D according to their mechanism of regulation. The columns show the ratio of induction under the named conditions with induction with wild type E1A. The column headed "Ratio 24 h/36 h" shows the ratio of induction at 24 h and 36 h.

FIG. 12.
12a shows the percentage of positive tumour samples the named genes in different tissues.

FIG. 12b shows bright field and dark field microscope analysis showing the specific signal from the cancer cells of tumour samples (T) compared to a matched normal counterpart (N). FIG. 12c shows a cell cycle plot of relative mRNA levels of 4 E1A induced genes in G0 synchronized serum starved NIH 3T3 cells stimulated by serum addition and HeLa cells released after nocodazole induced G2/M arrest. Almost all the class D genes are not cell cycle regulated in both serum response dependent and independent manner, while all the class A and B genes are cell cycle regulated and the class C genes marginally cell cycle regulated. ClassA-XTP1 (filled squares); classB-MGC22679 (empty squares); classD-TRPC4AP (empty circles); classD-SKIN (filled circles).

Figure 13:
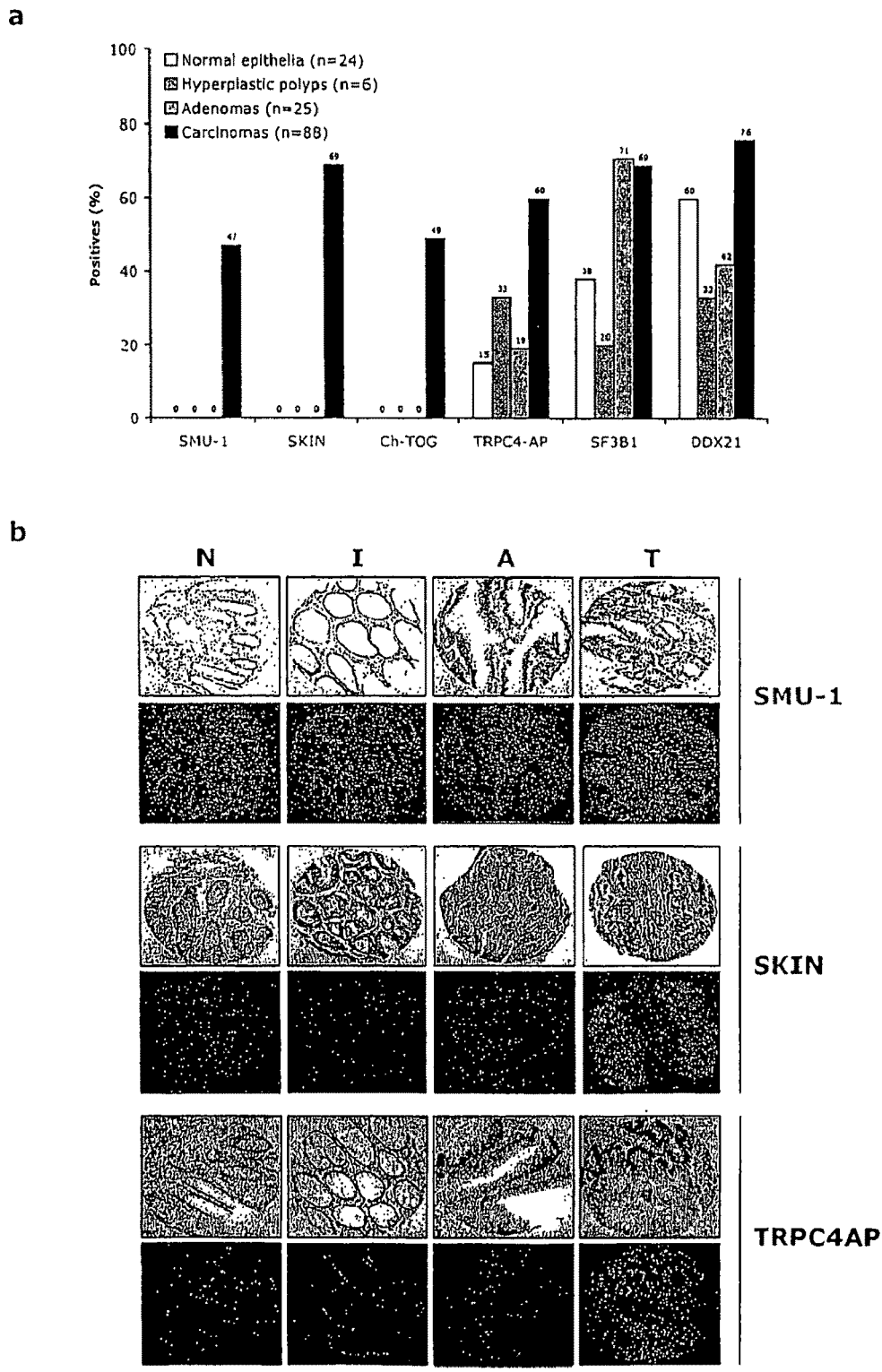

FIG. 13.
A) All the six class D genes result strongly overexpressed in tumours (47% to 76%) of colon cancer progression by in situ hybridization on colon specific tissue microarrays (TMA) (N=normal epithelia, I=hyperplastic polyps, A=adenomas T=adenocarcinomas).
The number on top of each column indicates the percentage of positive samples. Numbers in brackets represent the total samples tested for each stage of the progression.
B) Bright field and dark field microscope analysis matches the probe signal to the correspondent histological section.

Figure 14:
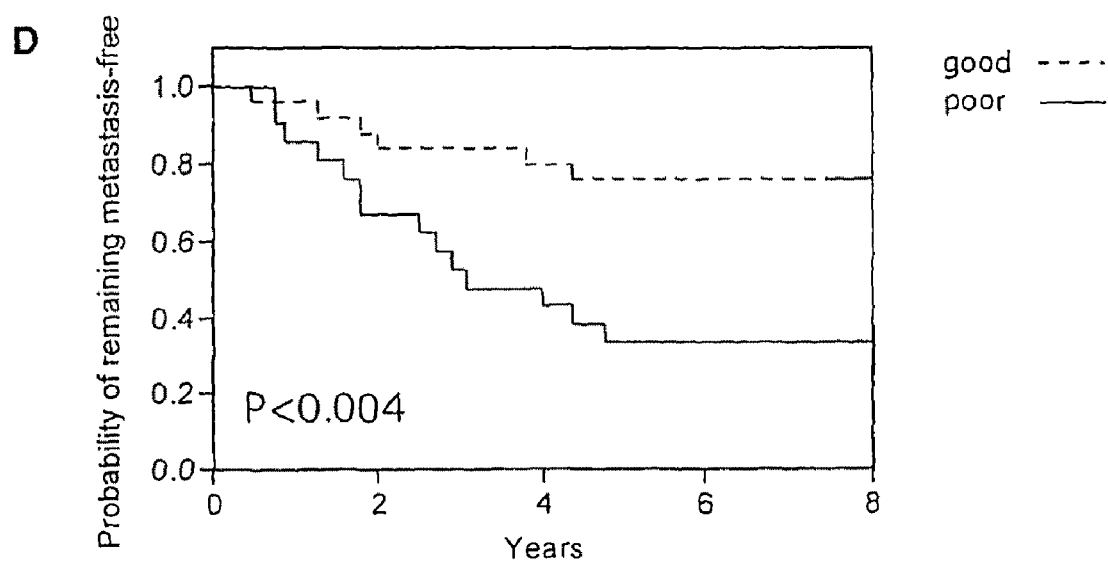

FIG. 14.
FIGS. 14 A-C show that selected class D genes predict disease outcome in breast cancer.
Three class-D genes (SKIN, TRPC4AP and Ch-TOG) were used together as a predictor of prognostic outcome on two independent data sets, one generated by the inventors (A) and another from van't Veer (42) (B). Data are shown as the probability of remaining free of metastatic relapse, in a Kaplan-Meier plot, as a function of a "favourable" (dashed line), or "unfavourable" (continuous line) signature. (C). Q-RT-PCR analysis of the three predictive class-D genes was performed on 15 randomly selected breast tumour patients (all lymph node negative at diagnosis), which were all homogeneous for estrogen receptor status (ER pos). Five were N0 patients (5-years disease-free patients) and 15 were N0+ patients (patients relapsed with metastatic disease within 5 years). Q-RT-PCR values were normalized to patient 1 (assumed as 1.0). A 50th percentile value was then established for each gene and a matrix was built based on the 50th percentile value, by assigning scores of 0 or 1 to values below of above the threshold, respectively. The sum of the two matrix scores was then used to assign "favourable" (score 0-1) or unfavourable (score 2-3) labels. Probability of remaining metastasis free is shown in the Kaplan-Meier plot as a function of the presence of the "favourable" (dashed line), or "unfavourable" (continuous line) signature. In A-C, the p-values were calculated with the log-rank test.

FIG. 14D shows the probability of remaining free of distant metastasis for a patient having a good or bad prognosis based on the Class A, B and C genes predictor.
Class A, B and C were used together as a predictor of prognostic outcome on a subgroup of breast tumours with no lymph nodes involvement at surgery, which either developed metastatic disease (N0+ patients) or stayed disease-free (N0- patients) over a 5 year follow up period analysed by Affymetrix.

Figure 15:
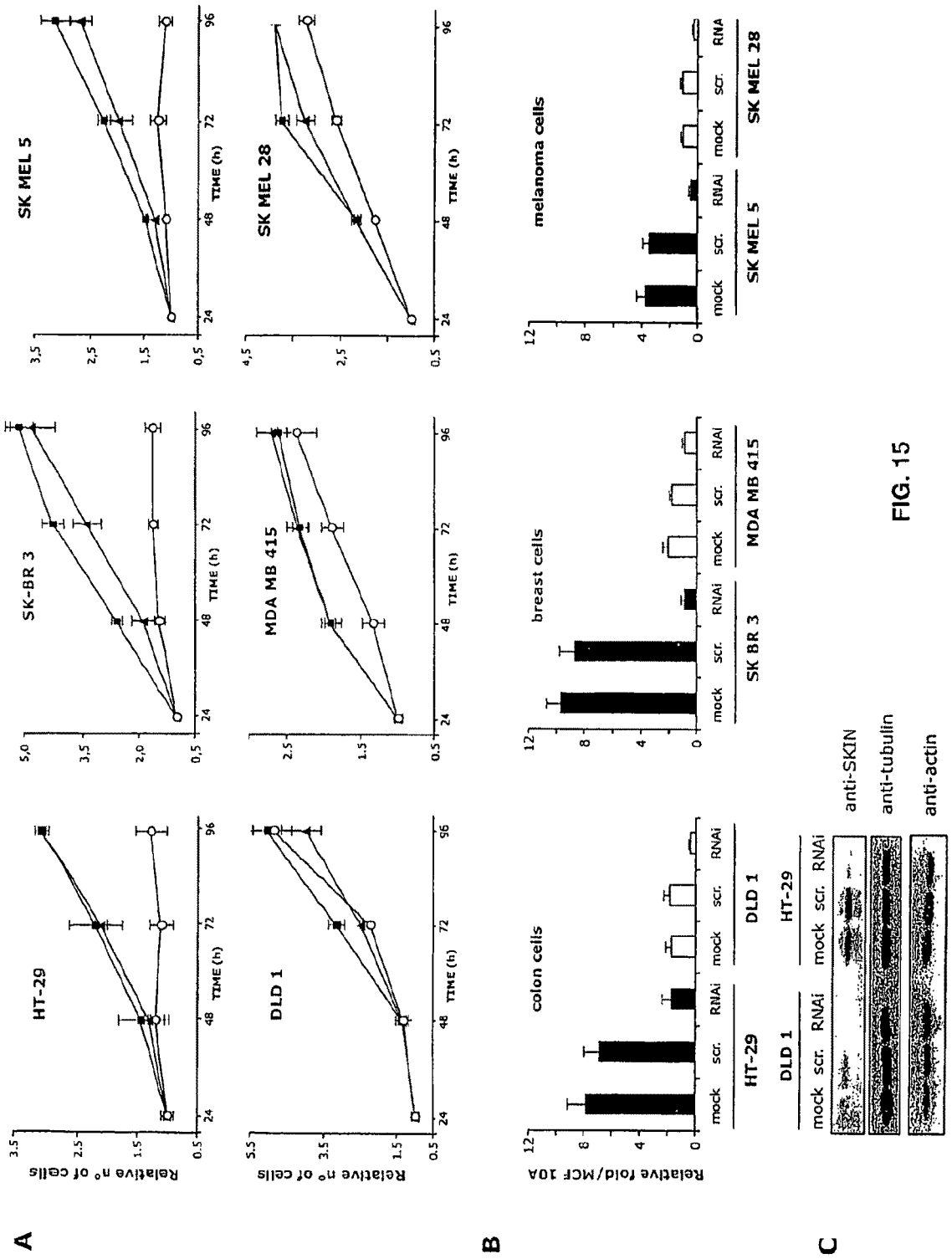

FIG. 15.
SKIN knock down by siRNA reduces proliferation in different tumour cell lines.
Six different tumour cell lines (as indicated) were treated with SKIN-specific siRNA (empty circles in A; RNAi in B and C), or a control scrambled oligo (filled triangles in A; scr. in B and C) or mock-treated (filled squares in A; mock in B and C). Twenty-four hours after treatment, cells were re-plated to measure cell growth (A), or analyzed for SKIN transcript levels by Q-RT-PCR (B). A. Cells, re-plated in standard growth medium, were counted at the indicated time points. Data are expressed relative to the number of cells present in the plate 24 h after re-plating (assumed as 1). B. Q-RT-PCR data are expressed relative to those detected in growing MCF10A cells, to allow for comparison among cell lines. C. In the case of DLD1 and HT-29 cells, levels of SKIN were also measured by Western Blot with an anti-SKIN antibody.

FIG. 16 shows the results of an ONCOMINE analysis of Class-D genes. The genes which pass the statistical filter (p-value <0.05 with Bonferroni correction) are shown together with their log2 median value in every class considered, where: "N" stands for normal samples; "T" for primary tumours and "M" for distant metastasis.

Figure 17:
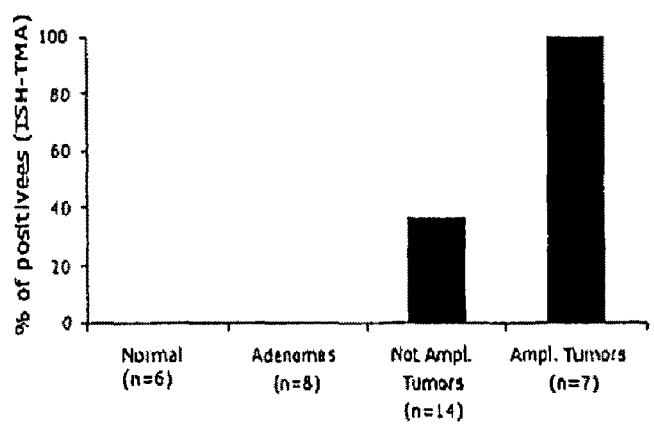

FIG. 17 shows that SKIN is amplified in colon cancers.

A. Summary of amplification data obtained by FISH analysis of metaphase-blocked tumour cell lines with MCF10A (normal human epithelial cells) as control: "RNA level", SKIN transcripts measured by Q-RT-PCR and normalized to values in MCF10A cells; "copies", number of signals with the SKIN RP11-1139F3 probe; "chr. 8", number of signals with the 8q RP11-103I1 probe; "ploidy", ratio between SKIN signals and chr. 8 signals. In the column "copies", additional features are marked as follows: *, tandem repeats; $, extra-chromosomal copies, #, hsr (homogenously stained region).

B. Graphical representation of results obtained by FISH analysis of human colon cancer specimens of SKIN and chromosome 8. The average number of SKIN signals/cells was counted, and normalized to the number of signals with chr.8 probe. Samples were considered amplified if >50% of the epithelial cells presented >4 signals/cell. Examples are shown: N, normal epithelium (copies/cell=2); tumour not amplified (copies/cell <4); tumour amplified (copies/cell>4). The bar graph shows the % of SKIN-overexpressing samples (evaluated by ISH) in various colon specimens (n, number of analyzed samples).

Figure 18:
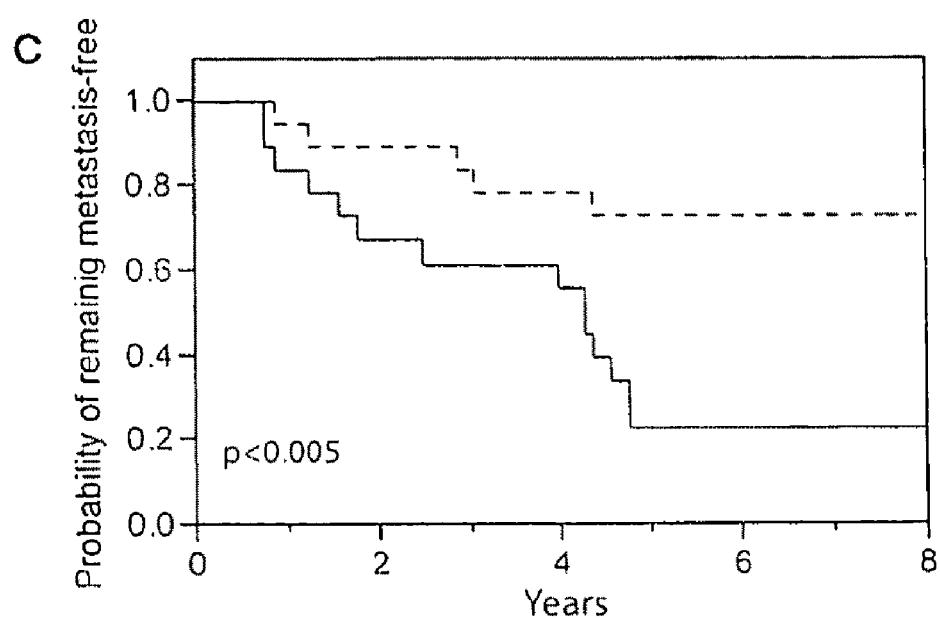

FIG. 18A shows the probability of remaining metastasis-free of patients with a good (dashed line) or poor (solid line) expression signature based on the inventor's breast cancer predictor (13 genes). P-values were calculated with the log-rank test.

FIG. 18B shows the probability of remaining metastasis-free of patients with a good (dashed line) or poor (solid line) expression signature based on the predictor of Van't Veer L J (Nature 415(31), 530-535 (2002)). P-values were calculated with the log-rank test.

FIG. 18C shows the probability of remaining metastasis-free of patients with a good (dashed line) or poor (solid line) expression signature based on the inventor's breast cancer predictor (13 genes) using Q-RT-PCR validation. P-values were calculated with the log-rank test.

Figure 19:
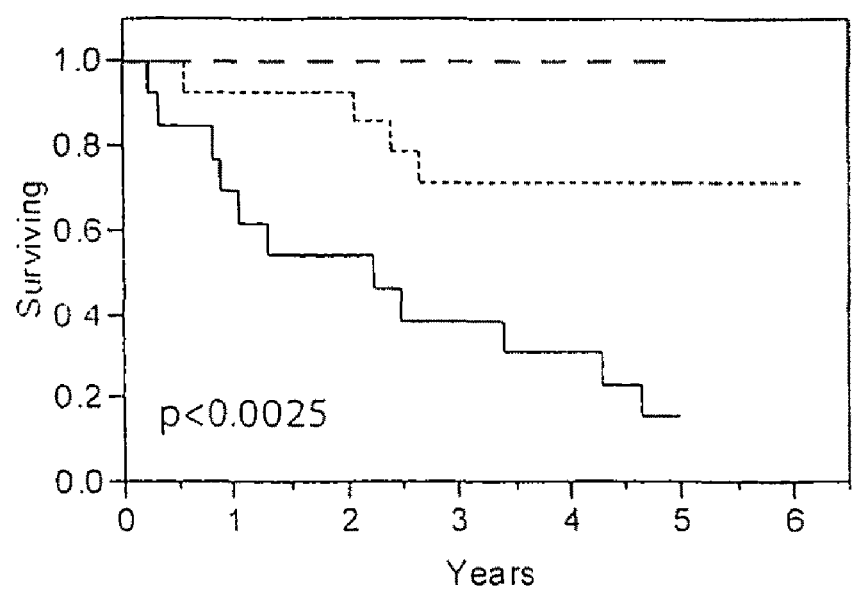
Figure 19:
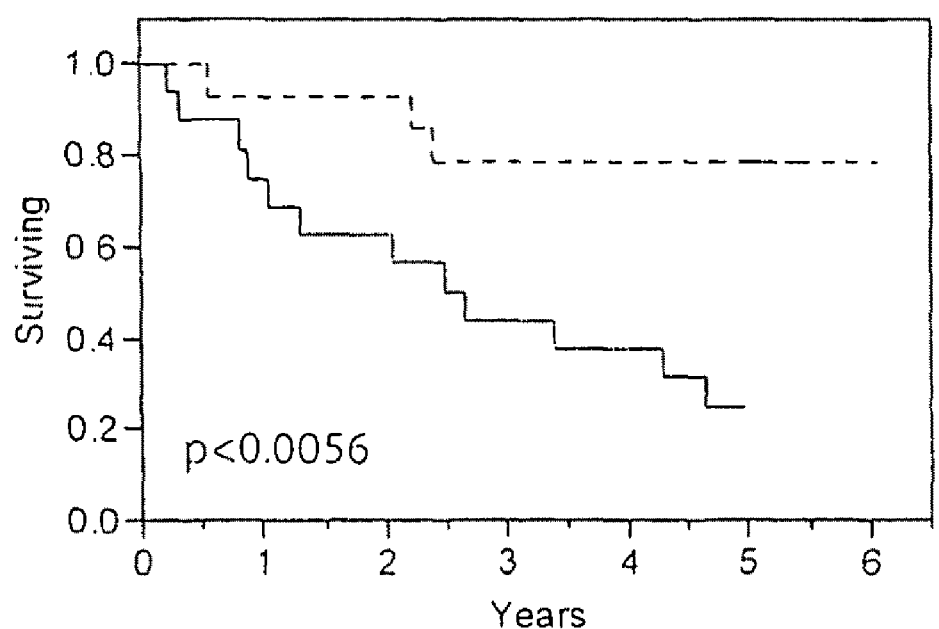

FIG. 19 shows the probability of remaining metastasis-free of patients with a good (dashed line) or poor (solid line) expression signature based on the inventor's NSCLC predictor (12 and 21 genes). P-values were calculated with the log-rank test. FIG. 19A shows the results for the 12 gene predictor for the dataset of Beer et al., and FIG. 19B shows the results for the 12 gene predictor for the dataset of Bhattachargee et al. FIG. 19C shows the results of Q-RT-PCr analysis of the 12 genes predictor performed on an independent set of 30 patients, all with stage I NSCLC adenocarcinomas. Wide dashed line=undetermined. FIG. 19D shows the results of Q-RT-PCR analysis of the 21 genes predictor performed on an independent set of 30 patients, all with stage I NSCLC adenocarcinomas.

DETAILED DESCRIPTION OF THE INVENTION

References to Numb herein are to a mammalian Numb, and preferably human Numb, unless otherwise clear from the context. The sequence for human Numb mRNA is given in ACC. NO NM_003744.

When Notch is referred to herein, it is meant any one of mammalian (preferably human) Notch 1, 2, 3 or 4 (ACC. NO NM_017617, NM_024408, NM_000435, NM_004557) and preferably Notch 1 and 4.

DDX21 is Deadbox polypeptide 21. SF3B1 is splicing factor 3b, subunit 1. Ch-TOG is colonic and hepatic tumour overexpressed protein and is also known as KIAA097. SKIN (similar to KIAA0493 induced in tumour) is a protein having no previously attributed function. TRPC4AP is the transient receptor potential cation channel, subfamily C, member 4 associated protein, and is also known as RRIP. SMU-1 is the Suppressor of MEC-8 and UNC-52 homolog. FIG. 10 provides the accession number for the human and mouse sequences, but reference to the gene or protein may include other mammalian sequences. The short names used herein are, for convenience, the names of the human homolog, but this is not intended to exclude other mammalian homologs. FIG. 11 provides the accession numbers for the four classes of E1A-induced genes.

Tables 2, 3 and 4 provide accession numbers for the genes therein. Reference to the gene or protein may include other mammalian sequences.

Accession numbers for mRNA sequences are given above, but genes transcripts or proteins may be referred to, as will be apparent from the context.

A patient as referred to herein is a mammalian patient and more preferably a human.

Assessment of Cancer in a Patient

An assessment of cancer in a patient as referred to herein may be diagnosis or prognosis of the cancer.

Assessment of cancer can comprise assessment of a suitable clinical option for the cancer. For example, the level of the gene expression product(s) examined may indicate an appropriate level of aggression in the treatment regime. Assessment can also comprise assessment of the response of the cancer to treatment.

In some aspects and embodiments above, assessment of the cancer may be assessment of the susceptibility of a cancer to treatment with an inhibitor of Notch, as described in more detail below.

An indicator for assessment of a cancer refers to a result (i.e., to data) which can be used in assessing the cancer, e.g., together with other information.

The method may also comprise comparing the protein status or level of one or more expression products to that of a control sample, as explained in more detail below. When the control sample is a sample of normal cells or a sample of tumour cells having good prognosis (e.g., non-metastatic tumour cells), then a poor prognosis may be suggested by a gene status or by a level of a gene expression product which is divergent from the level in the control. When the control is associated with poor prognosis, e.g., is a sample from a metastatic tumour, then poor prognosis may be suggested by gene status or a level of gene expression products which is in line with or similar to the control sample. Of course, as explained below, more than one control may be used.

In respect of the genes of table 2 in breast cancer, upregulation of expression of one or more genes in the tumour (e.g., relative to other breast tumours associated with good prognosis and particularly non-metastatic tumours) may be associated with a worsening of the prognosis.

In respect of the genes of table 3 in NSCLC, downregulation of HLA-DQB1, LU, GNS, POLR2C, PBXIP1 and RAFTLIN, e.g., relative to a tissue type having good prognosis such as non-metastatic tissue, and upregulation of PAICS, PFN2, SERPINB5, HSPD1, E2F4 and ARL4A relative to a tissue type having a good prognosis, may be associated with a worsening of the prognosis.

In respect of the genes of table 4 in NSCLC, downregulation of HLA-DQB1, and RAFTLIN, e.g., relative to a tissue type having good prognosis such as non-metastatic tissue, and upregulation of PFN2, SERPINB5, E2F4, E2F1, MCM7, RRM2, MCM4, MCM6, CML66, SF3B1, ATP13A3, CXCL6, GABPB2, GAPDH, GARS, HOXB7, HSPG2, KIAA0186, SCGB3A1 relative to a tissue type having a good prognosis, may be associated with a worsening of the prognosis.

In the present application, it will be understood that providing a sample of tissue obtained from a patient and determining protein status of the sample is reference to an in vitro method practiced on a sample after removal from the body.

Determining Protein Status

In some aspects, the method comprises determining the status of Numb and/or other proteins associated with diagnosis or prognosis of the cancer.

By determining the status of a protein is meant any determination (in some embodiments a quantitative determination) which directly or indirectly indicates the activity level of the protein in the tissue, for example, status may be determined by: determining the presence of mutations in the nucleic acid or protein sequence, determining the copy number of a DNA sequence in the cell, determining the level of a gene expression product such as a protein or transcript, or directly measuring protein activity.

With regard to Numb, it is preferable that the determination comprises determining protein level as described further below. The inventors have found that whereas normal tissue shows intense and homogenous Numb staining, tumours display marked heterogeneity. Therefore, a preferred way of measuring the level of Numb protein in the sample may be to assess the proportion of cells which show positive labelling for Numb.

P53 status may be preferably assessed by immunohistochemical analysis using well known methods. As mentioned above, p53 positively is an indication that the p53 is mutated and hence is inactive. In other embodiments, it may be preferred that P53 status is assessed by sequencing, to identify the presence of the mutation.

Estrogen receptor status may be preferably assessed by detecting the level of protein in the sample, e.g., by immunohistochemical analysis.

Determining Notch Activity

Determination of Notch activity can be made for example by assessing the level of a protein or transcript whose expression is regulated by Notch. A preferred example is HES-1.

Inhibitors of Notch Signalling

Preferably, an inhibitor of Notch signalling results in a reduction in the level or activity of Notch protein.

In some embodiments, it may be preferred that the inhibitor is an agent which restores (at least partially) Numb activity. For instance, the inhibitor may be a Numb polypeptide, or a Numb polypeptide modified so as to be resistant to ubiquitination (e.g., lacking a necessary phosphorylation site). In some embodiments, the inhibitor may be a nucleic acid encoding one of these polypeptides. The inhibitor may also be an agent which prevents targeting of Numb for ubiquitination. It has been suggested that Numb levels may be regulated by E3 ligases, such as LNX, Siah-1 and Mdm2[14, 26, 27]. It has also been found that in *Drosophila* a serine/threonine kinase NAK physically interacts with Numb and causes loss-of-Numb phenotypes on overexpression[30]. Therefore an inhibitor may be an agent which blocks the binding of a kinase (e.g., a NAK homolog) or E3-type ubiquitin ligase (e.g., LNX, Siah-1 or Mdm2) to Numb, or which inhibits the activity of the kinase or ligase thereon. The agent may for example be an antibody (against Numb or the kinase or E3-type ubiquitin ligase), small molecule, or a polypeptide fragment of Numb, said kinase or E3-type ligase.

A Numb polypeptide for use as a therapeutic, or which is encoded by a nucleic acid for use as a therapeutic, may be a polypeptide having at least 70% amino acid sequence identity to the sequence given in AAD54279.1, more preferably 80%, 90%, 95% or 99%, and fragments thereof, wherein the proteins and fragments thereof retain the ability to inhibit Notch activity. Fragments may comprises at least 10, more preferably at least 20, 30, 40 or 50 consecutive amino acids of a mammalian Numb sequence.

In other embodiments, the inhibitor is preferably an inhibitor other than a factor which restores Numb level. For example, the inhibitor may be an inhibitor of Notch, e.g., an agent which binds Notch such as an antibody against Notch, or a nucleic acid inhibitor of Notch such as an antisense nucleic acid, siRNA, or ribozyme. SiRNA may be a short double stranded RNA molecules which are sequence specific for a gene transcript, or a longer RNA sequence which can be processed by the cell into siRNA, and which can be provided to the cell e.g., as a DNA sequence (eliRNA, or expressed long interfering RNA).

An example of an antisense nucleic acid which the inventors have used to inhibit Notch is:

(SEQ ID NO: 1)
AACAGCCCACTGAACAAGCAGA.

In addition, small molecule inhibitors may be used.

Upon receptor-ligand interaction, Notch proteins are cleaved by a presenilin-1 (PS-1) dependent γ-secretase activity. This releases a cytoplasmic subunit which migrates to the nucleus and regulates the expression of several transcription factors.

Accordingly, the inhibitor may also target presenilin-1 or, more preferably, the presenilin-1 (PS-1) dependent γ-secretase activity. For example, it may be an antibody against these proteins, a polypeptide fragment of these proteins, a nucleic acid inhibitor of these proteins, as discussed above, or a small molecule inhibitor of this protein.

A known small molecule inhibitor of Numb signalling is DFP-AA, a peptidomimetic presenilin-inhibitor.

A known inhibitor of γ-secretase is GSI.

Mimetics of modulators identified in the screen may be identified using any of the methods known in the art, and as described in more detail below.

Methods of Screening for Inhibitors of Numb Degradation

In one aspect, the invention relates to a method of screening for a candidate agent for the treatment of cancer in a patient, comprising:
  providing a test system comprising a Numb polypeptide and an enzyme capable of targeting Numb for degradation;
  contacting said test system with a test agent; and
  assessing the ability of the test agent to inhibit the targeting of Numb for degradation.

Targeting of Numb for degradation includes any enzyme action on Numb which increases the rate at which Numb is degraded when present in a cell.

The test system may be an in vitro test system, e.g., in some embodiments it is an in vitro test system which comprises the components required for targeting Numb for degradation. For example, in some embodiments the test system may comprise free ubiquitin. Alternatively, the test system may be a cell, preferably a mammalian cell and more preferably a human cell.

The test is preferably carried out under conditions where Numb is targeting for degradation, e.g., is ubiquitinated, in the absence of the test agent. For example, where the test system is a cell, the cell may be a transformed cell, e.g., a breast cancer cell. The cell may be a cell in which Numb levels are reduced relative to a control sample, e.g., relative to a normal tissue from the same patient.

The Numb polypeptide may be labelled, e.g., with a histidine tag to allow its isolation.

The Numb polypeptide for use in the screening method may be a mammalian Numb protein, preferably a human Numb protein, and may also be a fragment or variant of said protein which can be specifically recognised and targeted for degradation.

Fragments may comprises at least 10, more preferably at least 20, 30, 40 or 50 consecutive amino acids of a mammalian Numb sequence. A variant may have at least 70%, 80%, 90%, 95% or 99% identity to a full length mammalian Numb sequence, preferably to the human sequence, assessed over the full length of the mammalian Numb sequence.

The percentage identity of amino acid sequences can be calculated using commercially available algorithms. The following programs (provided by the National Center for Biotechnology Information) may be used to determine homologies: BLAST, gapped BLAST, BLASTN and PSI-BLAST, which may be used with default parameters.

The test agent or candidate compound may be any of the candidate compounds described below in relation to assay methods. The test agent may for example be a fragment of the Numb protein (e.g., a fragment which is competes with Numb for recognition by the enzyme), an antibody that binds specifically to Numb or to an enzyme responsible for targeting Numb for degradation, or a small molecule (a natural or synthetic chemical compound). Where the test system is a cell, the agent may also be an agent which blocks the expression of said enzyme, such as an antisense sequence, siRNA or ribozyme.

Agents identified in the screen can be used to design mimetics or may be used in methods of treating cancer in a patient, as described below.

The enzyme capable of targeting Numb for degradation may for example be an enzyme which modifies Numb such that it is subsequently recognised by an ubiquitin-conjugating enzyme, or it may be an ubiquitin-conjugating enzyme. For example, the enzyme may be a kinase or phosphorylase, and may particularly be a mammalian homolog of the *Drosophila* serine/threonine kinase NAK. In other embodiments, it may be an E3 ligase, e.g., LNX, Siah-1 or Mdm2.

The ability of the test agent to inhibit the targeting of Numb for degradation may be assessed using any appropriate method. For example, the method may comprise determining the modification of the Numb protein, e.g., determining the phosphorylation state of the Numb polypeptide. Alternatively or additionally, the method may comprise determining the ubiquitination state of the Numb polypeptide, e.g., so as to determine the ability of the test agent to inhibit Numb ubiquitination.

The ubiquitination state of the Numb polypeptide may be assessed by assessing the molecular weight of the Numb polypeptide. Another method of assessing the ubiquitination state of the Numb polypeptide is to immunoprecipitate the Numb polypeptide and then to perform immunoblotting with antibodies against ubiquitin.

Genes Modulated in Re-entry to the Cell Cycle

In one aspect, the invention provides a method of selecting a specific binding partner of a gene expression product for use in providing an indicator for the assessment of cancer, the method comprising identifying a gene a) whose expression is modulated (e.g., induced) by contacting a terminally differentiated cell in culture with an agent which causes the cell to re-enter the cell cycle, preferably with an E1A protein; and b) which has modulated (e.g., enhanced) expression in a mammalian, e.g., human tumour;

and selecting for use in a method of assessment of cancer a specific binding partner for an expression product of said gene.

In one embodiment, the method comprises identifying a gene:

whose expression is modulated (e.g., induced) by contacting a terminally differentiated cell in culture with an agent which causes the cell to re-enter the cell cycle, preferably with an E1A protein;

and selecting for use in a method of assessment of cancer a specific binding partner for an expression product of said gene.

The terminally differentiated cell may be a mammalian cell, and is more preferably a primate or rodent cell, e.g., a human cell or mouse cell.

Terminally differentiated cells include terminally differentiated myotubules, neurons and adipocytes.

The method may comprise contacting said cell with an agent which causes re-entry of the cell into the cell cycle, and identifying at least one gene whose expression is modulated in response. The agent which causes the re-entry into the cell cycle may be a viral protein (i.e., a protein encoded by the viral genome) or may be a non-viral, e.g., a mammalian protein. The cell can be contacted with the protein according to any of the methods known in the art, for example, by transformation of the cell with a nucleic acid encoding the protein. Particularly where the protein is encoded by the viral genome, the method may include infecting the cell with a virus comprising a nucleic acid sequence encoding the agent capable of causing re-entry into the cell cycle (e.g., with an adenovirus, papilloma virus or SV40), for example contacting the cell with an adenovirus which comprises a nucleic acid sequence encoding an E1A protein.

The modulation of gene expression in a cell contacted with an agent capable of causing re-entry into the cell cycle, and/or in a human tumour, may be determined by any of the methods known in the art, for example, by a cDNA subtraction approach, or by gene profiling studies, e.g., using the Affymetrix GeneChip technology. Appropriate controls will be employed as apparent to those skilled in the art.

It may be preferred that more than two genes are identified, optionally more than 3, 4, 5, 6, 7, 8, 9, or 10 genes, and that a specific binding partner is selected for the expression product of each of said genes.

In some embodiments, the method includes further steps prior to selection of the specific binding partner. For example, the method may comprise identifying a plurality of genes induced by the factor capable of causing re-entry into the cell cycle, and from these selecting: those genes whose expression is modulated in human tumours by the greatest factor, for example, those whose expression is modulated by at least 1.5 or 2 fold and/or those genes which correlate most strongly with the prognosis in the patient, e.g., using statistical algorithms such as the leave-one-out cross validation method.

Reference to E1A is intended to be reference to any adenoviral E1A expression product capable of inducing re-entry of a terminally differentiated cell into the cell cycle. Preferably, it refers to the E1A 12S mRNA product (which is the short splicing variant), or to a fragment or variant thereof which retains the biological activity.

Preferably, the method comprises identifying genes whose expression is modulated over a time course concomitant to the re-entry of the cell into the cell cycle. For example, the method may comprise identifying genes whose expression is modulated within 24-72 hours of contact with the agent which causes cell-cycle re-entry, and preferably which are modulated within 36 hours. Preferred genes may be those which are late modulated (e.g., late induced), e.g., whose expression is modulated to a greater degree between 24 and 36 hours than at 24 hours. Preferred genes may be those which have a ratio between the fold induction (e.g., of transcript) at 24 hours and at 36 hours of less than 0.4.

The inventors have found that using such methods on a gene set which has first been pre-selected based on E1A modulation, a good predictor of risk of cancer progression (e.g., death or metastasis) can be produced.

In some embodiments the method comprises identifying two genes which belong to the same signalling pathway.

For example, this may comprise determining whether the genes share dependence or independence on at least one factor known to be involved in signalling downstream of the agent which causes cell cycle re-entry. Where the agent which causes cell-cycle re-entry is E1A, then preferably, this factor is a pocket protein, such as RB (the retinoblastoma tumour suppressor gene product).

The pocket proteins are p105, p107 and p130 (RB), which regulate E2F-family members via a domain called a "pocket domain" (Ferreira et al 1998).

An E1A pocket binding mutant is a mutant version of E1A which is unable to bind pocket proteins.

The method may in some embodiments comprise activating or inactivating the factor, e.g., the pocket protein. Inactivation may be by siRNA or antisense inhibition, optionally by inducible siRNA or antisense inhibition, by the use of a specific inhibitor of the protein such as an antibody, or by the use of CRE recombinase. Activation may be by overexpression of the protein, e.g., from a vector.

In various aspects and embodiments of the present invention, gene or genes are referred to whose expression is not strongly modulated by inactivation of a pocket protein, e.g., RB, and whose expression is significantly modulated by an E1A pocket binding mutant. Genes belonging to this class may be preferred in aspects and embodiments of the invention.

"Strongly modulated" preferably refers to modulation which is at least 60% of that observed using wild type E1A. (Hence, "not strongly modulated" preferably refers to modulation which is less that 60% of that observed using wild type E1A). "Significant modulation" and "significantly modulated" preferably refers to modulation which is at least 40% of that observed using wild type E1A, and hence "not significantly modulated" refers to modulation which is less than 40% of that observed using wild type E1A.

Whether a gene is strongly modulated or significantly modulated can be determined by comparing the level of modulation under those conditions with the level of modulation by E1A (e.g., as defined above). Whether a gene is late or early regulated can be assessed by comparing its modulation level at 24 h with its modulation level at 36 h. This comparison can be expressed as a modulation ratio, of the fold modulation of the gene. While methods of measuring this ratio will be apparent to the skilled person, exemplary conditions may be as follows:

Modulation may be ascertained in TD mouse myotubules. Modulation may be measured by measuring transcript levels, e.g., using Q-RT-PCR.

The cells may be transfected with an adenovirus expression only the 12S mRNA of E1A, such as the adenovirus dl520, to ascertain the level of modulation caused by wild type E1A.

The fold modulation may be calculated with reference to mock infected myotubules (infected by an adenovirus not expressing E1A) such as dl312 and a standard gene, e.g., GAPDH, as controls. All cells used in the experiment should be kept in the same culture conditions. The skilled person may make reference to the examples for other details. Additionally, an exemplary protocol as used in the examples of the present application is provided as follows:

Total RNA is isolated with the Triazol method (Invitrogen). Two µg of RNA are used, with 100 ng of random examers, in a reverse transcription reaction (SUPERSCRIPT II, Invitrogen). One-tenth ng of cDNA is amplified, in triplicate, in a reaction volume of 20 µL with 10 pMol of each gene specific primer and the SYBR-green PCR MasterMix (Applied Biosystems).

Real-time PCR is carried out on the ABI/Prism 7700 Sequence Detector System (Perkin-Elmer/Applied Biosystems), using a pre-PCR step of 10 min at 95° C., followed by 40 cycles of 15 s at 95° C. and 60 s at 60° C. Specificity of the amplified products is confirmed by melting curve analysis (DISSOCIATION CURVE™ Perkin-Elmer/Applied Biosystems) and by 6% PAGE. Preparations with RNA template without reverse transcriptase are used as negative controls. Samples are amplified with primers for each genes and GAPDH as a housekeeping gene (other housekeeping genes, including rRNA 18S and beta-actin could be used with comparable results). The Ct values are normalized to the GAPDH curve and the relative expression of each gene is expressed as the ratio relative to mock (dl312) infected myotubes.

A gene which is not strongly modulated (e.g., induced) by inactivation of a pocket protein may have a ratio of modulation by pocket protein inactivation as compared to modulation by wild type E1A of less than 0.6. It may be preferred that the gene is not significantly modulated by inactivation of a pocket protein such as Rb, in which case the gene may have a ratio of modulation by pocket protein (e.g., Rb) inactivation as compared to modulation by wild type E1A of less than 0.4. The gene encoding the pocket protein, e.g., Rb, may be removed by CRE, to ascertain the level of modulation caused by inactivation of the pocket protein. The pocket protein sequence, e.g., the RB sequence, may be floxed.

A gene which is significantly modulated (e.g., induced) by E1A pocket binding mutants such as YH47/DL928 may have a fold induction ratio of at least 0.4 between contact with such a mutant and contact with wild type E1A.

It may in some embodiments be preferred that the gene or genes which are not well induced by inactivation of a pocket protein, and which are significantly modulated by E1A pocket binding mutants, also fulfil either or both of the following criteria:
they are late modulated genes as defined above; and/or
they are not significantly modulated by E2F1 overexpression.

Late induced genes may be those which have a ratio between the fold induction (e.g., of transcript) at 24 hours and at 36 hours of less than 0.4 (i.e., 40% induction). It may be assessed in a cell which has been infected with an adenovirus comprising the 12S mRNA of E1A. The ratio may be assessed as set out in the examples Genes which are not significantly modulated (e.g., induced) by E2F1 overexpression may be those show less than 40% on E2F1 overexpression compared to the wild type E1A. E2F1 overexpression may be achieved by tranfecting the cell with E2F1 under the control of the CMV promoter.

For example, it may be achived by infecting the cells with Ad-E2F1 adenovirus infection (MOI 300), which has been described in Pajalunnga et al 1998 and DeGregori 1997.

Assay Methods

In certain aspects, the invention provides methods which include the step of bringing a protein into contact with a test agent or candidate modulator, and determining whether said test agent is capable of binding and/or modulating the activity of the protein.

The protein used in the assay may be a mammalian protein, preferably a human protein. It may also be a fragment or variant of the full length mammalian protein. Preferred fragments and variants are those which retain the activity of the mammalian protein. Fragments may comprise at least 10, more preferably at least 20, 30, 40 or 50 consecutive amino acids of the mammalian protein sequence. A variant may have at least 70%, 80%, 90%, 95% or 99% identity to a full length mammalian sequence, preferably to the human sequence, assessed over the full length of the mammalian sequence.

The percentage identity of amino acid sequences can be calculated using commercially available algorithms. The following programs (provided by the National Center for Biotechnology Information) may be used to determine homologies: BLAST, gapped BLAST, BLASTN and PSI-BLAST, which may be used with default parameters.

The protein for use in the assay may be fused to a heterologous sequence, e.g., a sequence allowing the protein to be isolated and/or immobilised.

The ability of a test agent to bind to the protein may be assessed by any of the methods known in the art. Binding assays may be competitive or non-competitive.

The assay method may comprise determining whether the test agent is capable of inhibiting the protein, or determining whether the test agent is capable of activating the protein.

Where the gene expression is downregulated in a human tumour, the assay is preferably for an activator of the protein, and the assay preferably involves determining whether the test agent is capable of increasing the activity of the protein. In this embodiment, the assay may be carried out under conditions where the protein normally shows low or no activity.

Where the gene expression is upregulated in a tumour, the assay is preferably for an inhibitor of the activity of the protein, and the assay preferably involves determining whether the test agent is capable of reducing the activity of the protein. In this embodiment, the assay may be carried out under conditions in which the protein is normally active.

The determination of modulation of activity will depend upon the nature of the protein being assayed. For example, proteins with enzymatic function may be assayed in the presence of a substrate for the enzyme, such that the presence of a test agent capable of modulating the activity results in a faster or slower turnover of substrate. The substrate may be the natural substrate for the enzyme or a synthetic analogue. In either case, the substrate may be labelled with a detectable label to monitor its conversion into a final product.

For proteins with a ligand binding function, such as receptors, the test agent may be examined for ligand binding function in a manner that leads to antagonism or agonism of the ligand binding property.

For proteins with DNA binding activity, such transcription regulators, the DNA binding or transcriptional activating activity may be determined, wherein a modulator is able to either enhance or reduce such activity. For example, DNA binding may be determined in a mobility shift assay. Alternatively, the DNA region to which the protein bind may be operably linked to a reporter gene (and additionally, if needed, a promoter region and/or transcription initiation region between said DNA region and reporter gene), such that transcription of the gene is determined and the modulation of this transcription, when it occurs, can be seen. Suitable reporter genes include, for example, chloramphenicol acetyl transferase or more preferably, fluorescent reporter genes such as green fluorescent protein.

Test agents may be natural or synthetic chemical compounds used in drug screening programmes. Extracts of plants, microbes or other organisms, which contain several characterised or uncharacterised components may also be used. Combinatorial library technology (including solid phase synthesis and parallel synthesis methodologies) provides an efficient way of testing a potentially vast number of different substances for ability to modulate an interaction. Such libraries and their use are known in the art, for all manner of natural products, small molecules and peptides, among others. Many such libraries are commercially available and sold for drug screening programmes of the type now envisaged by the present invention.

A further class of test agents or candidate modulators are antibodies or binding fragment thereof which bind a protein target, as described above.

Another class of test agents are peptides based upon a fragment of the protein sequence to be modulated. In particular, fragments of the protein corresponding to portions of the protein which interact with other proteins or with DNA may be a target for small peptides which act as competitive inhibitors of protein function. Such peptides may be for example from 5 to 20 amino acids in length.

The peptides may also provide the basis for design of mimetics, as explained in more detail below. In other aspects, the invention provides methods comprising the step of providing a transformed cell in culture, and determining whether a test agent is capable of modulating (inhibiting or activating) the levels of a gene transcript.

In such a method, the transformed cell may be a tumour cell, e.g., isolated from a human subject, or may be a cell which has been contacting with a transforming agent or an agent which causes re-entry of a terminally differentiated cell into the cell cycle. For example, the cell may be a cell which has been contacted with an E1A protein as described above, e.g., by infecting the cell with an adenovirus. The cell may be a terminally differentiated cell.

Cell based assay methods can be configured to determine expression of the gene either at the level of transcription or at the level of translation. Where transcripts are to be measured, then this may be determined using the methods described above, e.g. on gene chips, by multiplex PCR, or the like.

As above, where the transcript is one which is downregulated in tumours, the assay is preferably for agents which increase the expression of the gene (e.g., by increasing the quantity of the transcript). Such an agent may comprise the coding sequence of the gene itself (i.e., it may be a gene therapy vector). Where the transcript is one which is upregulated in human tumours, the assay is preferably for agents which decrease the expression of the gene.

Cell based assay methods may be used to test agents of the sorts described above. They may also be used to screen further classes of test agents/candidate modulators, including antisense oligonucleotides. Such oligonucleotides are typically from 12 to 25, e.g. about 15 to 20 nucleotides in length, and may include or consist of modified backbone structures, e.g. methylphosphonate and phosphorothioate backbones, to help stabilise the oligonucleotide. The antisense oligonucleotides may be derived from the coding region of a target gene or be from the 5' or 3' untranslated region. Test agents may further include RNAi, i.e. short double stranded RNA molecules which are sequence specific for a gene transcript. They may also include ribozymes which specifically target the transcript mRNA, i.e., a catalytic RNA molecule which cleaves other RNA molecules of a particular nucleic acid sequence. General methods for the construction of ribozymes are known in the art.

Agents obtained in accordance with the present invention may be used in methods of treating cancer in a patient. Generally, the modulator will be formulated with one or more pharmaceutically acceptable carriers suitable for a chosen route of administration to a subject. For solid compositions, conventional non-toxic solid carriers include, for example, pharmaceutical grades of mannitol, lactose, cellulose, cellulose derivatives, starch, magnesium stearate, sodium saccharin, talcum, glucose, sucrose, magnesium carbonate, and the like may be used. Liquid pharmaceutically administrable compositions can, for example, be prepared by dissolving, dispersing, etc, a modulator and optional pharmaceutical adjuvants in a carrier, such as, for example, water, saline aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound(s) in an amount effective to alleviate the symptoms of the subject being treated.

Routes of administration may depend upon the precise condition being treated.

Inhibitors of SKIN activity or expression, which can be used in methods of treating cancer, can be any of the agents described above.

Design of Mimetics

Once candidate substance have been found in the assays and screens according to the present invention, they may be used to design mimetic compounds for development as drugs. The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, e.g. peptides are unsuitable active agents for oral compositions as they tend to be quickly degraded by proteases in the alimentary canal. Mimetic design, synthesis and testing is generally used to avoid randomly screening large number of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, e.g. by substituting each residue in turn. These parts or residues constituting the active region of the compound are known as its "pharmacophore".

Once the pharmacophore has been found, its structure is modelled to according its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of this approach, the three-dimensional structure of the ligand and its binding partner are modelled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the lead compound. The mimetic or mimetics found by this approach can then be screened to see whether they have the target property, or to what extent they exhibit it. Further optimisation or modification can then be carried out to arrive at one or more final mimetics for in vivo or clinical testing.

Determination of Protein, Gene or Transcript Levels

A gene expression product as referred to herein may be a protein or a transcript (i.e., an RNA molecule expressed by the gene).

Determination of protein, gene or transcript level may be made by any of the methods known in the art.

For example, suitable methods for assessing protein levels include immunohistochemistry (e.g., immunofluorescence), western blotting, and solid phase methods such as ELISA (enzyme-linked immunoabsorbant assay).

Using immunohistochemical techniques, an assessment of protein level can be made by determining the proportion of cells showing labelling (e.g., staining or fluorescence).

Transcript level may be determined by in situ hybridisation, e.g., accompanied by assessment of the proportion of cells showing hybridisation.

Alternatively, or in addition, quantitative PCR methods may be used, e.g. based upon the ABI TaqMan™ technology, which is widely used in the art. It is described in a number of prior art publications, for example reference may be made to WO00/05409. PCR methods require a primer pair which target opposite strands of the target gene at a suitable distance apart (typically 50 to 300 bases). Suitable target sequences for the primers may be determined by reference to Genbank sequences.

Where many different gene transcripts are being examined, a convenient method is by hybridisation of the sample (either directly or after generation of cDNA or cRNA) to a gene chip array and/or micro fluidic card (Low density array) based on quantitative PCR methods.

Where gene chip technology is used, the genes may be present in commercially available chips from Affymetrix, and these chips may be used in accordance with protocols from the manufacturer. Generally, methods for the provision of microarrays and their use may also be found in, for example, WO84/01031, WO88/1058, WO89/01157, WO93/8472, WO95/18376/WO95/18377, WO95/24649 and EP-A-0373203 and reference may also be made to this and other literature in the art.

Where microfluidic card technology is used, the genes may be present in commercially available microfluidic cards from Applied Biosystem, also known as Low Density Arrays. These cards may be used in accordance with protocol from the manufacturer.

TaqMan® Low Density Arrays are customizable, easy-to-use, 384-well micro fluidic cards for real-time PCR-based quantitative gene expression applications (ABI TaqMan™ technology). Over than 40,000 inventoried TaqMan® assays covering human, mouse, and rat genes, are commercially available.

The micro fluidic technology uses 8 sample-loading ports, each connected to 48 reaction wells.

384 well TaqMan® array is run on the Applied Biosystems 7900HT Fast Real Time PCR System.

Gene copy number may be determined using techniques known in the art, including in situ hybridisation (ISH) with nucleic acid probes which may be labelled with e.g. a fluorescent label (FISH), or PCR of genomic DNA.

Reference or Control Samples

When a method of the invention comprises determining the gene status of an assay sample obtained from a patient and/or determining the level of a gene expression product, the method may also comprise comparing the determination made on that sample with a determination made on a reference or control sample.

Reference or control samples for the above methods may be a sample of normal (unaffected) cells, preferably cells of the same type as the assay sample. Alternatively, the sample may be a sample of cells affected by cancer, preferably a cancer of the same type as is in the patient or is suspected to be in the patient.

Where the aim is to distinguish between different states or different levels of aggression of a cancer (e.g., in a method of prognosis), the control sample may preferably be taken from a tumour cell having one of the states of interest. For example, the control sample may be a sample taken from a tumour from a metastatic tumour, or may be a sample from a non-metastatic tumour. For colon cancer, the control sample may be taken from one or more of hyperplastic polyps, adenomas and carcinomas. Generally, the control sample may be a sample of cells from a tissue type associated with the presence or absence of cancer, and/or from a tumour with good or with poor prognosis.

The control sample may be obtained from the patient, from another subject or from a population of subjects. Where a population of subjects is used, the comparison may be made with the average (e.g., mean or median) in samples of cells from said population.

One advantage of using a control of normal tissue from the same patient is that it accounts for any individual variation. Where the control is from another patient (either of normal or affected tissue), this may also be a reason why results based on a population of patients may be preferred.

In some embodiments, the method may comprise the use of more than one control; for example the sample to be tested may be compared to a normal sample from the same patient and the transcript level of an affected sample from another patient or patients. In another example, the sample to be tested may be compared to one or more sample from a metastatic tumour and one or more samples from a non-metastatic tumour.

Where the assay sample is a sample of affected tissue obtained from the patient, it may be preferred that the control sample is obtained from the patient at an earlier time point, so as to provide a historical record. In one embodiment, this allows for the assessment of the monitoring of the progression of the condition over time.

In another embodiment, this allows for assessment of the effectiveness of a particular treatment. By comparing the severity of the condition in a patient at two time points, it is possible to determine whether a particular treatment regime is having a positive effect or not. The effectiveness of any one regime may differ from patient to patient, or during the course of the disease.

Comparison the gene status or to the level of a gene expression product in a control sample may of course be comparison to previously determined data, and need not comprise the step of analysing the control sample.

Specific Binding Partners and Kits

The specific binding partner for a protein may be an antibody, as defined below, and is preferably a monoclonal antibody. The antibody may be detectable labelled.

Where the gene expression product is a transcript, the specific binding partner may be a nucleic acid sequence capable of specifically hybridising to said transcript. The nucleic acid sequence may be detectably labelled. It may be a primer, e.g., for quantitative PCR.

By "specific" is meant a binding partner which is suitable for detection of the transcript or protein in a complex mixture. The binding partner may bind to the gene expression product preferentially over other transcripts/proteins in the same species and may have no or substantially no binding affinity for other proteins or transcripts. In the case of a transcript, the transcript is preferably capable of distinguishing the target transcript from other transcripts in the mixture at least under stringent hybridisation conditions.

In various aspects, the invention relates to kits which comprise a specific binding partner for a gene expression product. In some embodiments, the specific binding partner may be immobilised on a solid support.

Where the specific binding partner is an antibody, the kit may further comprise a detectably labelled moiety capable of binding to a complex between the protein and its specific binding partner. Additionally or alternatively, the kit may include one or more of the following reagents:

a) a reagent to fix a tissue, such as paraformaldeheyde;
  b) a reagent to "unmask" cellular antigens upon fixation (such as EDTA-based solutions or citrate buffer); and/or
  c) a detection system to reveal the enzymatic activity coupled to the primary antibody or the secondary moiety (e.g., secondary antibody), where the label is an enzyme, such as peroxidase.

For example, the kit may be for immunohistochemical techniques, and may comprise a first antibody capable of binding the protein to be detected, and a second, labelled antibody capable of binding said first antibody.

Alternatively, the kit may comprise a first, immobilised antibody capable of binding the protein to be detected and a second, labelled antibody capable of binding the protein when bound to the first antibody.

A label may be a radioactive, fluorescent chemiluminescent or enzyme label. Radioactive labels can be detected using a scintillation counter or other radiation counting device, fluorescent labels using a laser and confocal microscope, and enzyme labels by the action of an enzyme label on a substrate, typically to produce a colour change. After the binding reaction and any necessary separation step has taken place, the result of the assay is obtained by contacting the enzyme with a substrate on which it can act to produce an observable result such as a colour change, the extent of which depends on the amount of analyte originally in the sample. Suitable enzyme labels may give rise to detectable changes such as calorimetric, fluorometric, chemiluminescent or electrochemical changes, and include horseradish peroxidase and alkaline phosphatase, as well as lysozyme (detectable for example by lysis of organisms such as microccocus lysodeikticus), chymotrypsin, and E. coli DNA polymerase.

Other possible labels include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors.

Other methods may also be used to detect interaction between the protein and the antibody, including physical methods such as surface plasmon resonance, agglutination, light scattering or other means.

In another embodiment, the kit may comprise primers for PCR analysis of RNA samples or genomic DNA from patients, i.e., primers which are capable of hybridising to an RNA expression product of the gene in question, or to the gene itself, and of serving as extension primers. Optionally, the PCR may be quantitative PCR.

In other embodiments, the kit may be a gene chip array, in which case it preferably comprises a control specific for said at least one transcript; and optionally at least one control for the gene chip.

In another embodiment, the kit may comprise probes for FISH analysis of gene copy number or other genetic alterations.

The identification of a relatively small set of genes of use in assessing the conditions discussed above allows the provision of a small chip specifically designed to be suitable for use in the present invention.

Desirably, the number of sequences in the array will be such that where the number of nucleic acids suitable for detection of the marker transcript is n, the number of control nucleic acids specific for individual transcripts is n', where n' is from 0 to 2n, and the number of control nucleic acids (e.g. for detection of "housekeeping" transcripts, transcripts having normally high levels in the cell type being assessed, or the like) on said gene chip is m where m is from 0 to 100, preferably from 1 to 30, then n+n'+m represent at least 50%, preferably 75% and more preferably at least 90% of the nucleic acids on said chip.

Antibodies

Methods of producing antibodies are known in the art. Preferred antibodies are isolated, in the sense of being free from contaminants such as antibodies able to bind other polypeptides and/or free of serum components. Monoclonal antibodies are preferred for some purposes, though polyclonal antibodies are within the scope of the present invention.

Where the kits comprise more than one antibody, these are preferably mixtures of isolated antibodies as described above.

Antibodies may be obtained using techniques which are standard in the art. Methods of producing antibodies include immunising a mammal (e.g. mouse, rat, rabbit) with a polypeptide of the invention. Antibodies may be obtained from immunised animals using any of a variety of techniques known in the art, and screened, preferably using binding of antibody to antigen of interest. For instance, Western blotting techniques or immunoprecipitation may be used (Armitage et al, Nature, 357:80-82, 1992).

As an alternative or supplement to immunising a mammal with a peptide, an antibody specific for a protein may be obtained from a recombinantly produced library of expressed immunoglobulin variable domains, e.g. using lambda bacteriophage or filamentous bacteriophage which display functional immunoglobulin binding domains on their surfaces; for instance see WO92/01047.

Antibodies according to the present invention may be modified in a number of ways. Indeed the term "antibody" should be construed as covering any binding substance having a binding domain with the required specificity, e.g., antibody fragments, derivatives, functional equivalents and homologues of antibodies, including synthetic molecules and molecules whose shape mimics that of an antibody enabling it to bind an antigen or epitope.

Example antibody fragments, capable of binding an antigen or other binding partner are the Fab fragment consisting of the VL, VH, Cl and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

Humanized antibodies in which CDRs from a non-human source are grafted onto human framework regions, typically with the alteration of some of the framework amino acid residues, to provide antibodies which are less immunogenic than the parent non-human antibodies, are also included within the present invention.

Vectors and Antibodies for SKIN

The protein SKIN, identified herein as a protein which is useful both as a marker and as a therapeutic target for cancer, has not previously been attributed a function.

This provides basis for antibodies specific to the SKIN protein useful in aspect of the invention described above, and such antibodies are a further aspect of the invention.

This also provides the basis for novel vector systems useful in aspects of the invention described above, as well as further aspects described herein below.

Preferably, the sequence of a SKIN transcript or a sequence complementary to said transcript (e.g., an antisense sequence) is operably linked to a control sequence which is capable of providing for expression of the coding sequence (e.g., the DNA sequence encoding said transcript) by a host cell, i.e., the vector is an expression vector.

The term "operably linked" refers to a juxtaposition wherein the components described are in a relationship permitting them to function in their intended manner. A control sequence "operably linked" to a coding sequence is ligated in such a way that expression of the coding sequence is achieved under condition compatible with the control sequences.

Suitable host cells include bacteria, eukaryotic cells such as mammalian and yeast, and baculovirus systems. Mammalian cell lines available in the art for expression of a heterologous polypeptide include Chinese hamster ovary cells, HeLa cells, baby hamster kidney cells, COS cells and many others.

The vectors may include other sequences such as promoters or enhancers to drive the expression of the inserted nucleic acid, nucleic acid sequences so that the polypeptide is produced as a fusion and/or nucleic acid encoding secretion signals so that the polypeptide produced in the host cell is secreted from the cell.

The vectors may contain one or more selectable marker genes, for example an ampicillin resistance gene in the case of a bacterial plasmid or a neomycin resistance gene for a mammalian vector.

Vectors may further include enhancer sequences, terminator fragments, polyadenylation sequences and other sequences as appropriate.

Vectors may be used in vitro, for example for the production of RNA or used to transfect or transform a host cell. The vector may also be adapted to be used in vivo, for example in methods of gene therapy. Systems for cloning and expression of a polypeptide in a variety of different host cells are well known. Vectors include gene therapy vectors, for example vectors based on adenovirus, adeno-associated virus, retrovirus (such as HIV or MLV) or alpha virus vectors.

Promoters and other expression regulation signals may be selected to be compatible with the host cell for which the expression vector is designed. For example, yeast promoters include S. cerevisiae GAL4 and ADH promoters, S. pombe nmt1 and adh promoter. Mammalian promoters include the metallothionein promoter which is induced in response to heavy metals such as cadmium. Viral promoters such as the SV40 large T antigen promoter or adenovirus promoters may also be used. All these promoters are readily available in the art.

Vectors for production of SKIN polypeptide include vectors which carry a mini-gene sequence.

Vectors may be transformed into a suitable host cell as described above to provide for expression of a polypeptide of the invention. Thus, in a further aspect the invention provides a process for preparing SKIN polypeptides which comprises cultivating a host cell transformed or transfected with an expression vector as described above under conditions to provide for expression by the vector of a coding sequence encoding the polypeptides, and recovering the expressed polypeptides. Polypeptides may also be expressed using in vitro systems, such as reticulocyte lysate.

EXAMPLES

The following examples are provided by way of illustration.

Materials and Methods

Tissue Samples and Primary Cells

Mammary tissue specimens were obtained from patients undergoing surgery for the removal of breast neoplasias. Samples were minced and suspended for 8-12 h in DMEM with 5% FBS, 5 mg/ml insulin, 200 U/ml collagenase and 100 U/ml hyaluronidase. Cells of epithelial and fibroblastic origin were separated as previously described (Speirs, V. et al. Short-term primary culture of epithelial cells derived from human breast tumours. *Br J Cancer* 78, 1421-9, 1998) followed by differential trypsinisation (Hammond, S. L., Ham, R. G. & Stampfer, M. R. Serum-free growth of human mammary epithelial cells: rapid clonal growth in defined medium and extended serial passage with pituitary extract. *Proc Natl Acad Sci USA* 81, 5435-9, 1984).

The epithelial origin of the cultures was confirmed by immunofluorescence with an anti-Pan cytokeratin antibody (Sigma). Second-passage cells, which were practically epithelial-pure, were used for all described experiments Primary cultures were cultivated according to published procedures (Hammond et al, as above). MG132 was used at a concentration of 10 µM for the indicated lengths of time. The g-secretase inhibitor DFP-AA (compound E, Calbiochem) was used at a concentration of 1 µM and added in fresh medium every 24h for 10 days. Mock-treated controls were exposed to equivalent concentrations of carrier (0.05% dimethyl sulfoxide).

Expression Vectors and Biological Assays

A Numb-GFP expression vector was obtained by recombinant PCR and subcloning in a retroviral (Pinco) vector, followed by sequence verification.

Primary cells (50,000/well) were infected in six-well plates with supernatants from FNX (Phoenix cells) transfected with Pinco-Numb-GFP or with Pinco-GFP, as a control, every three days for 3 weeks.

A luciferase reporter plasmid (6x-RBP-Jk-luc, kindly provided by U. Lendahl, Karolinska Institute, Stockholm), containing 6 copies of the CBF1 binding consensus sequence, was used to evaluate Notch-dependent signalling. Primary mammary cells were transfected, in six-well plates, with 800 ng of 6x-RBP-Jk-luc and 200 ng of CMV-b-galactosidase expression plasmids. Luciferase activity was evaluated 48 h posttransfection and normalised for transfection efficiency by b-galactosidase expression.

Western Blot, siRNA, Immunofluorescence and Immunocytochemistry

An affinity-purified anti-Numb peptide antibody was used for immunoblotting, immunofluorescence and immunocytochemistry (Santolini, E. et al. Numb is an endocytic protein. *J Cell Biol* 151, 1345-52, 2000).

For immunohistochemical analysis, tissue sections were routinely processed, treated for antigen retrieval and incubated overnight with anti-Numb antibody. Bound antibody was detected using the EnVision detection system and diaminobenzidine as chromogenic substrate. Counterstain was with Meyer's hematoxylin.

To assess the ubiquitination status of Numb in tumours in vivo, total cell lysates were subjected to immunoprecipitation with a mouse monoclonal antibody raised against the exon-10 of human Numb and not cross-reactive with the Numb-related gene, Numbl (data not shown). To detect ubiquitination, a mouse monoclonal antibody, FK1 (Affiniti Research Product), was used. Other antibodies were: anti-Notch1 (c-20, Santacruz Biotechnology), HRP-conjugated secondary antibodies (Amersham), fluorochrome-conjugated secondary antibodies (Jackson ImmunoResearch Laboratories, Inc).

For siRNA experiments, delivery of siRNA oligos for Numb or scrambled oligos, as a control, was achieved using Oligofectamine.

The targeted sequences were:

```
                                          (SEQ ID NO: 2)
    Numb siRNA, AACAGCCACTGAACAAGCAGA;

(SEQ ID NO: 3)
    scrambled siRNA, AGACGAACAAGTCACCGACTT.
```

Selected sequences were submitted to BLAST searches against the human genome sequence to ensure that only the desired mRNA was targeted.

In situ Hybridisation

Numb expression was assessed by in situ hybridisation using 35S-UTP-labeled sense and antisense riboprobes. After overnight hybridisation at 50° C., tissue sections were washed in 50% formamide, 2xSSC, 20 mM 2-mercaptoethanol at 60° C., and coated with Kodak NTB-2 liquid emulsion to reveal radiolabelling. The sequence of the sense probe is:

CCATCCTCTCCCACCTCTCCTACTTCT- (SEQ ID NO: 4)
GATGCCACGACCTCTCTGGAGAT

GAACAATCCTCATGCCATCCCACGCCG-
GCATGCTCCAATTGAACAGCTTG

CTCGCCAAGGCTCTTTCCGAGGTTTTC-
CTGCTCTTAGCCAGAAGATGTCA

CCCTTTAAACGCCAACTATCCCTACGCATCAATGAG.

Quantitative RT-PCR Quantitative RT-PCR analysis was performed on the Perkin -Elmer/Applied Biosystems Prism 7700 Sequence Detection System (Foster City, Calif., USA). Primer sequences used were as follows: Hesl_Fw: 5' CAG CTT GGC TGT GGT AGA AGC 3' (SEQ ID NO: 5). Hesl-Rev: 5' CCA CTG ACC CCT ACC TTC TAT CC 3' (SEQ ID NO: 6), GAPDHFw: 5' GCC TCA AGA TCA TCA GCA ATG C 3' (SEQ ID NO:7), GAPDH_Rev: 5' CCA CGA TAC CAA AGT TGT CAT GG 3 (SEQ ID NO: 8). Each cDNA sample was tested in triplicate. For quantification of gene expression changes, the DDCt method was used to calculate relative fold changes normalised against the Glyceraldehyde 3-phosphate dehydrogenase (GAPDH) gene, as described in the manufacturer's protocol (Applied Biosystems).

Example 1

We characterised by immunohistochemistry 321 consecutive breast cancers. The clinical and pathological features of the breast cancer patients are shown below.

TABLE 1

| Variable | Frequency | Percent |
|---|---|---|
| Age | | |
| 0-39 | 39 | 12.4 |
| 40-49 | 82 | 26.1 |
| 50-59 9 | 92 | 29.3 |
| 60-69 | 77 | 24.5 |
| 70+ | 24 | 7.6 |
| Histotype | | |
| Ductal | 249 | 77.6 |
| Lobular | 38 | 11.8 |
| Other | 34 | 10.6 |
| Stage (pT classification) | | |
| pT1 | 206 | 64.2 |
| pT2 | 95 | 29.6 |
| pT3-4 | 20 | 6.2 |
| Grade | | |
| 1 | 70 | 21.8 |
| 2 | 124 | 38.6 |
| 3 | 127 | 39.6 |
| Oestrogen receptor | | |
| <10% | 75 | 23.4 |
| >10% | 246 | 76.6 |
| Progesterone receptor | | |
| <10% | 148 | 46.1 |
| >10% | 173 | 53.9 |
| Ki-67 | | |
| <22% | 147 | 45.8 |
| >22% | 174 | 54.2 |

TABLE 1-continued

| Variable | Frequency | Percent |
|---|---|---|
| Lymph node metastasis | | |
| NEG | 231 | 72.0 |
| POS | 90 | 28.0 |

Archival formalin-fixed, paraffin-embedded surgical specimens from the patients were analysed for Numb expression by immunohistochemistry. Tumours were histologically classified according to WHO Histological Classification of Breast Tumours (WHO. Histological typing of breast tumours, 2nd ed., international histological classification of tumours no. 2. Geneva: WHO; 1981) as modified by Rosen and Oberman (Rosen, P. P., Oberman, H. A. Tumours of the mammary gland. Washington D.C.: Armed Forces Institute of Pathology; 1993). Grading of tumours was defined according to Elston and Ellis (Elston, C. W., Ellis, I. O. Pathological prognostic factors in breast cancer: the value of histological grade in breast cancer. Histopathology 19, 403-410; 1991). Oestrogen and progesterone receptor status and the tumour proliferative fraction (Ki-67) were assessed by immunohistochemistry on paraffin sections, according to routine procedures. Primary monoclonal antibodies to oestrogen receptors and progesterone receptors (Dako. Glostrup, Denmark) were used at 1/100 dilution. MIB-1 monoclonal antibody to the Ki-67 antigen (Immunotech, Marseille, France) was used at 1/200 dilution. For oestrogen and progesterone receptor as well as for Ki-67 staining, values are expressed as percentage of immunoreactive cells.

The normal breast parenchyma invariably showed intense and homogeneous Numb staining (FIG. 1a). Conversely, tumours displayed marked heterogeneity, and in many cases complete absence of Numb immunoreactivity, which allowed their classification into three classes (FIG. 1a). Class-1 (38.3% of the cases) tumours showed Numb staining in less than 10% of the neoplastic cells. Within this category, more than one half of tumours did not display any detectable Numb (type-0 tumours). Class-2, and -3 tumours (16.8%, and 44.9%, respectively) showed Numb immunoreactivity in 10-50%, and >50% of the tumour cells, respectively. Thus, more than one half of all breast tumours (classes 1-2 combined) had reduced levels of Numb.

The levels of Numb expression were also correlated with several indicators relevant for the natural history of the tumour. When a cut off of <10% of Numb expressing cells was adopted (class-1 vs. 2-3), a strong inverse correlation was found between Numb expression and tumour grade (P=0.001) and Ki67 labelling index (P=0.001), whereas there was no significant correlation with age, size of the tumour, histotype, lymph node or receptor status. In multivariate analysis, the correlation with Ki67 was maintained (P=0.023), whereas that with tumour grade was slightly above the threshold of significance (P=0.057). Thus, remarkably, a strong inverse correlation was found between Numb expression levels and tumour grade (P=0.001) and Ki67 labelling index (P=0.001), which are known indicators of aggressive disease (table 1).

Example 2

We next analysed the presence of Numb transcripts in human mammary tumours, by in situ hybridisation. Five class-3 tumours, and 14 class-1 (type-0) tumours were analysed. All of the class-3 tumours (and normal glands surrounding the tumours) displayed readily detectable levels of Numb transcripts (FIG. 1b). Interestingly, 12 of 14 class-1 (type-0) tumours displayed levels of Numb mRNA expression comparable to those detected in normal tissues and in class-3 tumours (FIG. 1b).

In addition, we could not detect any genetic alteration, affecting the Numb locus by both analysis of loss of heterozigosity, and by direct sequencing of Numb cDNAs prepared from several Numb-negative tumours. Thus, genetic alterations at the Numb locus are unlikely to account for lack of Numb expression in the human breast tumours examined.

Loss of heterozygosity was assessed according to the following method.

7 polymorphic STS markers (D14S 71, D14S77, D14S268, D14S277, D14S43, D14S70 and D14S785) localised on chr. 14q23 were selected from the genomic database (NCBI, accession No. Z16844, Z24162, Z23878, Z16997, X56973, Z16819 and X569055, respectively) according to both their high frequency of heterozigosity in a control population, and to their proximity to the Numb locus. Specific primer pairs flanking the (CA) n repeat were chosen for each STS marker.

PCR reaction were assembled in a final volume of 50 µl according to the Taq-gold polymerase manufacturer's instructions (Perkin-Elmer) with the following modifications: 10 pmoles of each primer pair was used; dNTP final concentration in the PCR reaction was 200 µM for dATP/dGTP/dTTP and 10 µM for dCTP; 0.025 µl/reaction of α32PdCTP (3000 Ci/mol); 20-50 rig of genomic DNA. Genomic DNA was extracted from matched paraffin embedded normal and tumour tissues and tested separately. PCR condition were as follows: 94° C. 30", 58° C. ->53° C. 30" (decrease of 0.5/cycle), 72° C. 30" for 10 cycles; 94° C. 30", 53° C. 30". 72° C. 30" for 20 cycles. PCR reaction was denatured with 5 µl of loading buffer (10X: 98% formamide; 1 mM EDTA; 0.1% bromophenol blue; 0.1% Xylene cyanol), for 5' and run on a 7% acrylamide gel. TBE 1X and 32% formamide. The following primers were used:

```
                                    (SEQ ID NOS: 9 and 10)
    D14S277   (5'-ctccccattgctttcact-3';

5'-ttgaagattcagataaggt-3');

(SEQ ID NOS: 11 and 12)
    D14S43    (5'-ctggaacactcaggcgag-3';

5'-gccactttctactttggg-3');

(SEQ ID NOS: 13 and 14)
    D14S71    (5'-tgtgcaccaatgcctcct-3';

5'-gcccggccagaaatgctt-3');

(SEQ ID NOS: 15 and 16)
    D14S77    (5'-gcctgagtcactgtgcc-3';

5'-cagacagaaattaaccagag-3');

(SEQ ID NOS: 17)
    D14S268   (5'-agcttcctactgtgtaaaacga-3';

(SEQ ID NOS: 18)
              5'-ggctggggctgcaccttgta-3');

(SEQ ID NOS: 19)
    D14S70    (5'-agctaatgacttagacacgttgta-3';

(SEQ ID NOS: 20)
              5'-atcaatttgctagtttggca-3');
```

```
                                    (SEQ ID NOS: 21 and 22)
    D14S785   (5'-gctctgtctcac-3';

5'-gatcattgacataggaaacac-3').
```

Twenty class-1 and 10 class-3 breast tumours were analysed for LOH. Out of forty tumours analysed, LOH was detected in only one class 1 (type-0) mammary tumour. However, the sequence of transcripts originating from the non-deleted Numb allele, in that tumour, did not show any alteration, with respect to the wild-type sequence (not shown).

In addition, we selected two class 1 (type-0) tumours, which showed presence of Numb transcripts by ISH, and isolated areas of high tumour cellularity (>90%). Numb transcripts, cloned from these tumours by RT-PCR, did not show any mutation with respect to the wild type sequence (data not shown). We concluded that genetic alterations at the Numb locus are unlikely to account for lack of Numb expression in the majority of human breast tumours.

Example 3

To gain insight into the molecular mechanisms responsible for loss of Numb expression, we established primary cultures from class-1 (type-0) and class-3 mammary tumours, and from normal breast tissues from the same patients, and analysed them within the first two passages in vitro, as follows.

Normal and tumour mammary epithelial cells were grown in appropriate selective medium, as described in Methods. Normal cell cultures typically show two major morphological types of cells (top-left): small, smooth-edged, refractile, polygonal cells, which maintain active proliferation and seemingly represent some form of "stem cell population"; and larger, flatter, irregular shaped cells, which do not seem to undergo many cell divisions. The latter might represent cells already programmed to stop multiplying after a few more population doublings. Tumour cells usually display a much higher morphological heterogeneity (top-right), ranging from a typical epithelial appearance to an irregular spindle-like phenotype, resembling a more 'dedifferentiated' status. By the second passage, normal and tumour primary cultures were proven to be of pure epithelial origin, by immunofluorescence staining for keratin expression). Myoepithelial cell component was <1-2%, as assessed by α-smooth muscle actin staining (not shown). A mixture of monoclonal antibodies recognising the major cytokeratins (CK 1, 4, 5, 6, 8, 10, 13, 18 and 19, Sigma C2562) and a monoclonal antibody against α-smooth muscle actin (Sigma, clone 1A4) were used on ethanol-fixed cells grown on glass coverslips. Results are representative of all matched pairs used in this study.

Figure 2:
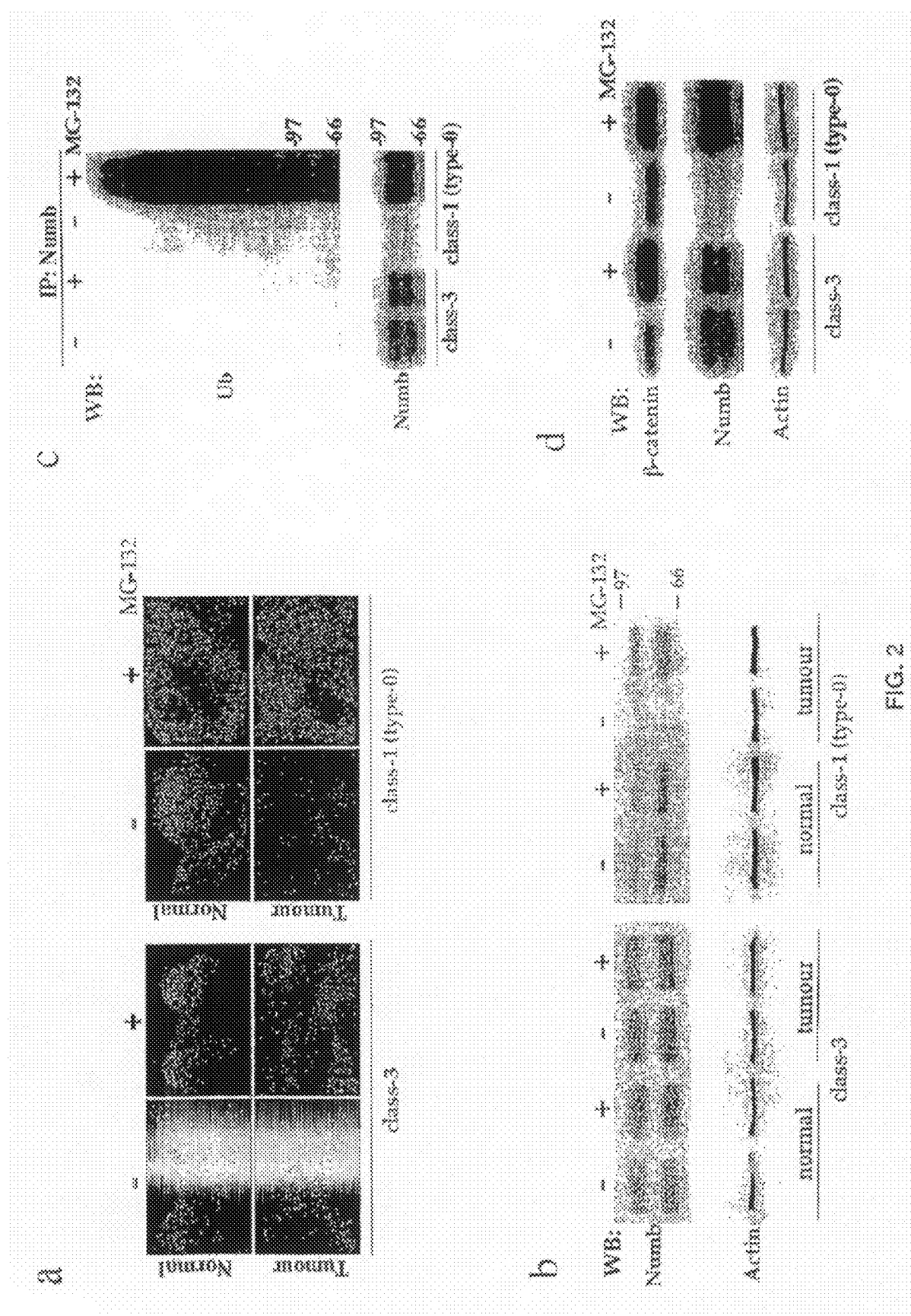

All primary cultures from normal breast, and tumour cultures from class-3 patients, displayed high levels of Numb expression, which were only marginally affected by treatment with the proteasome inhibitor MG132 (FIGS. 2a,b). In striking contrast, primary cultures from class-1 (type-0) patients, displayed little, if any, basal Numb expression, which was however restored to high levels by treatment with MG132 (FIGS. 2a,b).

Reduction of Numb levels in class-1 tumours did not appear to be the consequence of a generally increased proteasomal activity, as the basal levels of other cellular proteins also regulated by the proteasomal degradative machinery, such as beta-catenin, were not affected under the same experimental conditions (FIG. 2c).

Ubiquitin-promoted proteasomal degradation has been proposed to represent a major mechanism for cellular regulation of Numb[14]; thus, we investigated the pattern of Numb ubiquitination in tumour cells. As shown in FIG. 2d, by comparing class 1 (type-0) and class 3 tumour cells, we evidenced how the restoration of Numb levels, in class 1, by treatment with MG-132 for 6 h, was accompanied by a dramatic increase in Numb polyubiquitination. Conversely, no effect was evident in class 3 tumours. Taken together, these results provide compelling evidence that enhanced ubiquitination and increased proteasome-mediated degradation, in a sizable fraction of mammary tumours, account for the loss of Numb expression.

Example 4

Figure 3:
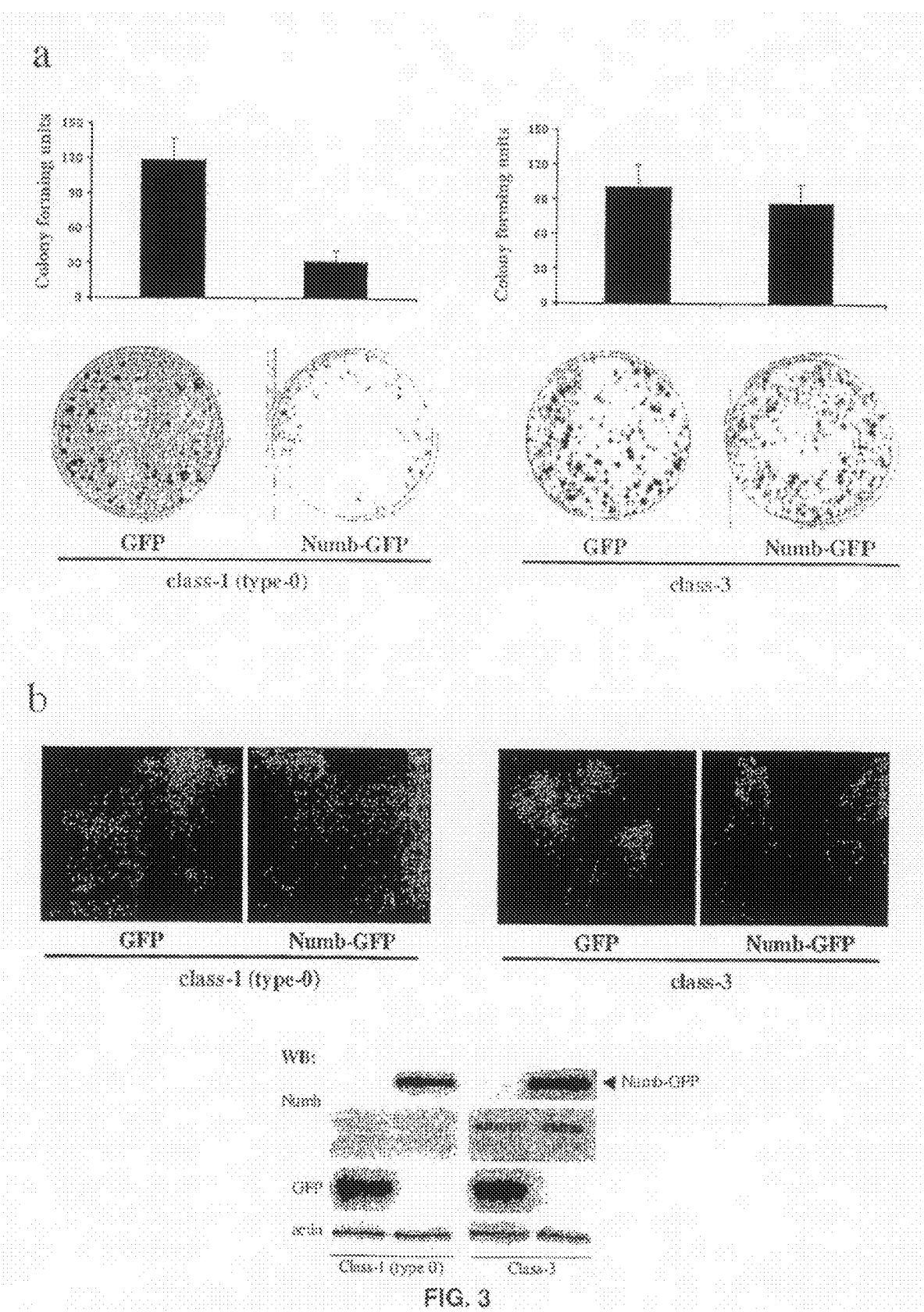

The above results support the possibility that enhanced degradation of Numb is causally involved in the progression of breast cells towards malignancy. Thus, we tested the consequences of restoration of Numb levels in primary tumour cells. Retrovirally-mediated overexpression of a fusion Numb-GFP protein in primary cells from class-1 tumours resulted in a dramatic growth-suppression effect (FIG. 3a). Conversely, class-3 tumour cells were unaffected, despite similar levels of Numb-GFP expression upon transient infection (FIGS. 3a,b).

Of note, upon transient retroviral delivery of Numb-GFP, a more rapid disappearance of the green fluorescence could be observed in class-1 (type-0) tumour cells, in comparison with class-3 tumour cells; while we could not detect any difference in the disappearance of epifluorescence in cultures transfected with GFP only (not shown). We circumvented this problem, which might have potentially affected the growth-suppression assay, by re-infecting all cultures with freshly produced virus every three days, for the entire duration of the assay (see Methods). However, the result further argues in favour an exaggerated rate of Numb degradation in Numb-negative tumours.

Example 5

Overall, therefore, these results point to a direct link between increased degradation of Numb and uncontrolled cell proliferation.

The biological antagonism between Numb and Notch provided a testable hypothesis to investigate the mechanisms triggered by the lack of Numb activity in tumours. Notch receptors act as oncogenes in models of experimental carcinogenesis both in vivo and in vitro [4-6, 15] and have been associated to human cancers, as well[8, 10]. If the lack of Numb in tumours were to cause an unregulated activity of Notch, this should be detectable by readouts of Notch activity.

Notch is activated through a series of proteolytic cleavages, ultimately leading to the release from the plasma membrane of its soluble intracellular domain (ICD)[16, 17]. The ICD is translocated to the nucleus, where it interacts with a DNA binding-protein of the CSL family (*Drosophila* Suppressor of hairless, Su(H), or its mammalian homologue RBP-Jk/CBF-1), converting it from a repressor into an activator of transcriptions[18, 19].

The biochemical mechanisms through which Numb antagonises Notch are not yet clear; however, one leading hypothesis is that direct binding of Numb to Notch prevents nuclear translocation, and hence transcriptional activity, of the ICD[1, 2, 20].

Figure 4:
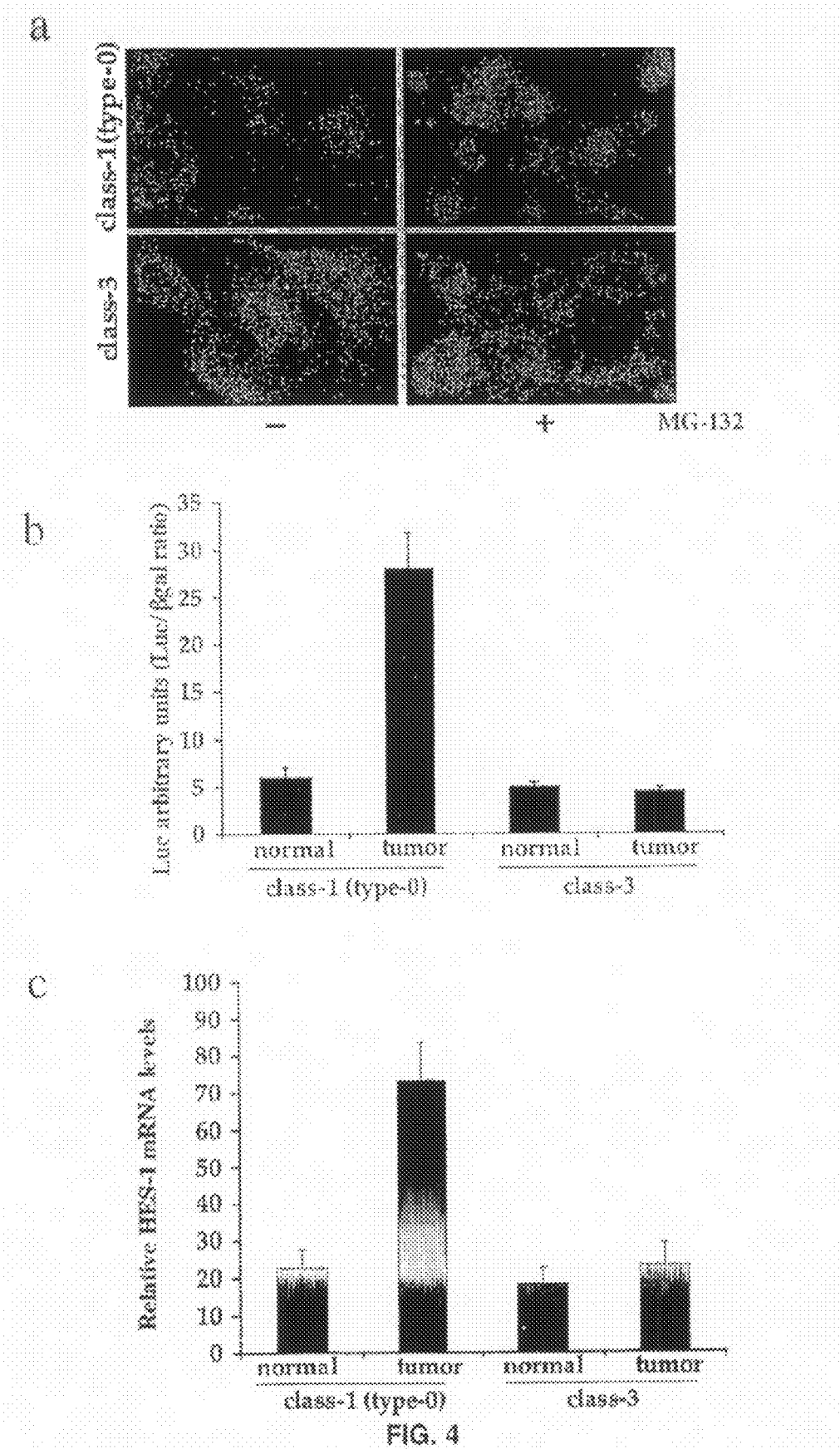

We employed primary tumour cells to monitor the subcellular distribution and the state of activation of Notch. In class-1 (type-0), Notch immunostaining appeared lower than in class-3 tumours or in normal cells (FIG. 4a). We reasoned that this finding might be consistent with increased processing of Notch at the plasma membrane followed by increased nuclear translocation of the ICD into the nucleus, whereby it is promptly degraded by the nuclear proteasomal machinery. Indeed, even a very short MG132 treatment (1 h), was able to unmask nuclear accumulation of Notch (ICD) in all class-1 (type-0)cells, but not in class-3 tumours and in normal counterparts (FIG. 4a). We measured Notch function by following luciferase activity driven from a Notch-dependent CBF1-responsive reporter (6×-RBP-Jk-luc), transfected into primary cultures. Luciferase activity was very comparable among class-3 and normal cultures, and strikingly increased in all class-1 cultures (FIG. 4b).

Finally, by using quantitative RT-PCR, we found that endogenous expression of the HES-1 mRNA, a known target gene for Notch transcriptional activity[19,21] was significantly higher in class-1 tumour cells, in comparison to class-3 cells or to their normal counterparts (FIG. 4c).

Figure 5:
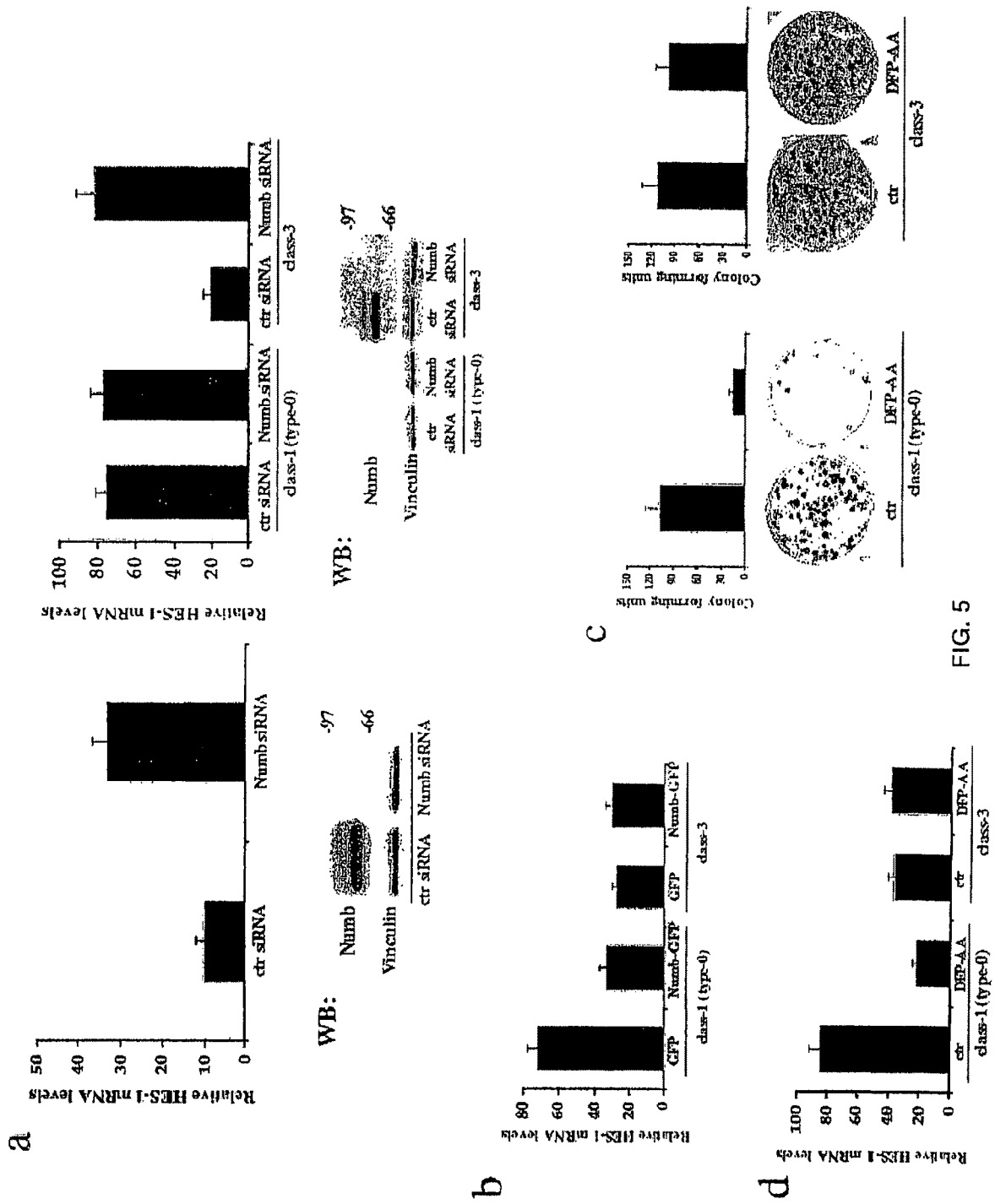

These results prompted us to assess directly a possible functional link between Numb levels and Notch activity in tumour cells. RNAi-mediated silencing of Numb in primary normal breast cells resulted in a significant increase in HES-1 mRNA transcripts, in comparison to cells transfected with a control siRNA (FIG. 5a). A similar increase in Notch-dependent transcriptional activity was observed in class-3 tumour cells, but not, as expected, in class-1 tumour cells (FIG. 5a). Accordingly, retrovirally-mediated overexpression of Numb caused a significant decrease in basal Notch activity in class-1, but not in class-3 tumour cells (FIG. 5b) or in normal cells from the same patients (data not shown). As overexpression of Numb in class-1 tumour cells also caused a significant growth-suppression effect (FIG. 3), we directly tested the possibility that a deregulated Notch activity, downstream of loss of Numb, might be responsible for uncontrolled cell proliferation in class-1 tumours. We took advantage of the small-molecule peptidomimetic presenilin-inhibitor DFP-AA, which blocks Notch signalling[22], and effectively suppresses the growth of Notch1-transformed lymphoid cell lines in vitro[23]. DFP-AA treatment of class-1 tumour cells was sufficient to cause a dramatic suppression of their growth potential (FIG. 5c), which was paralleled by a marked decrease in Notch activity, as assessed by HES-1 mRNA levels (FIG. 5d). In contrast, no significant effect was observed in class-3 tumour cells (FIGS. 5c,d).

Example 6

The association between survival and Numb expression was assessed in the set of breast cancer patients described above. P53 and ER status were assessed by immunohistochemical analysis on paraffin sections.

Figure 6:
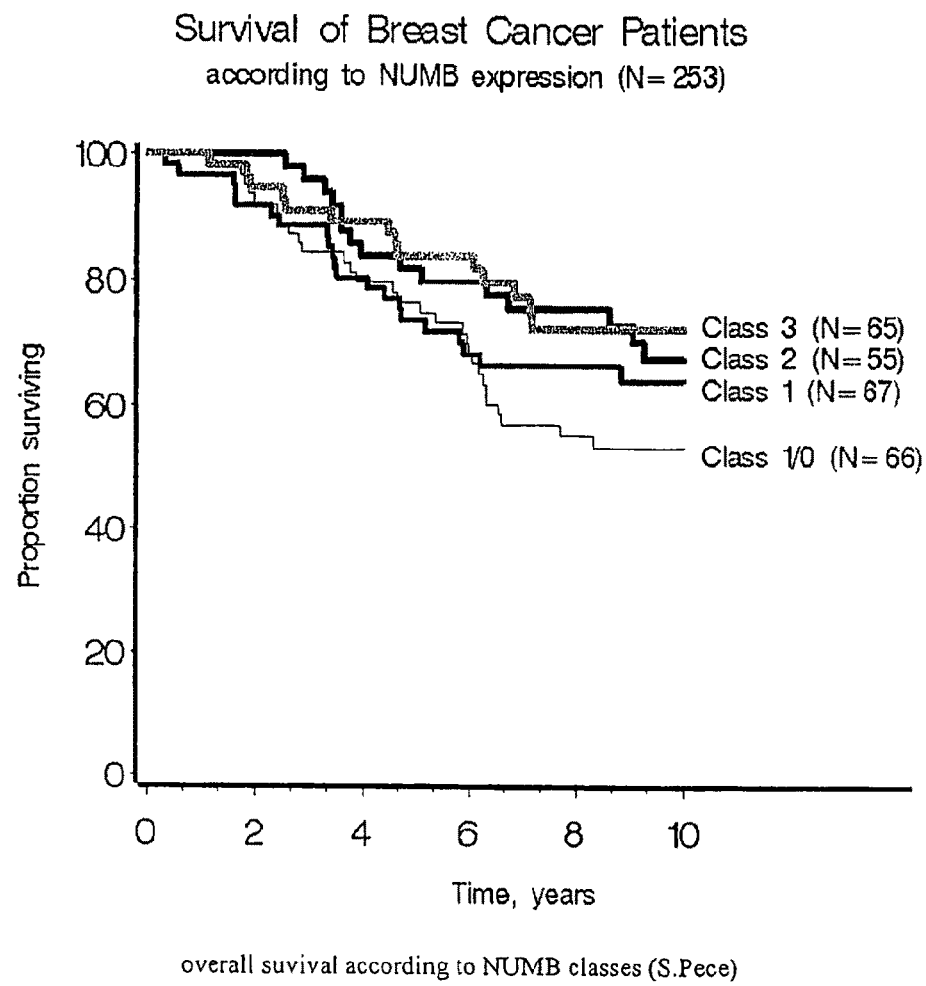
FIG. 6 and FIG. 7 show survival of breast cancer patients according to Numb levels, on a Kaplan Meier Plot.
Figure 7:
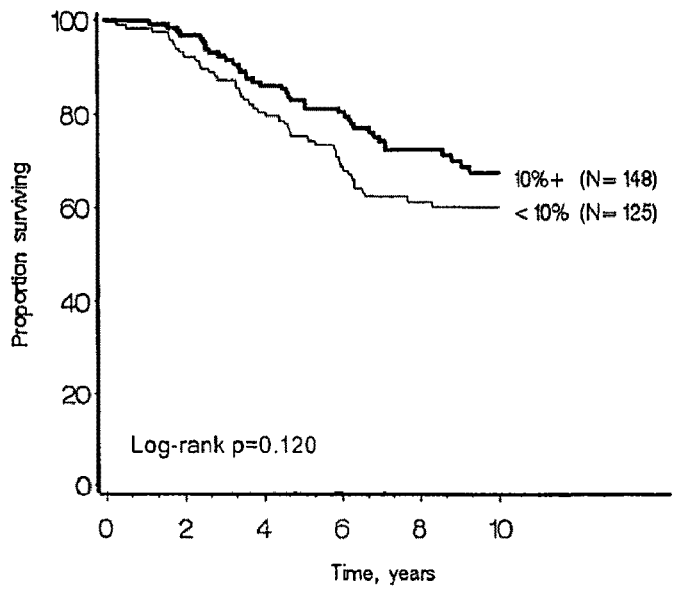

Using a Kaplan Meier Plot, FIGS. 6 and 7 show a trend towards reduced survival with reduced levels of Numb over a ten year period.

Figure 8:
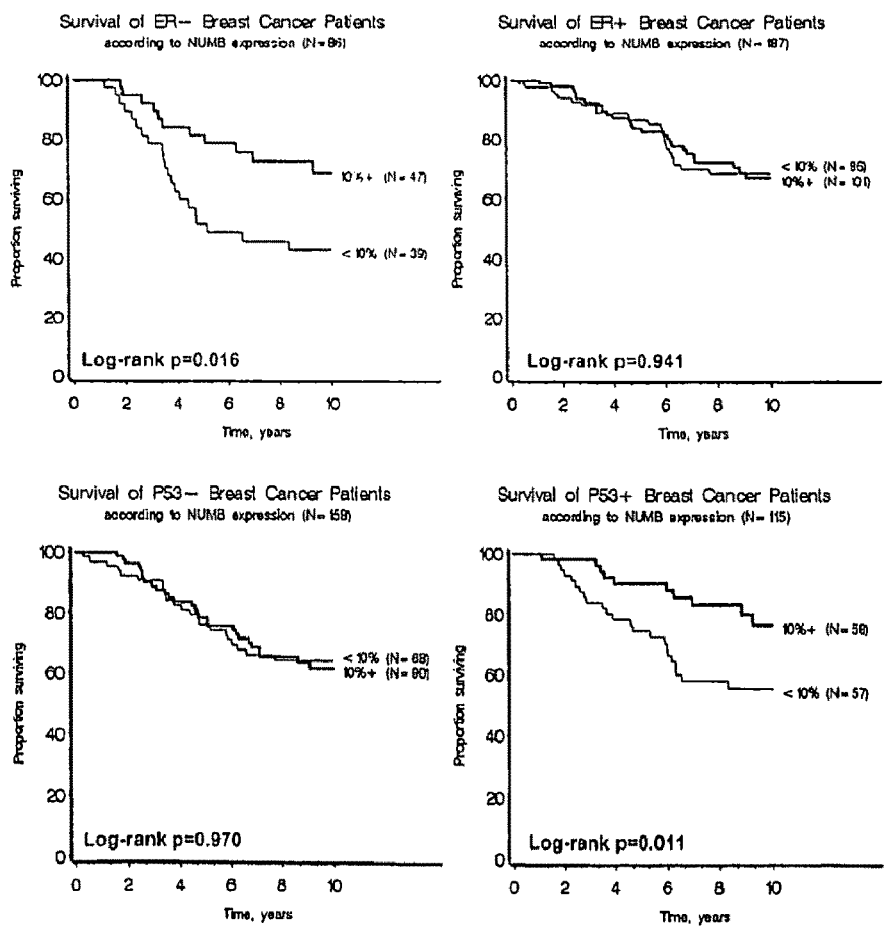
FIG. 8 shows survival of breast cancer patients according to Numb levels and according to ER or p53 status.

Results were then analysed according to Numb expression and ER or p53 status. Results are shown in FIG. 8. A trend towards lower survival with reduced Numb expression is seen both in ER– and P53+ patients.

Figure 9:
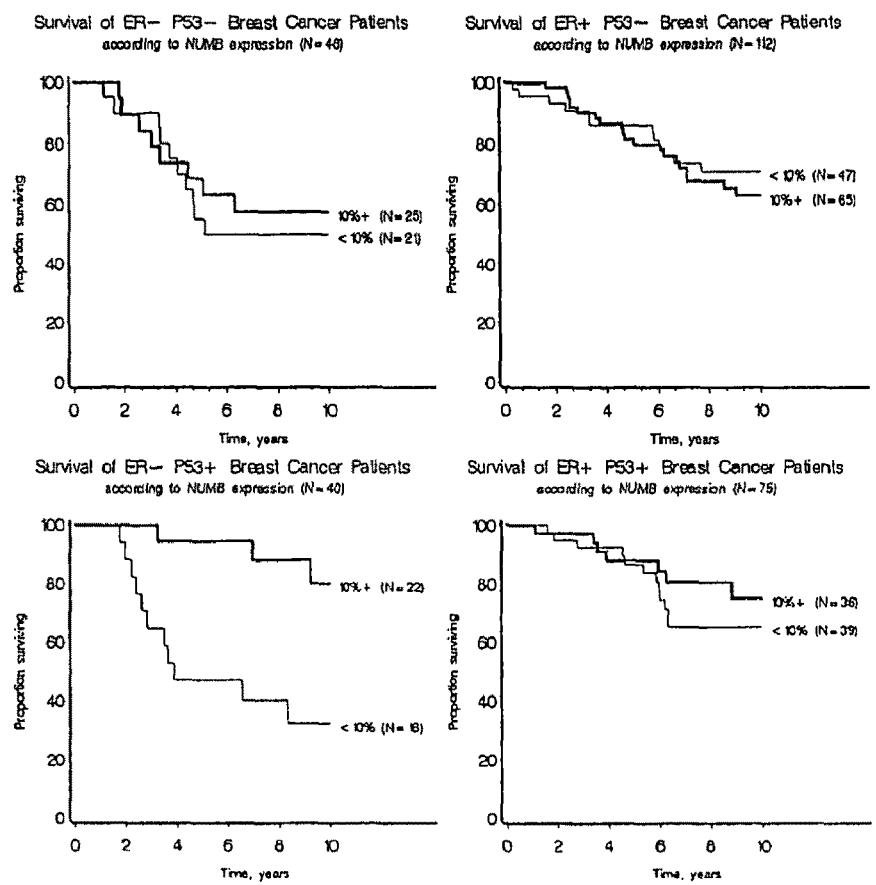
FIG. 9 shows survival of breast cancer patients according to Numb levels, ER and p53 status.

FIG. 9 shows the results obtained when considering both ER and p53 status. A dramatic difference in survival according to Numb expression is seen in ER–/p53+ patients.

The prognostic value of Numb was assessed using the Cox proportional hazards regression, with adjustment for tumour stage (pT=1 vs pT>1).

The table below shows that the proportion of tumours of small dimensions(T=tumour size), classified as T1 and featured by a better prognosis, is reduced in ER-patients bearing cancers with low Numb levels (NUMB<10%), whereas the percentage of T1 tumours is higher in ER-patients with NUMB ≧10%. Indeed, as shown in the second table below, Numb levels correlate with pT (tumour size) in ER− but not in ER+ patients, independently of p53 status.

As the tumour size is a well-recognized prognostic parameter for poor prognosis, by using the Cox proportional hazards regression statistics, it was necessary to ascertain that in ER−P53+ tumours, lack of expression of NUMB (<10%) was indeed associated with a poor survival even after adjustment for tumour stage (pT=1 vs pT>1). In other wards, the worse prognosis in ER−p53+ prognosis in patients with low Numb levels (NUMB<10%) is not a consequence of a greater tendency to form tumours of bigger dimensions, but is specifically correlated to lack of Numb protein.

Proportion of tumours classified as T1

| % T1 tumours | ER− P53− | ER+ P53− |
|---|---|---|
| NUMB < 10% | 35% | 73% |
| NUMB ≧ 10% | 54% | 73% |

| % T1 tumours | ER− P53+ | ER+ P53+ |
|---|---|---|
| NUMB < 10% | 28% | 67% |
| NUMB ≧ 10% | 67% | 75% |

In ER− P53+ tumours, lack of expression of NUMB (<10%) is associated with a poor survival even after adjustment for pT (HR=4.6 ; 95% CI=(1.4-15.6), p=0.013).

NUMB is correlated with pt in ER− tumours but not ER+ tumours.

| | ER− | | ER+ | |
|---|---|---|---|---|
| | pT1 | pT2-pT4 | pT1 | pT2-pT4 |
| NUMB < 10% | 12 | 26 | 57 | 24 |
| NUMB ≧ 10% | 26 | 17 | 73 | 26 |
| | P = 0.014 | | P = 0.62 | |

SUMMARY

The sum of our results clearly shows that deregulation of Numb-mediated control on Notch signaling is a major occurrence in human breast cancers.

Loss of Numb expression leads to activation of Notch, which in turn is responsible for increased proliferation of tumour cells. Accordingly, restoration of physiological Numb levels, or inhibition of Notch activity, reverted the hyperproliferative state in Numb-negative tumours.

Importantly, Numb-positive tumours were unaffected by these manipulations. Thus, Numb and Notch fulfill the operational definitions of oncosuppressor and oncogene, respectively, in human breast cancers. Loss of Numb expression in the examined breast cancers is due to its increased ubiquitination with ensuing proteasomal degradation. There is precedent for this kind of alteration of oncosuppressor proteins. For example, increased ubiquitination/degradation of p53 might underlie the loss of normal p53 function found in many tumours with a wild-type p53 gene[24,25].

This raises the issue of which is the putative genetic lesion upstream of Numb, in human breast cancers. An obvious possibility is that there are increased levels/activity of an E3-type ubiquitin ligase, consistently with findings that Numb levels are regulated by E3-ligases, such as LNX, Siah-1 and Mdm2[14,26,27].

Alternatively, increased Numb phosphorylation might cause its ubiquitination and degradation, as a strong correlation between these two post-translational modifications has been shown for other proteins [28,29].

Of note, in *Drosophila*, a serine/threonine kinase, NAK, physically interacts with Numb and causes loss-of-Numb-function phenotypes upon overexpression[30]. Under this scenario, the primary lesion would affect a serine/threonine kinase (Numb is serine/threonine phosphorylated[13]), rather than an E3-ligase.

Whatever the case, restoration of Numb function might be obtained by pharmacological inhibition of the enzyme(s) responsible for its degradation: an obviously appealing therapeutic possibility.

In summary, our study establishes in an ex vivo model, highly representative of the actual in vivo setting, that loss of Numb participates to tumourigenesis through unregulated Notch activity.

Example 7

We used a cDNA subtraction approach to clone genes whose expression is induced by E1A, concomitantly to its induction of re-entry in the cell cycle of TD myotubes.

TD C2C12 myotubes were infected with either the adenovirus dl520 (expressing only the 12S mRNA of E1A) or the control adenovirus dl312 (expressing no E1A mRNA). Only the dl520 infected myotubes dispayed 48h p.i. S-phase re-entry phenotype (about 70%). 2 μg of time course pooled polyA+ RNA from dl520 and dl312 infected myotubes was used as starting material for cDNA retro-transcription (Invitrogen) and subtraction procedures (Clonetech) to obtain a library of about 800 of clones.

E1A induced library was screened by Reverse Northern. 14 filters (7 plates, 2 filter per plate) contained all the cloned sequences as single purified PCR bands and some controls (DNA ladder IX as negative control, adenoviral cDNA and NP95 sequence as positive control, GAPDH as internal standard). Each plate (2 filters) was hybridized in duplicate with two different labelled cDNA pools (dl520 and dl312 infected myotubes cDNA) to fish out by comparing the radioactive signals only the E1A (dl520) induced clones. The single positives clones were picked, then grown and sequenced to retrieve by blast analysis the corresponding gene.

Each gene was then validated by Q-RT-PCR onto RNA from E1A and mock infected myotubes.

Specifically, the Reverse Northern positive E1A induced genes are validated by SYBR GREEN based quantitative RT PCR on RNA from E1A (dl520) infected TD C2C12 myotubes, proliferating (MYB) C2C12 myoblasts, E1A (dl520) infected TD MSC (mouse satellite cells) and proliferating (MYB) MSC myoblasts.

FIG. 10 shows the results of the validation. It shows 55 non-redundant clones of which 29 (henceforth referred to as E1A-induced genes) showed reproducible, and greater than 2-fold, induction, upon E1A expression in both TD C2C12 mouse myotubes and primary TD muscle satellite cells (MSC).

All the fold values are calculated using as reference mock infected (dl312) myotubes (value 1.00) and as standard mouse GAPDH gene. The values are expressed as average of two independent experiments and standard deviation (SD).

The 29 E1A induced display different timing of induction after E1A expression onto TD C2C12 myotubes. Two time points were considered: 24 h/EARLY (soon after E1A protein starts accumulating) and 36 h/LATE (immediately before S-phase re-entry). The transcriptional activation of each gene was measured as E1A (dl520) fold induction referred to mock infected myotubes (dl312) of two independent experiments by SYBR GREEN based Q-RT-PCR. A mathematical ratio calculated between 24 h/EARLY and 36 h/LATE E1A induction defined the timing of activation. EARLY=>0,4; LATE=<0,4.

Of the 29 genes, 14 genes were early-induced and 15 were late-induced by E1A (FIG. 11).

Of interest, almost all of the E1A-induced genes, were actively transcribed in proliferating myoblasts, indicating that the E1A-induced program proceeds through the reactivation of programs switched off by terminal differentiation and withdrawal from the cell cycle (FIG. 10).

Example 8

E1A exerts pleiotropic effects on TD myotubes. It suppresses tissue-specific genes, through its binding to the transcriptional co-activators p300/CBP and MyoD, and reactivates the cell cycle, through a mechanism in which binding to pocket proteins (mainly pRb and p130) and restoration of E2F activity is pivotal. However, the ectopic expression of E2Fs in TD myotubes does not induce S phase, indicating that other E1A-activated pathways are concomitantly needed. Indeed E1A-regulated pocket/Rb-independent mechanisms are known, which involve CycE/CDK2-, CtBP-, TRAPP- or p400-regulated pathways, and other chromatin remodelling activities. While it is unclear how these activities contribute to the creation of a S-phase environment, there is evidence that some of these pocket/E2F-independent pathways contribute to E1A-mediated oncogenesis. In keeping with our initial strategy, we tried therefore to classify the E1A-induced genes according to their upstream mechanism of regulation.

We employed three strategies in TD myotubes: i) overexpression of E2F1, to identify those genes whose induction is E2F1-dependent, using Ad-E2F1 adenovirus infection (MIO 300) as described in Pajalunnga et al 1998; ii) expression of an E1A mutant (YH47/dl928) that is unable to bind to pocket proteins, to identify genes whose induction is dependent on the interference of E1A with pocket protein activity; iii) removal of the Rb gene in TD myotubes derived from MSC from Rb-floxed mice (Vooijs et al 1998). In this latter case, removal of Rb by Cre recombinase was obtained after the induction of terminal differentiation, in an attempt to mimic the effects of E1A exclusively dependent on interference with Rb.

We analysed the expression of the E1A-induced genes under these conditions using Q-RT-PCR, in comparison to the levels obtained upon expression of E1A (FIG. 11).

Total RNA was isolated with the Triazol method (Invitrogen). Two μg of RNA were used, with 100 ng of random examers, in a reverse transcription reaction (SUPERSCRIPT II, Invitrogen). One-tenth ng of cDNA was amplified, in triplicate, in a reaction volume of 20 μL with 10 pMol of each gene specific primer and the SYBR-green PCR MasterMix (Applied Biosystems). Real-time PCR was carried out on the ABI/Prism 7700 Sequence Detector System (Perkin-Elmer/Applied Biosystems), using a pre-PCR step of 10 min at 95° C., followed by 40 cycles of 15 s at 95° C. and 60 s at 60° C. Specificity of the amplified products was confirmed by melting curve analysis (DISSOCIATION CURVE™ Perkin-Elmer/Applied Biosystems) and by 6% PAGE. Preparations with RNA template without reverse transcriptase were used as negative controls. Samples were amplified with primers for each genes (for details see Q-PCR primer list below) and GAPDH as a housekeeping gene (other housekeeping genes, including rRNA 18S and beta-actin were also tested with comparable results). The Ct values were normalized to the GAPDH curve and the relative expression of each gene was expressed as the ratio relative to mock (dl312) infected myotubes.

The following major classes of genes could be identified:
Class A. Pocket-dependent (not induced by YH47, strongly induced by Rb removal), E2F1-dependent (strongly induced by E2F1 overexpression) genes (7 genes).
Class B. Pocket-dependent, E2F1-independent (or scarcely-dependent) genes (8 genes).
Class C. Pocket-indifferent (well-induced by YH47, but also activated by Rb removal). This group of 9 genes is clearly subjected to dual redundant regulation, both pocket-dependent and -independent. Almost all of these genes are E2F1-independent, with the exception of KIAA0648.
Class D. Pocket-independent (or substantially-independent) genes. This group of 6 genes is well activated by YH47 and scarcely by Rb removal. In addition almost all of them are E2F1-independent, with the marginal exception of KIAA0097.

A first genetic cluster, comprising class A and B genes, is constituted by "typical" E1A-responsive genes, whose induction is stringently pocket protein-dependent (regardless of the E2F1-dependence). All the early-induced genes belong to this group. Of interest, a subset of genes in this genetic cluster (MCM7, MCM4 and MIS5), which is widely known to be under the transcriptional control of E2F1 in non-post-mitotic cells, does not seem to be responsive to the overexpression of this protein in a TD environment, despite retaining pocket protein-dependence. This result suggests there is a difference in the transcriptional regulation of pocket/E2F genes in reversibly and irreversibly arrested cells, and provides a tentative hypothesis as to why E2Fs are unable to force the re-entry in the cell cycle of TD cells.

A second genetic cluster (class C and D) is made up of pocket-indifferent or pocket-independent genes. It is not clear why all these genes are "late" genes, albeit the correlation is too strong to be due to chance. More importantly, within this cluster, class D genes constitute a transcriptional signature, induced by a well-defined genetic alteration, through a yet unknown mechanism. Since pocket-protein/E2Fs-independent mechanisms are known to contribute to E1A-induced tumourigenesis(Alevizopoulos et al., 1998; Alevizopoulos et al., 2000; Deleu et al., 2001; Dorsman et al., 1995; Fuchs et al., 2001; Sandmoller et al., 1996; Subramanian et al., 1988), our hypothesis would predict a major involvement of the class D gene signature in human cancers.

Example 9

We directly tested this possibility by in situ hybridisation on tissue microarrays (TMA) containing hundreds of tumour samples derived from ten different tumours, along with their matched normal counterparts. Fifteen E1A-induced genes were tested, including representatives from all classes. Strikingly all the six class D genes were overexpressed in a significant fraction of cancers, when compared to normal matched tissues (FIG. 12a). In addition, there was no significant correlation between the tumour proliferative index (as assessed by immunostaining with anti-Ki-67) and the levels of four of six class D genes (SKIN, RRIP/TRPC4AP, SMU-1 and ch-TOG/KIAA097), indicating that the overexpression event is not the consequence of the tumour hyperproliferative state (not shown).

This contention was further supported by the finding that four of six class D genes (SKIN, DDX21, RRIP/TRPC4AP and SMU-1) did not behave as cell-cycle regulated genes, while all the Class-A and class-B genes were cell cycle-regulated, and class C marginally cell cycle-regulated.

Overall, 15 E1A-induced genes, from all classes, were tested by TMA analysis. In particular, LBR, XTP1, MGC22679, K1594, C30rf4, CML66, FLJ37652 showed low or absent expression in both normal and tumour tissues, indicating that their expression level was below the detection limit of the in situ hybridization technique. Two of the class B genes tested (Np95 and Nasp), showed overexpression in tumours. However, comparably high levels of expression were detected also in the proliferating cells of the normal tissues. Thus Np95 and Nasp cannot be considered truly overexpressed, and their expression probably reflects simply the tumour hyperproliferative state. However, these data do not rule out the possibility that all these genes may still distinguish good and poor prognosis tumour samples using different techniques, especially considering the high proliferative index of very aggressive tumours. Moreover, it is possible that the protein levels of these genes are altered in tumour samples.

The involvement of the identified cancer signature (class D genes) in the natural history of the tumours was further validated in three sets of experiments. First, we analysed a colon cancer progression TMA containing normal epithelia, hyperplastic polyps, adenomas and adenocarcinomas. All six class D genes were overexpressed in 45-75% of adenocarcinomas. The expression of three genes (SKIN, SMU-1, CH-TOG/KIAA097) showed absolute correlation with frank adenocarcinomas (FIG. 13), whereas RRIP/TRPC4AP was also expressed in other conditions, despite being significantly more expressed in tumours. (FIG. 13). Of note, SF3B1 was also overexpressed in adenomas (FIG. 13), albeit with overall less intense staining than in adenocarcinomas (not shown), consistent with the possibility that its overexpression represents an early event in tumour progression. DDX21 is also overexpressed in adenomas.

Second, we extracted data regarding class D E1A-induced genes from data sets of expression profile screenings performed on a large number of breast samples. Two independent data sets were employed, one published by Van't Veer et al (van't Veer et al, Nature 415(31), 530-353, 2002) and one generated in-house. In particular, we focused our attention on a subgroup of tumours with no lymph nodes involvement at surgery, which either developed metastatic disease (N0+ patients) or stayed disease-free (N0-patients) over a 5 year follow-up period. Three Class D genes (SKIN, ch-TOG and RRIP) were able to predict the risk of disease relapse with a ~70% accuracy (FIG. 14 A-B). The Class D genes were able to predict the risk of disease relapse with a p-value <0.05 on the data set generated in-house and a p-value <0.04 on the data set from van't Veer. The predictive strength of the 3-genes model was further confirmed by Q-RT-PCR (p-value 0.003) on 15 randomly selected breast tumor patients (all lymph node negative at diagnosis), which were all homogeneous for estrogen receptor status (Er pos) (FIG. 14C).

Patients having enhanced expression of ch-TOG and SKIN and a reduced expression of TRPC4AP were designated as having a poor prognosis, whereas patients with a reduced expression of ch-TOG and SKIN and an enhanced expression of TRPC4AP were designated as having a "good" prognosis.

Since the potential use of class A/B/C as prognosis predictors is a viable option, their predictive ability was tested on a subgroup of tumours with no lymph nodes involvement at surgery, which either developed metastatic disease (N0+ patients) or stayed disease-free (N0-patients) over a 5 year follow up period analysed by Affymetrix. Class A+Class B+Class C genes were able to predict the risk of disease relapse (p-value <0.004, FIG. 14D).

Finally we tested whether class D genes were able to confer a proliferative advantage to tumour cells. As a proof of principle, we focused on the SKIN gene, which showed the most consistent and solid behaviour in all the above described characterizations. The frequent genetic alterations at the SKIN locus predict a mechanistic involvement of this gene in malignant transformation. If so, SKIN overexpression should confer a proliferative advantage to the cell and its functional ablation should revert this phenotype. In order to test this possibility, we selected six cell lines to perform SKIN knock down (KD) by siRNA. Three of the cell lines (HT-29, SKMEL5, and SKBR3) displayed SKIN overexpression (FIG. 15 B-C). Three other tumour cell lines (DLD1, SKMEL28, and MDA-MD415) showed normal levels of SKIN expression (FIG. 15 B-C). Of note, tumour cell lines were selected to represent matched samples (overexpressing/not overexpressing) from the same type of tumour: colon carcinoma (HT29 and DLD1), melanoma (SKMEL28 and SKMEL5) and breast carcinoma (SKBR3, and MDA-MB-415). As shown in FIG. 15A, the KD of SKIN expression by siRNA dramatically reduced proliferation of all the overexpressing cell lines, whilst a control scrambled oligo had little, if any, effect. Importantly, SKIN KD did not inhibit proliferation of tumour lines displaying no overexpression of SKIN (FIG. 15A).

A survey of cancer microarray data, available in the public domain (www.oncomine.org), also revealed overexpression of some class-D genes in certain tumours. The results of a meta-analysis regarding class D genes, performed using the ONCOMINE web tool to check for significant regulation of Class-D genes in published expression profile experiments, are shown in FIG. 16. SKIN (flj23790) analysis could not be performed successfully, since the specific probeset for SKIN is present only in some of the more recent array versions (Affymetrix HG-U133 chip B and HG-U95 chip B) therefore drastically reducing the database size. TRPC4AP did not reach statistical significance.

FISH Analysis of SKIN was also performed. Genetic alterations at the SKIN locus (on chromosome 8) were sought. Since overexpression is frequently due to increased gene dosage, we focused on SKIN gene amplification. Initially, several cell lines were screened by FISH on metaphase-blocked cells. Multiple SKIN-specific signals were detected in several tumour cells lines (FIG. 17A), independently of their state of aneuploidy. Moreover, SKIN amplification correlated well with its overexpression in the same cell lines, both at mRNA and protein levels, (FIG. 17A). Next, SKIN amplification was analysed directly on tumour tissues by in situ interphase FISH on colon specimens. In 6 samples of normal colonic mucosa and in 8 adenomas, no amplification (and no overexpression, as judged by ISH) of SKIN was detected (FIG. 17B). In colon carcinoma, SKIN amplification (>4 signals/cell) was detected in 7 of 21 cases (33%) (FIG. 17B. Amplification was restricted to the epithelial components of the sample (FIG. 17B). In all cases SKIN amplification was accompanied by overexpression, judged by ISH (FIG. 17B). Interestingly, in a sizable fraction of non-amplified cases (6/14, corresponding to 29% of all analyzed cases), overexpression of SKIN was detected by ISH (FIG. 17B).

Thus, SKIN overexpression can occur in the presence or absence of gene amplification.

Example 10

We conducted a further screen in the same experimental conditions as before (TD C2C12 myotubes infected with either the adenovirus dl520, expressing only the 12S mRNA of E1A, or the control adenovirus dl312, expressing no E1A mRNA). Instead of using a subtraction library technique, RNAs from control/E1A expressing cells were prepared, and profiled by Affymetrix Genechip technology using standard techniques.

1134 genes were identified using this approach (including 25/30genes obtained in the subtraction screening approach).

From these genes, markers of particular value in the prognosis of breast cancer and NSCLC were identified as below:

Breast Cancer

We used the Affymetrix GeneChip technology (HG-U133 chip A+B) to perform gene expression profiling studies on RNAs prepared from biopsies of an initial group of 46 patients who were estrogen receptor positive with node negative primary carcinomas (N0) at the time of diagnosis, with a >10-year follow up.

This analysis included only patients who developed distant metastases within 5 years (20 cases) and patients presently disease-free (26 cases) after a 7.5-12 years period since the resection of the primary tumour.

The values of expression of more than 30,000 genes for each patient were stored and organised as "breast cancer" dataset, as follows.

The Human Genome U133 (HG-U133) Set, consisting of two GeneChip® arrays, contains almost 45,000 probe sets representing more than 39,000 transcripts derived from approximately 33,000 well-substantiated human genes. This set design uses sequences selected from GenBank®, dbEST, and RefSeq.

The sequence clusters were created from the UniGene database (Build 133, Apr. 20, 2001). They were then refined by analysis and comparison with a number of other publicly available databases including the Washington University EST trace repository and the University of California, Santa Cruz Golden Path human genome database (April 2001 release). The HG-U133A Array includes representation of the RefSeq database sequences and probe sets related to sequences previously represented on the Human Genome U95Av2 Array. The HG-U133B Array contains primarily probe sets representing EST clusters.

Affymetrix® Microarray Suite version 5.0 was used to normalised and pre-filter the data, with the following procedure:

The detection algorithm of the software was used to calculate a Detection p-value (see Manual for further details) and assign a Present, Marginal, Absent call of the signal for each spot on the array. Features (gene) always called Absent in every arrays were excluded.

The intensity signal of each transcript probed on the array, should be more than 200 (the range of signal is normally between 10 and 20.000) after MAS5 computing and normalisation.

The median intensity of the signals of all the transcripts probed (probe pairs) on the array was computed (global median) and this value is used to divide again the signal of each probe pair. This procedure is called Chip normalisation.

The median value of a gene probed on different arrays is computed and used to divide the Chip normalised signal of the same gene. This procedure is repeated for every other gene. This is called Gene normalisation.

Having obtained the "breast cancer dataset" as described above, we reduced the initial list of 1134 E1A induced genes by filtering out all those genes showing a fold change <1.5 between the patients who developed metastasis within 5 years, and the patients still free of disease during the long-term follow up.

Then, we ranked the gene list based on their power to correctly classify the patient outcome (poor prognosis Vs. good prognosis) using the leave-one-out cross validation (KNN-9) statistical algorithm, as follows.

The 1134 gene list was reduced to a number of 200 genes, with the following procedure in Genespring 6.2® environment:

1. The class prediction isolates a gene.
2. For each sample, it calculates the probability of obtaining the observed number of samples from each class above and below that cutoff mark by chance, using Fisher's exact test (hypergeometric distribution).
3. Selects the smallest p-value calculated in step 2 and converts it into prediction strength by taking negative natural log of the p-value.
4. Repeats steps 1 to 3 until prediction strengths for all genes on selected gene list are calculated.
5. Ranks the genes according to their predictive strength for each class (200 genes).
6. Genes with highest predictive strength for each class are selected equally to generate a final list of best predictor genes. The final number of best predictors is user-specified (13 genes).

Genespring 6.2® (www.silicongenetics.com) was used to perform the analyses.

The top ranked 13genes were then selected, and are shown in the table below.

TABLE 2

| UGCluster | Name | Symbol | LLID | UGRepAcc | LLRepProtAcc | Cytoband |
|---|---|---|---|---|---|---|
| Hs.444372 | GDNF family receptor alpha 1 | GFRA1 | 2674 | AF038421 | NP_665736 | 10q26 |
| Hs.125180 | growth hormone receptor | GHR | 2690 | NM_000163 | NP_000154 | 5p13-p12 |
| Hs.408182 | collagen, type II, alpha 1 (primary osteoarthritis, spondyloepiphyseal dysplasia, congenital) | COL2A1 | 1280; 4670 | NM_001844 | NP_149162 | 12q13.11-q13.2 |
| Hs.302634 | frizzled homolog 8 (Drosophila) | FZD8 | 8325 | AB043703 | NP_114072 | 10p11.22 |
| Hs.408658 | cyclin E2 | CCNE2 | 9134 | NM_057749 | NP_477097 | 8q22.1 |
| Hs.174312 | toll-like receptor 4 | TLR4 | 7099 | NM_003266 | NP_612567 | 9q32-q33 |
| Hs.23900 | Rac GTPase activating protein 1 | RACGAP1 | 29127 | NM_013277 | NP_037409 | 12q13.12 |
| Hs.305971 | solute carrier family 2 (facilitated glucose transporter), member 10 | SLC2A10 | 81031 | AF248053 | NP_110404 | 20q13.1 |

TABLE 2-continued

| UGCluster | Name | Symbol | LLID | UGRepAcc | LLRepProtAcc | Cytoband |
|---|---|---|---|---|---|---|
| Hs.165904 | epsin 3 | EPN3 | 55040 | AK000785 | NP_060427 | 17q21.33 |
| Hs.421337 | DEP domain containing 1B | DEPDC1B | 55789 | BC019075; NM_018369 | NP_060839 | 5q12.1 |
| Hs.512638 | TBP-interacting protein | TIP120A | 55832 | NM_018448 | NP_060918 | 12q14 |
| Hs.369055 | ATP-binding cassette, sub-family G (WHITE), member 1 | ABCG1 | 9619 | NM_207630 | NP_997513 | 21q22.3 |
| Hs.409034 | collagen, type XV, alpha 1 | COL15A1 | 1306 | NM_001855 | NP_001846 | 9q21-q22 |

The predictor is able to determine the risk to develop metastasis within 5 years. FIG. 18A shows the probability of remaining metastasis free of patients with good or poor expression signatures, based on this set of 13 genes, using the "breast cancer dataset" as described above.

For each of the 13 genes described herein, upregulation is associated with a poor prognosis. Patients were considered as having a "good" signature if they had lower values of at least 7 of the 13 genes, compared to other individuals in the sample (the "poor" group).

A significant difference was found in the risk of metastasis in the two groups, using the Log-rank test to calculate P-values.

FIG. 18B shows the probability of remaining metastasis free of patients with good or poor expression signatures, based on a predictor of Van't Veer LJ (as above).

Using a dataset of 67 patients including those which are both estrogen receptor positive and negative (including the 46 patients previously described) the 13 gene predictor of the present invention is able to identify four more patients which went on to develop metastasis, as compared to the Van't Veer predictor. Using the 46 ER positive patients, it is able to correctly identify 6 more patients as compared to the Van't Veer dataset.

Using the Van't Veer dataset as a test dataset, the percentage of unsuccessfully classified samples has been found to be comparable between the two predictors.

It is important to note that the Van't Veer predictor comprises 70 genes, whereas the present predictor makes use of only 13. The ability to use a smaller set of genes without comprising accuracy is important in the clinical application of the predictor, diminishing costs and allowing a larger range of techniques to be used. Alternatively, more genes could be added to the set to provide a further improvement in accuracy.

The expression profile of the 13 breast gene predictor on 36 N0 breast cancer patients analysed by Affymetrix was further confirmed by Q-RT-PCR (FIG. 18C). The classifier performance was also confirmed by Q-RT-PCR. Q-RT-PCR reactions were performed using default settings suggested by Applied Biosystem.

Lung Cancer

Two of the most comprehensive NSCLCs screenings, with complete follow up information publicly retrievable (Beer, D. G., et al. Gene-expression profiles predict survival of patients with lung adenocarcinoma. Nat Med, 8: 816-824, 2002, Bhattacharjee, A., et al. Classification of human lung carcinomas by mRNA expression profiling reveals distinct adenocarcinoma subclasses. Proc Natl Acad Sci USA, 98: 13790-13795, 2001.) were downloaded from the web (www.oncomine.com). These two datasets contain RNA expression values of patients with lung adenocarcinomas from two independent cohorts, and more precisely: the Beer dataset (Affymetrix GeneChip HU6800) is composed by 23 patients with disease-free-survival (DFS) more than 52 months and 18 patients with relapse time (Dead-of-disease) less than 29 months; the Bhattacharjee dataset (Affymetrix GeneChip HG-U95Av2.1) is composed by 33 patients with DFS more than 30 months and 27 with relapse time (Dead-of-disease) less than 25 months.

The datasets were processed as follows:

Affymetrix® Microarray Suite version 4.0 normalised datasets were downloaded from the web.

All the genes and ETSs showing a negative values after normalisation were excluded from further analysis.

We considered only the genes having signal on the chip in at least 25% of the patients in each dataset.

The median value for each gene present on the array was then calculated. We retain all those genes showing a variance of at least 1.5 fold compared to the corresponding median calculated.

The median intensity of the signals of all the transcripts probed (probe pairs) on the array was computed (global median) and this value is used to divide again the signal of each probe pair. This procedure is called Chip normalisation.

The median value of a gene probed on different arrays is computed and used to divide the Chip normalised signal of the same gene. This procedure is repeated for every other gene. This is called Gene normalisation.

The initial 1134 genes list were filtered as previously described (→1.5 fold change): the two classes of patients considered in this case (as opposed to the breast cancer patients, where we evaluated the propensity to formation of metastatic tumours) are the Dead-of disease group, and the Disease-Free Survival group.

Then, on the filtered list, we ranked the genes according to their ability to discriminate between the two sets of patients, by Univariate t-test (p-value less than 0.05).

We performed the same analyses on both published datasets, and then we selected only the top ranked common genes found on both the datasets.

We repeated the same ranking analysis, but with a more stringent p-value cut-off (<0.001). Thus, we obtained a list of top ranked genes from the merged datasets. At the end, we reduced these lists of genes to a final list of 12 genes (lung predictor) by different Class prediction statistical algorithms (Analyses were performed using BRB ArrayTools). The genes are shown in table 3, below.

TABLE 3

| UGCluster | Name | Symbol | LLID | UGRepAcc | LLRepProtAcc | Cytoband |
|---|---|---|---|---|---|---|
| Hs.108371 | E2F transcription factor 4, p107/p130-binding | E2F4 | 1874 | NM_001950 | NP_001941 | 16q21-q22 |
| Hs.155048 | Lutheran blood group (Auberger b antigen included) | LU | 4059 | BC050450 | NP_005572 | 19q13.2 |
| Hs.245540 | ADP-ribosylation factor-like 4A | ARL4A | 10124 | NM_005738 | NP_997625 | 7p21-p15.3 |
| Hs.334534 | glucosamine (N-acetyl)-6-sulfatase (Sanfilippo disease IIID) | GNS | 2799 | NM_002076 | NP_002067 | 12q14 |
| Hs.409934 | major histocompatibility complex, class II, DQ beta 1 | HLA-DQB1 | 3119 | BM701265 | NP_002114 | 6p21.3 |
| Hs.436432 | raft-linking protein | RAFTLIN | 23180 | NM_015150 | NP_055965 | 3p25.1 |
| Hs.444439 | phosphoribosylaminoimidazole carboxylase, phosphoribosylaminoimidazole succinocarboxamide synthetase | PAICS | 10606 | BX538303 | NP_006443 | 4pter-q21 |
| Hs.505806 | pre-B-cell leukemia transcription factor interacting protein 1 | PBXIP1 | 57326 | NM_020524 | NP_065385 | 1q22 |
| Hs.55279 | serine (or cysteine) proteinase inhibitor, clade B (ovalbumin), member 5 | SERPINB5 | 5268 | BX640597 | NP_002630 | 18q21.3 |
| Hs.79037 | heat shock 60 kDa protein 1 (chaperonin) | HSPD1 | 3329 | BC047350 | NP_955472 | 2q33.1 |
| Hs.79402 | polymerase (RNA) II (DNA directed) polypeptide C, 33 kDa | POLR2C | 5432 | BC003159 | NP_116558 | 16q13-q21 |
| Hs.91747 | profilin 2 | PFN2 | 5217 | BC043646 | NP_444252 | 3q25.1-q25.2 |

The predictor is able to determine the risk to death within 29 months. FIG. 19 shows the survival probability with a good or poor expression signature based on the NSCLC predictor, using the dataset of Beer et al (FIG. 19A) or the dataset of Bhattacharjee et al (FIG. 19B).

A significant difference was found between the probability of survival of the two groups, using the Log-rank test to calculate P-values.

A good signature was considered to be one which has at least 7 out of the 12 genes (i.e., the majority of genes) which are:
1. For HLA-DQB1, LU, GNS, POLR2C, PBXIP1 and RAFTLIN, upregulated compared to other individuals in the analysis (the poor prognosis group);
1. For E2F4, PAICS, PFN2, SERPINB5, HSPD1, and ARL4A, downregulated compared to other individuals in the analysis (the poor prognosis group).

The individuals in the analysis were from both of the above datasets.

The expression profile of the 12 lung gene predictor on an independent set of patients composed of 30 tissue specimens (all stage I NSCLC adenocarcinomas) was also evaluated by Q-RT-PCR. The "test" set of patients was composed of 15 patients without evidence of disease (the good outcome group) and 15 patients died of disease (the poor outcome group). The results of the "test" screening confirmed the good performance of our 12 genes classifier (see FIG. 19C).

In addition, in order to test the predictive potential of other candidate genes, the Micro-fluidic Card (Applied Biosystem) technology was employed. Therefore, in this low density array card, in addition to the 12 genes of Table 3, other 38 genes selected from the list of top ranked genes from the merged data sets were also included. The results of the "test" screening showed that a combination of 21 genes (also including 5 of the previously identified 12 genes) (see Table 4 and FIG. 19D) displayed an improved performance in predicting NSCLC patients' outcome. Moreover, the 21 genes predictor appeared to be a novel prognosis predictor also for early stages NSCLC patients (stage I).

TABLE 4

| UGCluster | Name | Symbol | LLID | UGRepAcc | LLRepProtAcc | Cytoband |
|---|---|---|---|---|---|---|
| Hs.96055 | E2F transcription factor 1 | E2F1 | 1869 | BC050369 | NP_005216 | 20q11.2 |
| Hs.438720 | MCM7 minichromosome maintenance deficient 7 (S. cerevisiae) | MCM7 | 4176 | NM_182776 | NP_877577 | 7q21.3-q22.1 |
| Hs.226390 | Ribonucleotide reductase M2 polypeptide | RRM2 | 6241 | AK123010 | NP_001025 | 2p25-p24 |
| Hs.460184 | MCM4 minichromosome maintenance deficient 4 (S. cerevisiae) | MCM4 | 4173 | NM_005914 | NP_877423 | 8q11.2 |
| Hs.444118 | MCM6 minichromosome maintenance deficient 6 (MIS5 homolog, S. pombe) (S. cerevisiae) | MCM6 | 4175 | NM_005915 | NP_005906 | 2q21 |
| Hs.550539 | NudC domain containing 1 | CML66 | 84955 | BC043406 | NP_116258 | 8q23 |
| Hs.471011 | Splicing factor 3b, subunit 1, 155 kDa | SF3B1 | 23451 | NM_012433 | NP_036565 | 2q33.1 |

TABLE 4-continued

| UGCluster | Name | Symbol | LLID | UGRepAcc | LLRepProtAcc | Cytoband |
|---|---|---|---|---|---|---|
| Hs.529609 | ATPase type 13A3 | ATP13A3 | 79572 | AJ306929 | NP_078800 | 3q29 |
| Hs.164021 | Chemokine (C-X-C motif) ligand 6 (granulocyte chemotactic protein 2) | CXCL6 | 6372 | BM994397 | NP_002984 | 4q21 |
| Hs.546852 | GA binding protein transcription factor, beta subunit 2, 47 kDa | GABPB2 | 2553 | BC036080 | NP_852092 | 15q21.2 |
| Hs.479728 | glyceraldehyde-3-phosphate dehydrogenase | GAPDH | 2597 | NM_002046 | NP_002037 | 12p13 |
| Hs.404321 | Glycyl-tRNA synthetase | GARS | 2617 | NM_002047 | NP_002038 | 7p15 |
| Hs.436181 | Homeo box B7 | HOXB7 | 3217 | AK223249 | NP_004493 | 17q21.3 |
| Hs.550478 | Heparan sulfate proteoglycan 2 (perlecan) | HSPG2 | 3339 | M85289 | NP_005520 | 1p36.1-p35 |
| Hs.360033 | DNA replication complex GINS protein PSF1 | KIAA0186 | 9837 | XM_375911 | NP_066545 | 20p11.21 |
| Hs.62492 | Secretoglobin, family 3A, member 1 | SCGB3A1 | 92304 | BU607563 | NP_443095 | 5q35-qter |
| Hs.108371 | E2F transcription factor 4, p107/p130-binding | E2F4 | 1874 | NM_001950 | NP_001941 | 16q21-q22 |
| Hs.409934 | major histocompatibility complex, class II, DQ beta 1 | HLA-DQB1 | 3119 | BM701265 | NP_002114 | 6p21.3 |
| Hs.436432 | raft-linking protein | RAFTLIN | 23180 | NM_015150 | NP_055965 | 3p25.1 |
| Hs.55279 | serine (or cysteine) proteinase inhibitor, clade B (ovalbumin), member 5 | SERPINB5 | 5268 | BX640597 | NP_002630 | 18q21.3 |
| Hs.91747 | profilin 2 | PFN2 | 5217 | BC043646 | NP_444252 | 3q25.1-q25.2 |

A good signature was considered to be one which has at least
11 genes out of the 21 genes (i.e., the majority of genes) which are:
1. For HLA-DQB1, and RAFTLIN, upregulated compared to other individuals in the analysis (the poor prognosis group).
2. For PFN2, SERPINB5, E2F4, E2F1, MCM7, RRM2, MCM4, MCM6, CML66, SF3B1, ATP13A3, CXCL6, GABPB2, GAPDH, GARS, HOXB7, HSPG2, KIAA0186, SCGB3A1, downregulated compared to other individuals in the analysis (the poor prognosis group).

SUMMARY

We have validated our initial hypothesis that a biased screening of cancer transcriptomes might lead to the identification of a bona fide cancer signature.

We have shown that a biased method of screening the cancer transciptome, looking at genes whose expression is modulated in response to E1A, can provide a good predictor of cancer progression, providing a significant difference in the risk of cancer progression between patients with a good and with a poor signature.

In respect of the class D genes, the precise molecular knowledge of both the starting and the end points of the identified pathway (E1A and class D genes, respectively) should now allow the identification of the genetic alterations, naturally occurring in a sizable fraction of human cancers, which are predicted to lie in a pathway activated by E1A, but independent of pocket proteins and E2Fs. We note that the interference with distal alterations, in a cancer subverted pathway, might prove rather advantageous for therapeutic purposes. In principle, the interference with an upstream genetic lesion might have undesirable consequences also in normal cells, while the selective intervention on distal branches of a signalling pathway might reduce this possibility, as also supported by the fact that the KD of SKIN specifically inhibited the proliferation of SKIN-overexpressing cells.

Class D genes encode for rather heterogeneous proteins, including proteins involved in RNA splicing (SAP1 and Smu-1), a nucleolar RNA helicase (DDX21), a microtubule-associated protein (CH-TOG), a component of the TNF-R1 pathway leading to activation of NF-KB (RRIP), and a previously unknown protein displaying no distinguishing dominial feature (SKIN). While this heterogeneity, albeit not surprising in a cancer transcriptional signature, cannot be immediately reconciled in a unifying scenario, we also note that recent results unexpectedly involved ribonuclear complexes containing splicing factors and RNA-binding proteins in cytoskeletal regulation leading to cell adhesion (de Hoog et al, 2004). Thus, it is possible that we have identified a cluster of genes whose regulation is important in determining phenotypes frequently altered in cancer, such as cell adhesion to the substrate and motility.

In additional, we have also shown that other classes of E1A-regulated genes can be used as predictors of the metastatic risk of cancer patients.

The references mentioned herein are all expressly incorporated by reference in their entirety.

REFERENCES

1. Frise, E., Knoblich, J. A., Younger-Shepherd, S., Jan, L. Y. & Jan, Y. N. The *Drosophila* Numb protein inhibits signaling of the Notch receptor during cell-cell interaction in sensory organ lineage. *Proc Natl Acad Sci USA* 93, 11925-32 (1996).
2. Guo, M., Jan, L. Y. & Jan, Y. N. Control of daughter cell fates during asymmetric division: interaction of Numb and Notch. *Neuron* 17, 27-41 (1996).
3. Artavanis-Tsakonas, S., Rand, M. D. & Lake, R. J. Notch signaling: cell fate control and signal integration in development. *Science* 284, 770-6 (1999).
4. Gallahan, D. et al. Expression of a truncated Int3 gene in developing secretory mammary epithelium specifically retards lobular differentiation resulting in tumorigenesis. *Cancer Res* 56, 1775-85 (1996).
5. Robbins, J., Blondel, B. J., Gallahan, D. & Callahan, R. Mouse mammary tumor gene int-3: a member of the notch gene family transforms mammary epithelial cells. *J Virol* 66, 2594-9 (1992).
6. Capobianco, A. J., Zagouras, P., Blaumueller, C. M., Artavanis-Tsakonas, S. & Bishop, J. M. Neoplastic transformation by truncated alleles of human NOTCH1/TAN1 and NOTCH2. *Mol Cell Biol* 17, 6265-73 (1997).
7. Jeffries, S. & Capobianco, A. J. Neoplastic transformation by Notch requires nuclear localization. *Mol Cell Biol* 20, 3928-41 (2000).
8. Weijzen, S. et al. Activation of Notch-1 signaling maintains the neoplastic phenotype in human Ras-transformed cells. *Nat Med* 8, 979-86 (2002).
9. Soriano, J. V., Uyttendaele, H., Kitajewski, J. & Montesano, R. Expression of an activated Notch4 (int-3) oncoprotein disrupts morphogenesis and induces an invasive phenotype in mammary epithelial cells in vitro. *Int J Cancer* 86, 652-9 (2000).
10. Ellisen, L. W. et al. TAN-1, the human homolog of the *Drosophila* notch gene, is broken by chromosomal translocations in T lymphoblastic neoplasms. *Cell* 66, 649-61 (1991).
11. Jhappan, C. et al. Expression of an activated Notch-related int-3 transgene interferes with cell differentiation and induces neoplastic transformation in mammary and salivary glands. *Genes Dev* 6, 345-55 (1992).
12. Rhyu, M. S., Jan, L. Y. & Jan, Y. N. Asymmetric distribution of numb protein during division of the sensory organ precursor cell confers distinct fates to daughter cells. *Cell* 76, 477-91 (1994).
13. Santolini, E. et al. Numb is an endocytic protein. *J Cell Biol* 151, 1345-52 (2000).
14. Nie, J. et al. LNX functions as a RING type E3 ubiquitin ligase that targets the cell fate determinant Numb for ubiquitin-dependent degradation. *Embo J* 21, 93-102 (2002).
15. Zagouras, P., Stifani, S., Blaumueller, C. M., Carcangiu, M. L. & Artavanis-Tsakonas, S. Alterations in Notch signaling in neoplastic lesions of the human cervix. *Proc Natl Acad Sci USA* 92, 6414-8 (1995).
16. Schroeter, E. H., Kisslinger, J. A. & Kopan, R. Notch-1 signalling requires ligand-induced proteolytic release of intracellular domain. *Nature* 393, 382-6 (1998).
17. Struhl, G. & Adachi, A. Requirements for presenilin-dependent cleavage of notch and other transmembrane proteins. *Mol Cell* 6, 625-36 (2000).
18. Jarriault, S. et al. Signalling downstream of activated mammalian Notch. *Nature* 377, 355-8 (1995).
19. Jarriault, S. et al. Delta-1 activation of notch-1 signaling results in HES-1 transactivation. *Mol Cell Biol* 18, 7423-31 (1998).
20. Zhong, W., Feder, J. N., Jiang, M. M., Jan, L. Y. & Jan, Y. N. Asymmetric localization of a mammalian numb homolog during mouse cortical neurogenesis. *Neuron* 17, 43-53 (1996).
21. Sasai, Y., Kageyama, R., Tagawa, Y., Shigemoto, R. & Nakanishi, S. Two mammalian helix-loop-helix factors structurally related to *Drosophila* hairy and Enhancer of split. *Genes Dev* 6, 2620-34 (1992).
22. Berezovska, O. et al. Aspartate mutations in presenilin and gammasecretase inhibitors both impair notch1 proteolysis and nuclear translocation with relative preservation of notch1signaling. *J Neurochem* 75, 583-93 (2000).
23. Weng, A. P. et al. Growth suppression of pre-T acute lymphoblastic leukemia cells by inhibition of notch signaling. *Mol Cell Biol* 23, 655-64 (2003).
24. Woods, D. B. & Vousden, K. H. Regulation of p53 function. *Exp Cell Res* 264, 56-66 (2001).
25. Vogelstein, B., Lane, D. & Levine, A. J. Surfing the p53 network. *Nature* 408, 307-10 (2000).
26. Juven-Gershon, T. et al. The Mdm2 oncoprotein interacts with the cell fate regulator Numb. *Mol Cell Biol* 18, 3974-82 (1998).
27. Susini, L. et al. Siah-1 binds and regulates the function of Numb. *Proc Natl Acad Sci USA* 98, 15067-72 (2001).
28. Karin, M. & Ben-Neriah, Y. Phosphorylation meets ubiquitination: the control of NF-[kappa]B activity. *Annu Rev Immunol* 18, 621-63 (2000).
29. Pickart, C. M. Mechanisms underlying ubiquitination. *Annu Rev Biochem* 70, 503-33 (2001).
30. Chien, C. T., Wang, S., Rothenberg, M., Jan, L. Y. & Jan, Y. N. Numb associated kinase interacts with the phosphotyrosine binding domain of Numb and antagonizes the function of Numb in vivo. *Mol Cell Biol* 18, 598-607 (1998).
31. Speirs, V. et al. Short-term primary culture of epithelial cells derived from human breast tumours. *Br J Cancer* 78, 1421-9 (1998).
32. Hammond, S. L., Ham, R. G. & Stampfer, M. R. Serum-free growth of human mammary epithelial cells: rapid clonal growth in defined medium and extended serial passage with pituitary extract. *Proc Natl Acad Sci USA* 81, 5435-9 (1984).

Alevizopoulos, K., Catarin, B., Vlach, J. & Amati, B. (1998). *Embo J,* 17, 5987-97.

Alevizopoulos, K., Sanchez, B. & Amati, B. (2000). *Oncogene,* 19, 2067-74.

de Hoog, C.L., Foster, L.J. & Mann, M. (2004). *Cell,* 117, 649-62.

Deleu, L., Shellard, S., Alevizopoulos, K., Amati, B. & Land, H. (2001). *Oncogene,* 20, 8270-5.

Dorsman, J.C., Hagmeyer, B.M., Veenstra, J., Elfferich, P., Nabben, N., Zantema, A. & van der Eb, A. J. (1995). *J Virol,* 69, 2962-7.

Ferreira, R., Magnaghi-Jaulin, L., Robin, P., Harel-Bellan, A. & Trouche, D. (1998). *Proc Natl Acad Sci USA,* 95, 10493-8.

Fuchs, M., Gerber, J., Drapkin, R., Sif, S., Ikura, T., Ogryzko, V., Lane, W. S., Nakatani, Y. & Livingston, D. M. (2001). *Cell*, 106, 297-307.

Sandmoller, A., Meents, H. & Arnold, H. H. (1996). *Mol Cell Biol*, 16, 5846-56.

Subramanian, T., Kuppuswamy, M., Nasr, R. J. & Chinnadurai, G. (1988). *Oncogene*, 2, 105-12.

van't Veer, L.J., Dai, H., van de Vijver, M. J., He, Y. D., Hart, A. A., Mao, M., Peterse, H. L., van der Kooy, K., Marton, M. J., Witteveen, A. T., Schreiber, G. J., Kerkhoven, R. M., Roberts, C., Linsley, P. S., Bernards, R. & Friend, S. H. (2002). *Nature*, 415, 530-6.

Vooijs, M., van der Valk, M., te Riele, H. & Berns, A. (1998). *Oncogene*, 17, 1-12.

The invention claimed is:

1. A method of determining susceptibility of a breast tumor in a patient to treatment with an inhibitor of Notch signaling comprising:
providing an assay sample of breast tumor tissue obtained from said patient; and
determining the Numb status of said sample, wherein a lower level of Numb is associated with susceptibility of the tumor to treatment with a Notch inhibitor.

2. The method of claim 1, wherein determining the Numb status of said assay sample comprises determining the level of Numb protein in said sample.

3. The method of claim 2, wherein the method further comprises comparing said level to a reference level obtained from a control sample.

4. The method of claim 1, further comprising administering an inhibitor of Notch signaling to said patient.

5. The method claim 4, further comprising measuring Notch activity in a sample obtained from a patient prior to and subsequent to the administration of said inhibitor.

6. The method of claim 5 wherein measuring Notch activity comprises measuring the expression level of at least one gene whose expression is regulated by Notch.

* * * * *